(12) United States Patent
De Bont et al.

(10) Patent No.: US 10,941,421 B2
(45) Date of Patent: *Mar. 9, 2021

(54) YEAST STRAINS ENGINEERED TO PRODUCE ETHANOL FROM ACETIC ACID AND GLYCEROL

(71) Applicant: DSM IP ASSETS B.V., Heerlen (NL)

(72) Inventors: Johannes Adrianus Maria De Bont, Echt (NL); Aloysius Wilhelmus Rudolphus Hubertus Teunissen, Echt (NL); Paul Klaassen, Echt (NL); Wouter Willem Antonius Hartman, Echt (NL); Shimaira Van Beusekom, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,018

(22) Filed: May 3, 2018

(65) Prior Publication Data
US 2018/0251798 A1 Sep. 6, 2018

Related U.S. Application Data

(63) Continuation of application No. 14/361,782, filed as application No. PCT/NL2012/050841 on Nov. 26, 2012, now Pat. No. 9,988,649.

(60) Provisional application No. 61/564,932, filed on Nov. 30, 2011.

(30) Foreign Application Priority Data

Nov. 30, 2011 (EP) ...................................... 11191333

(51) Int. Cl.
| C12P 7/06 | (2006.01) |
| C12N 1/22 | (2006.01) |
| C12N 9/04 | (2006.01) |
| C12N 9/02 | (2006.01) |
| C12P 7/08 | (2006.01) |
| C12P 7/10 | (2006.01) |

(52) U.S. Cl.
CPC .................. *C12P 7/06* (2013.01); *C12N 1/22* (2013.01); *C12N 9/0006* (2013.01); *C12N 9/0008* (2013.01); *C12P 7/08* (2013.01); *C12P 7/10* (2013.01); *C12Y 101/01006* (2013.01); *C12Y 102/0101* (2013.01); *C12Y 102/01* (2013.01); *Y02E 50/10* (2013.01)

(58) Field of Classification Search
None
See application file for complete search history.

(56) References Cited

U.S. PATENT DOCUMENTS 9,988,649 B2 * 6/2018 De Bont .................. C12N 1/22

FOREIGN PATENT DOCUMENTS

| WO | 2011140386 A2 | 11/2011 |
| WO | 2011149353 A1 | 12/2011 |
| WO | 2011153516 A2 | 12/2011 |
| WO | 2012067510 A1 | 5/2012 |

OTHER PUBLICATIONS

Bellissimi et al. Effects of acetic acid on the kinetics of xylose fermentation by an engineered, xylose-isomerase-based *Saccharomyces cerevisiae* strain. FEMS Yeast Res 9 (2009) 358-364.*
Guadalupe Medina V. et al., "Elimination of Glycerol Production in Anaerobic Cultures of a *Saccharomyces cerevisiae* Strain Engineered to Use Acetic Acid as an Electron Acceptor", Applied and Environmental Microbiology, 76:90-195 (Jan. 1, 2010).
Liang Zhang et al., "Improving the ethanol yield by reducing glycerol formation using cofactor regulation in *Saaccharomyces cerevisiae*", Biotechnology Letters, 33:375-1380 (Mar. 13, 2011).
Yu Kyung Ok et al., "Engineering of glycerol utilization pathway for ethanol production by *Saccharomyces cerevisiae*", Bioresource Technology, 101:4157-4161 (Jun. 1, 2010).
Bjorn Holst et al., "GUP1 and its close homologue GUP2, encoding multimembrane-spanning proteins involved in active glycerol uptake in *Saccharomyces cerevisiae*", Molecular Microbiology, 37:108-124 (Jul. 1, 2000).
Luyten Kattie et al. "Fps1, a yeast member of the MIP family of channel proteins, is a facillitator for glycerol uptake and efflux and is inactive under osmotic stress", EMBO Journal 14:1360-1371 (Jan. 1, 1995).
Albertyn J. et al., "Gdp1, which encodes glycerol 3-phosphate dehydrogenase, is essential for growth under osmotic stress in *Saccharomyces* and its expression is regulated by the high-osmolarity glycerol response pathway" Molecular and Cellular Biology, 14:4135-4144 (Jun. 1, 1994).

(Continued)

Primary Examiner — Iqbal H Chowdhury
(74) Attorney, Agent, or Firm — McBee Moore & Vanik IP, LLC

(57) ABSTRACT

The present invention relates to processes for producing ethanol from lignocellulosic hydrolysates comprising, hexoses, pentoses and acetic acid, whereby genetically modified yeast cells are use that comprise an exogenous gene encoding an acetaldehyde dehydrogenase and a bacterial gene encoding an enzyme with $NAD^+$-linked glycerol dehydrogenase activity. The process is further characterised in that glycerol is present in or fed into the culture medium, whereby the modified yeast cell ferments the hexoses, pentoses, acetic acid and glycerol to ethanol. The invention further relates to yeast cells for use in such processes. The yeast cells advantageously comprise genetic modifications that improve glycerol utilization such as modifications that increase one or more of dihydroxyacetone kinase activity and transport of glycerol into the cell. The yeast cell further preferably comprises a functional exogenous xylose isomerase gene and/or functional exogenous genes which confer to the cell the ability to convert L-arabinose into D-xylulose 5-phosphate and they may comprise a genetic modification that increase acetyl-CoA synthetase activity.

13 Claims, 1 Drawing Sheet
Specification includes a Sequence Listing.

(56) References Cited

OTHER PUBLICATIONS

Van Maris A. J. A. et al, "Alcoholic fermentation of carbon sources in biomass hydrolysates by *Saccharomyces cerevisiae*: current status" Antonie Van Leeuwenhoek, 90:391-418 (Oct. 11, 2006).
Shams Yazdani S. et al., "Engineering *Escherichia coli* for the efficient conversion of glycerol to ethanol and co-products" Metabolic Engineering, 10:340-351 (Nov. 1, 2008).
Lee W. et al., "Application of sequential integration for metabolic engineering of 1,2-propanediol production in yeast", Metabolic Engineering, Academic Press, pp. 58-65, vol. 8, No. 1 (Jan. 1, 2006).
Whisstock et al., "Prediction of protein function from protein sequence and structure", Quarterly Reviews of Biophysics, 2003, 36(3): 307-340.
Witkowski et al., "Conversion of a beta-ketoacyl synthase to a malonyl decarboxylase by replacement of the active-site cysteine with glutamine", Biochemistry, Sep. 7, 1999, 38(36):11643-50.

\* cited by examiner

YEAST STRAINS ENGINEERED TO PRODUCE ETHANOL FROM ACETIC ACID AND GLYCEROL

CROSS-REFERENCE TO RELATED APPLICATIONS

This application is a Continuation application of U.S. patent application Ser. No. 14/361,782, filed 30 May 2014, which is a National Stage entry of International Application No. PCT/NL2012/050841, filed 26 Nov. 2012, which claims priority to U.S. Provisional Application No. 61/564,932, filed 30 Nov. 2011, and European Patent Application No. 11191333.1, filed 30 Nov. 2011. The disclosures of the priority applications are incorporated in their entirety herein by reference.

FIELD OF THE INVENTION

The present invention relates to metabolic engineering in microorganisms such as yeast. In particular the invention relates to yeast strains that have been engineered to produce ethanol from acetic acid and glycerol. In addition to acetic acid and glycerol, the yeast strain may also consume hexoses and pentoses for the production of ethanol. The invention further relates to the processes wherein the engineered strains of the invention produce ethanol from acetic acid and glycerol.

BACKGROUND OF THE INVENTION

Second generation bioethanol is produced from e.g. lignocellulosic fractions of plant biomass that is hydrolysed to free monomeric sugars, such as hexoses and pentoses, for fermentation to ethanol. Lignocellulosic hydrolysates contain high amounts of acetic acid, which is a potent inhibitor of the fermentative capacities of microorganisms used for ethanol production such as yeasts.

Sonderegger et al. (2004, Appl. Environ. Microbiol. 70: 2892-2897) disclose heterologous expression of phosphotransacetylase and acetaldehyde dehydrogenase in xylose-fermenting *Saccharomyces cerevisiae* strain. In combination with the native phosphoketolase, Sonderegger et al. thereby created a functional phosphoketolase pathway that is capable of net reoxidation of NADH generated by the heterologous expression of a xylose reductase and xylitol dehydrogenase that are used for xylose utilization in the strain.

Guadalupe et al. (2009, Appl. Environ. Microbiol. doi: 10.1128/AEM.01772-09) disclose a *Saccharomyces cerevisiae* strain wherein production of the by-product glycerol is eliminated by disruption of the endogenous NAD-dependent glycerol 3-phosphate dehydrogenase genes (GPD1 and GPD2). Expression of the *E. coli* mhpF gene, encoding the acetylating NAD-dependent acetaldehyde dehydrogenase restored the ability of the GPD-disrupted strain to grow anaerobically by supplementation with of the medium with acetic acid.

Yu et al. (2010, Bioresour. Technol. 101(11):4157-61. Epub 2010 Feb. 9) disclose *Saccharomyces cerevisiae* strains metabolically engineered for improved ethanol production from glycerol by simultaneous overexpression of glycerol dehydrogenase (GCY), dihydroxyacetone kinase (DAK) and the glycerol uptake protein (GUP1).

Lee and Dasilva (2006, Metab Eng. 8(1):58-65) disclose the yeast *Saccharomyces cerevisiae* engineered to produce 1,2-propanediol from glycerol by inter alia introducing expression of the *Escherichia coli* mgs and gldA genes.

It is an object of the present invention to provide for yeasts that are capable of producing ethanol from acetic acid and glycerol (and hexoses and pentoses), as well as processes wherein these strains are used for the production of ethanol and/or other fermentation products.

DESCRIPTION OF THE INVENTION

Definitions

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty: 10; Gap extension penalty: 0.05). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenyl alanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to g/l; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

"Fungi" (singular fungus) are herein understood as heterotrophic eukaryotic microorganism that digest their food externally, absorbing nutrient molecules into their cells. Fungi are a separate kingdom of eukaryotic organisms and include yeasts, molds, and mushrooms. The terms fungi, fungus and fungal as used herein thus expressly includes yeasts as well as filamentous fungi.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'nontranslated sequence (3'end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not nominally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The "specific activity" of an enzyme is herein understood to mean the amount of activity of a particular enzyme per amount of total host cell protein, usually expressed in units of enzyme activity per mg total host cell protein. In the context of the present invention, the specific activity of a particular enzyme may be increased or decreased as compared to the specific activity of that enzyme in an (otherwise identical) wild type host cell.

"Anaerobic conditions" or an anaerobic fermentation process is herein defined as conditions or a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors.

DETAILED DESCRIPTION OF THE INVENTION

Expression of an exogenous acetaldehyde dehydrogenase in yeast allows the yeast to convert acetic acid, which may be present in high amounts in lignocellulosic hydrolysates, to ethanol. The NADH dependent reduction of acetic acid to ethanol has been proposed as a replacement for glycerol formation as a redox sink in anaerobic glucose-grown cultures of S. cerevisiae, thus providing a stoichiometric basis for elimination of glycerol production (as byproduct) during industrial ethanol production and consequently a higher ethanol yield (Guadalupe et al. supra). However, the stoichiometry of these reactions is such that the reduction of one molecule of acetic acid to ethanol would require two glycerol molecules not being produced. The present inventors have found however, that in practice the amount of acetic acid that typically is present in industrial lignocellulosic hydrolysates is such that the amount of NADH required for it to be reduced to ethanol exceeds the amount of NADH that would become available from preventing glycerol production in yeasts grown under anaerobic conditions. The present inventors have now surprisingly found that much higher amounts of acetic acid can be reduced to ethanol by simultaneous consumption of glycerol by the yeast, rather than by preventing its production.

Large amounts of glycerol are generated as a by-product in biodiesel production from transesterification reactions using vegetable oils or animal fats and an alcohol. The availability of crude glycerol is therefore predicted to increase over the next years as a result of the growth in biodiesel production worldwide. Consequently large amounts of glycerol will be available at low cost. The present invention provides means and methods for valorising glycerol, obtained e.g. as by-product from biodiesel production, by converting it to ethanol that may be used as biofuel. At the same time the present invention addresses the problem of high amounts of acetic acid that are present in lignocellulosic hydrolysates and which inhibit the fermentative capacities of yeasts producing ethanol from these hydrolysates. A further advantage of the present invention is that by leaving the high-osmolarity glycerol response pathway intact in the yeast cells of the invention (as opposed to strains wherein (all) glycerolphosphate dehydrogenase genes are inactivated as described by Guadalupe et al. supra), more robust yeast strains are obtained that are better capable of handling osmotic stress that may occur under industrial fermentations conditions.

In a first aspect the invention relates to a fungal host cell comprising an exogenous gene coding for a enzyme with the ability to reduce acetylCoA into acetaldehyde, which gene confers to the cell the ability to convert acetic acid into ethanol. An enzyme with the ability to reduce acetylCoA into acetaldehyde is herein understood as an enzyme which catalyze the reaction (ACDH; EC 1.2.1.10):

acetaldehyde+NAD$^+$+Coenzyme A$\leftrightarrow$acetyl-Coenzyme A+NADH+H$^+$.

Thus, the enzyme catalyzes the conversion of acetylCoA into acetaldehyde (and vice versa) and is also referred to as an (acetylating NAD-dependent) acetaldehyde dehydrogenase or an acetyl-CoA reductase. The enzyme may be a bifunctional enzyme which further catalyzes the conversion of acetaldehyde into ethanol (and vice versa; see below). For convenience we shall refer herein to an enzyme having at least the ability to reduce acetylCoA into either acetaldehyde or ethanol as an "acetaldehyde dehydrogenase". It is further understood herein the fungal host cell has endogenous acetyl-CoA synthetase and alcohol dehydrogenase activities which allow the cell, being provided with acetaldehyde dehydrogenase activity, to complete the conversion of acetic acid into ethanol.

The exogenous gene may encode for a monofunctional enzyme having only acetaldehyde dehydrogenase activity (i.e. an enzyme only having the ability to reduce acetylCoA into acetaldehyde) such as e.g. the acetaldehyde dehydrogenase encoded by the E. coli mhpF gene. A suitable exogenous gene coding for an enzyme with acetaldehyde dehydrogenase activity comprises a nucleotide sequence coding for an amino acid sequence with at least 45, 50, 60, 65, 70, 75, 80, 85, 90, 95, 98, 99% amino acid sequence identity with SEQ ID NO: 1. Suitable examples of prokaryotes comprising monofunctional enzymes with acetaldehyde dehydrogenase activity are provided in Table 1. The amino acid sequences of these monofunctional enzymes are available in public databases and can be used by the skilled person to design codon-optimised nucleotide sequences coding for the corresponding monofunctional enzyme (see e.g. SEQ ID NO: 2).

TABLE 1

Enzymes with acetaldehyde dehydroenase activity related to *E. coli* mhpF

| Organism | Amino acid identity (%) |
|---|---|
| *Escherichia coli* str. K12 substr. MG1655 | 100% |
| *Shigella sonnei* | 100% |
| *Escherichia coli* IAI39 | 99% |
| *Citrobacter youngae* ATCC 29220 | 93% |
| *Citrobacter* sp. 30_2 | 92% |
| *Klebsiella pneumoniae* 342) | 87% |
| *Klebsiella variicola* | 87% |
| *Pseudomonas putida* | 81% |

TABLE 1-continued

Enzymes with acetaldehyde dehydroenase activity related to *E. coli* mhpF

| Organism | Amino acid identity (%) |
|---|---|
| *Ralstonia eutropha* JMP134 | 82% |
| *Burkholderia* sp. H160 | 81% |
| *Azotobacter vinelandii* DJ | 79% |
| *Ralstonia metallidurans* CH34 | 70% |
| *Xanthobacter autotrophicus* Py2 | 67% |
| *Burkholderia cenocepacia* J2315 | 68% |
| *Frankia* sp. EAN1pec | 67% |
| *Polaromonas* sp. JS666 | 68% |
| *Burkholderia phytofirmans* PsJN | 70% |
| *Rhodococcus opacus* B4 | 64% |

Preferably, the host cell comprises an exogenous gene coding for a bifunctional enzyme with acetaldehyde dehydrogenase and alcohol dehydrogenase activity, which gene confers to the cell the ability to covert acetic acid into ethanol. The advantage of using a bifunctional enzyme with acetaldehyde dehydrogenase and alcohol dehydrogenase activities as opposed to separate enzymes for each of the acetaldehyde dehydrogenase and alcohol dehydrogenase activities, is that it allows for direct channelling of the intermediate between enzymes that catalyze consecutive reactions in a pathway offers the possibility of an efficient, exclusive, and protected means of metabolite delivery. Substrate channelling thus decreases transit time of intermediates, prevents loss of intermediates by diffusion, protects labile intermediates from solvent, and forestalls entrance of intermediates into competing metabolic pathways. The bifunctional enzyme therefore allows for a more efficient conversion of acetic acid into ethanol as compared to the separate acetaldehyde dehydrogenase and alcohol dehydrogenase enzymes. A further advantage of using the bifunctional enzyme is that it may also be used in host cells having little or no alcohol dehydrogenase activity under the condition used, such as e.g. anaerobic conditions and/or conditions of catabolite repression.

Bifunctional enzymes with acetaldehyde dehydrogenase and alcohol dehydrogenase activity are known in the art prokaryotes and protozoans, including e.g. the bifunctional enzymes encoded by the *Escherichia coli* adhE and *Entamoeba histolytic* ADH2 genes (see e.g. Bruchaus and Tannich, 1994, J. Biochem. 303: 743-748; Burdette and Zeikus, 1994, J. Biochem. 302: 163-170; Koo et al., 2005, Biotechnol. Lett. 27: 505-510; Yong et al., 1996, Proc Natl Acad Sci USA, 93: 6464-6469). Bifunctional enzymes with acetaldehyde dehydrogenase and alcohol dehydrogenase activity are larger proteins consisting of around 900 amino acids and they are bifunctional in that they exhibit both acetaldehyde dehydrogenase (ACDH; EC 1.2.1.10) and alcohol dehydrogenase activity (ADH; EC 1.1.1.1). The *E. coli* adhE and *Entamoeba histolytica* ADH show 45% amino acid identity. Therefore, in one embodiment of the invention, a suitable exogenous gene coding for a bifunctional enzyme with acetaldehyde dehydrogenase and alcohol dehydrogenase activity comprises a nucleotide sequence coding for an amino acid sequence with at least 45, 50, 60, 65, 70, 75, 80, 85, 90, 95, 98, 99% amino acid sequence identity with at least one of SEQ ID NO: 3 and 5. Suitable examples of prokaryotes comprising bifunctional enzymes with acetaldehyde dehydrogenase and alcohol dehydrogenase activity are provided in Tables 2 and 3. The amino acid sequences of these bifunctional enzymes are available in public databases and can be used by the skilled person to design codon-optimised nucleotide sequences coding for the corresponding bifunctional enzyme (see e.g. SEQ ID NO: 4 or 6).

TABLE 2

Bifunctional enzymes with acetaldehyde dehydrogenase and alcohol dehydrogenase activity related to E. coli adhE

| Organism | Amino acid identity (%) |
|---|---|
| Escherichia coli O157:H7 str. Sakai | 100% |
| Shigella sonnei | 100% |
| Shigella dysenteriae 1012 | 99% |
| Klebsiella pneumoniae 342 | 97% |
| Enterobacter sp. 638 | 94% |
| Yersinia pestis biovar Microtus str. 91001 | 90% |
| Serratia proteamaculans 568 | 90% |
| Pectobacterium carotovorum WPP14 | 90% |
| Sodalis glossinidius str. 'morsitans' | 87% |
| Erwinia tasmaniensis Et1/99 | 86% |
| Aeromonas hydrophila ATCC 7966 | 81% |
| Vibrio vulnificus YJ016] | 76% |

TABLE 3

Bifunctional enzymes with acetaldehyde dehydrogenase and alcohol dehydrogenase activity related to Entamoeba histolytica ADH2

| Organism | Amino acid identity (%) |
|---|---|
| Entamoeba histolytica HM-1:IMSS | 99% |
| Entamoeba dispar SAW760 | 98% |
| Mollicutes bacterium D7 | 65% |
| Fusobacterium mortiferum ATCC 9817 | 64% |
| Actinobacillus succinogenes 130Z | 63% |
| Pasteurella multocida Pm70 | 62% |
| Mannheimia succiniciproducens MBEL55E | 61% |
| Streptococcus sp. 2_1_36FAA] | 61% |

The exogenous gene coding for the bifunctional enzyme having acetaldehyde dehydrogenase and alcohol dehydrogenase activities, for an enzyme having acetaldehyde dehydrogenase activity, preferably is an expression construct comprising a nucleotide sequence coding for the enzyme operably linked to suitable expression regulatory regions/sequences to ensure expression of the enzyme upon transformation of the expression construct into the host cell of the invention. Thus, the gene or expression construct will at least comprise a promoter that is functional in the host cell operably linked to the coding sequence. The gene or construct may further comprise a 5' leader sequence upstream of the coding region and a 3'-nontranslated sequence (3'end) comprising a polyadenylation site and a transcription termination site downstream of the coding sequence.

In one aspect the invention relates to methods for preparing or constructing the yeast cells of the invention. For this purpose standard genetic and molecular biology techniques are used that are generally known in the art and have e.g. been described by Sambrook and Russell (2001, "Molecular cloning: a laboratory manual" (3rd edition), Cold Spring Harbor Laboratory, Cold Spring Harbor Laboratory Press) and Ausubel et al. (1987, eds., "Current protocols in molecular biology", Green Publishing and Wiley Interscience, New York). Furthermore, the construction of mutated host yeast strains is carried out by genetic crosses, sporulation of the resulting diploids, tetrad dissection of the haploid spores containing the desired auxotrophic markers, and colony purification of such haploid host yeasts in the appropriate selection medium. All of these methods are standard yeast genetic methods known to those in the art. See, for example, Sherman et al., Methods Yeast Genetics, Cold Spring Harbor Laboratory, NY (1978) and Guthrie et al. (Eds.) Guide To Yeast Genetics and Molecular Biology Vol. 194, Academic Press, San Diego (1991).

Suitable promoters for expression of the nucleotide sequence coding for the enzyme having acetaldehyde dehydrogenase and optionally alcohol dehydrogenase activity (as well as other enzymes of the invention; see below) include promoters that are preferably insensitive to catabolite (glucose) repression, that are active under anaerobic conditions and/or that preferably do not require xylose or arabinose for induction. Promoters having these characteristics are widely available and known to the skilled person. Suitable examples of such promoters include e.g. promoters from glycolytic genes such as the phosphofructokinase (PPK), triose phosphate isomerase (TPI), glyceraldehyde-3-phosphate dehydrogenase (GDP, TDH3 or GAPDH), pyruvate kinase (PYK), phosphoglycerate kinase (PGK), glucose-6-phosphate isomerase promoter (PGI1) promoters from yeasts. More details about such promoters from yeast may be found in (WO 93/03159). Other useful promoters are ribosomal protein encoding gene promoters (TEF1), the lactase gene promoter (LAC4), alcohol dehydrogenase promoters (ADH1, ADH4, and the like), the enolase promoter (ENO) and the hexose(glucose) transporter promoter (HXT7). Alternatively, the nucleotide sequence encoding the enzyme having acetaldehyde dehydrogenase and optionally alcohol dehydrogenase activity is overexpressed under anaerobic conditions by using an anoxic promoter such as e.g. the S. cerevisiae ANB1 promoter (SEQ ID NO: 19). Other promoters, both constitutive and inducible, and enhancers or upstream activating sequences will be known to those of skill in the art. Preferably the promoter that is operably linked to nucleotide sequence as defined above is homologous to the host cell. Suitable terminator sequences are e.g. obtainable from the cytochrome c1 (CYC1) gene or an alcohol dehydrogenase gene (e.g. ADH1).

To increase the likelihood that the enzyme having acetaldehyde dehydrogenase and optionally alcohol dehydrogenase activities is expressed at sufficient levels and in active form in the transformed host cells of the invention, the nucleotide sequence encoding these enzymes, as well as other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the fungal host cell in question such as e.g. S. cerevisiae cells.

The nucleotide sequence encodes an enzyme having acetaldehyde dehydrogenase and optionally alcohol dehydrogenase activities that is preferably expressed in active form in the transformed host cell. Thus, expression of the nucleotide sequence in the host cell produces an acetaldehyde dehydrogenase with a specific activity of at least 0.005, 0.010, 0.020, 0.050 or 0.10 µmol min$^{-1}$ (mg protein)$^{-1}$, determined as acetyl-CoA dependent rate of NADH reduction in cell extracts of the transformed host cell at 30° C. as described in the Examples herein.

The host cell to be transformed with a nucleic acid construct comprising a nucleotide sequence encoding an enzyme with acetaldehyde dehydrogenase and optionally alcohol dehydrogenase preferably is a yeast host cell. Preferably the host cell is a cultured cell. The host cell of the invention, preferably is a host capable of active or passive pentose (xylose and preferably also arabinose) transport into the cell. The host cell preferably contains active glycolysis. The host cell may further preferably contains an endogenous pentose phosphate pathway and may contain endogenous xylulose kinase activity so that xylulose isomerised from xylose may be metabolised to pyruvate. The host further preferably contains enzymes for conversion of a pentose (preferably through pyruvate) to a desired fermentation product such as ethanol, lactic acid, 3-hydroxy-propionic acid, acrylic acid, 1,3-propane-diol, butanols (1-butanol, 2-butanol, isobutanol) and isoprenoid-derived products. A particularly preferred host cell is a yeast cell that is naturally capable of alcoholic fermentation, preferably, anaerobic alcoholic fermentation. The yeast host cell further preferably has a high tolerance to ethanol, a high tolerance to low pH (i.e. capable of growth at a pH lower than 5, 4, or 3) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification, preferably by self cloning or by the methods of the invention described below. A suitable cell is a cultured cell, a cell that may be cultured in fermentation process e.g. in submerged or solid state fermentation. Particularly suitable cells are eukaryotic microorganism like e.g. fungi, however, most suitable for use in the present inventions are yeasts.

Yeasts are herein defined as eukaryotic microorganisms and include all species of the subdivision Eumycotina (Yeasts: characteristics and identification, J. A. Barnett, R. W. Payne, D. Yarrow, 2000, 3rd ed., Cambridge University Press, Cambridge UK; and, The yeasts, a taxonomic study, C. P. Kurtzman and J. W. Fell (eds) 1998, 4$^{th}$ ed., Elsevier Science Publ. B.V., Amsterdam, The Netherlands) that predominantly grow in unicellular form. Yeasts may either grow by budding of a unicellular thallus or may grow by fission of the organism. Preferred yeasts cells for use in the present invention belong to the genera *Saccharomyces, Kluyveromyces, Candida, Pichia, Schizosaccharomyces, Hansenula, Kloeckera, Schwanniomyces*, and *Yarrowia*. Preferably the yeast is capable of anaerobic fermentation, more preferably anaerobic alcoholic fermentation. Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. exiguus, S. bayanus, K. lactis, K. marxianus* and *Schizosaccharomyces pombe*.

In a further embodiment, the host cell of the invention further comprises a genetic modification that introduces NAD$^+$-linked glycerol dehydrogenase activity in the cell. The glycerol dehydrogenase encoded by the endogenous yeast GCY1 gene appears to be specific for the cofactor NADP$^+$ (EC 1.1.1.72) as opposed to NAD$^+$ (EC 1.1.1.6). Yeasts such as *S. cerevisiae* appear to lack NAD$^+$-dependent glycerol dehydrogenase activity (EC 1.1.1.6) (see e.g. KEGG pathway 00561). An NAD$^+$-linked glycerol dehydrogenase is herein understood as an enzyme that catalyzes the chemical reaction (EC 1.1.1.6):

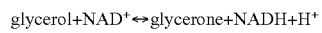

glycerol+NAD$^+$ ⇌ glycerone+NADH+H$^+$

Other names in common use include glycerin dehydrogenase and glycerol: NAD+2-oxidoreductase.

Preferably the genetic modification that introduces NAD$^+$-linked glycerol dehydrogenase activity in the host cell is the expression of an NAD$^+$-linked glycerol dehydrogenase that is heterologous to the host cell. More preferably, the nucleotide sequence for expression of a heterologous glycerol dehydrogenase in the cells of the invention is a sequence encoding a bacterial glycerol dehydrogenase which use NAD$^+$ as cofactor (EC 1.1.1.6). A suitable example of a bacterial NAD$^+$-linked glycerol dehydrogenase for expression in a host cell of the invention is e.g. the gldA gene from *E. coli* described by Truniger and Boos (1994, J Bacteriol. 176(6):1796-1800), the expression of which in yeast has already been reported (Lee and Dasilva, 2006, Metab Eng. 8(1):58-65). Preferably, the nucleotide sequence encoding a heterologous glycerol dehydrogenase comprises a nucleotide sequence coding for an amino acid sequence with at least 45, 50, 60, 65, 70, 75, 80, 85, 90, 95, 98, 99% amino acid sequence identity with SEQ ID NO: 7 or a nucleotide sequence coding for an amino acid sequence having one or several substitutions, insertions and/or deletions as compared to SEQ ID NO: 7. In a preferred embodiment a codon-optimised (see above) nucleotide sequence encoding the heterologous glycerol dehydrogenase is overexpressed, such as e.g. a codon-optimised nucleotide sequence encoding the amino acid sequence of the glycerol dehydrogenase of SEQ ID NO: 7. Such a codon-optimised nucleotide sequence is e.g. provided in SEQ ID NO: 21 (positions 10-1113; CAI=0.976).

For overexpression of the nucleotide sequence encoding the glycerol dehydrogenase, the nucleotide sequence (to be overexpressed) is placed in an expression construct wherein it is operably linked to suitable expression regulatory regions/sequences to ensure overexpression of the glycerol dehydrogenase enzyme upon transformation of the expression construct into the host cell of the invention (see above). Suitable promoters for (over)expression of the nucleotide sequence coding for the enzyme having glycerol dehydrogenase activity include promoters that are preferably insensitive to catabolite (glucose) repression, that are active under anaerobic conditions and/or that preferably do not require xylose or arabinose for induction. Examples of such promoters are given above. Expression of the nucleotide sequence in the host cell produces a specific NAD$^+$-linked glycerol dehydrogenase activity of at least 0.2, 0.5, 1.0, 2.0, or 5.0 U min$^{-1}$ (mg protein)$^{-1}$, determined in cell extracts of the transformed host cells at 30° C. as described in the Examples herein.

In a further embodiment, the host cell of the invention further comprises a genetic modification that increases the specific activity of dihydroxyacetone kinase in the cell.

Transcriptome data has shown that the endogenous DAK1 dihydroxyacetone kinase is already expressed at high levels in S. cerevisiae. A further increase of dihydroxyacetone kinase activity in the cells of the invention may therefore not be strictly necessary. However, in a preferred embodiment, for optimal conversion rates, the host cell of the invention thus comprises a genetic modification that increases the specific activity of dihydroxyacetone kinase in the cell. A dihydroxyacetone kinase is herein understood as an enzyme that catalyzes the chemical reaction ((EC 2.7.1.29):

Other names in common use include glycerone kinase, ATP: glycerone phosphotransferase and (phosphorylating) acetol kinase. It is understood that glycerone and dihydroxyacetone are the same molecule. Preferably the genetic modification causes overexpression of a dihydroxyacetone kinase, e.g. by overexpression of a nucleotide sequence encoding a dihydroxyacetone kinase. The nucleotide sequence encoding the dihydroxyacetone kinase may be endogenous to the cell or may be a dihydroxyacetone kinase that is heterologous to the cell. Nucleotide sequences that may be used for overexpression of dihydroxyacetone kinase in the cells of the invention are e.g. the dihydroxyacetone kinase genes from S. cerevisiae (DAK1) and (DAK2) as e.g. described by Molin et al. (2003, J. Biol. Chem. 278:1415-1423). Preferably, the nucleotide sequence encoding the dihydroxyacetone kinase comprises an amino acid sequence with at least 45, 50, 60, 65, 70, 75, 80, 85, 90, 95, 98, 99% amino acid sequence identity with at least one of SEQ ID NO's: 8 and 9. In a preferred embodiment a codon-optimised (see above) nucleotide sequence encoding the dihydroxyacetone kinase is overexpressed, such as e.g. a codon optimised nucleotide sequence encoding the dihydroxyacetone kinase of SEQ ID NO: 8 or a codon optimised nucleotide sequence encoding the dihydroxyacetone kinase of SEQ ID NO: 9. A preferred nucleotide sequence for overexpression of a dihydroxyacetone kinase is a nucleotide sequence encoding a dihydroxyacetone kinase comprises an amino acid sequence with at least 45, 50, 60, 65, 70, 75, 80, 85, 90, 95, 98, 99% amino acid sequence identity with at least one of SEQ ID NO's: 8 (S. cerevisiae (DAK1) or having one or several substitutions, insertions and/or deletions as compared to SEQ ID NO: 8.

Nucleotide sequences that may be used for overexpression of a heterologous dihydroxyacetone kinase in the cells of the invention are e.g. sequences encoding bacterial dihydroxyacetone kinases such as the dhaK gene from Citrobacter freundii e.g. described by Daniel et al. (1995, J. Bacteriol. 177:4392-4401). Preferably, the nucleotide sequence encoding a heterologous dihydroxyacetone kinase comprises a nucleotide sequence coding for an amino acid sequence with at least 45, 50, 60, 65, 70, 75, 80, 85, 90, 95, 98, 99% amino acid sequence identity with SEQ ID NO: 25 or a nucleotide sequence coding for an amino acid sequence having one or several substitutions, insertions and/or deletions as compared to SEQ ID NO: 25. In a preferred embodiment a codon-optimised (see above) nucleotide sequence encoding the heterologous dihydroxyacetone kinase is overexpressed, such as e.g. a codon optimised nucleotide sequence encoding the amino acid sequence of the dihydroxyacetone kinase of SEQ ID NO: 25. Such a codon-optimised nucleotide sequence is e.g. provided in SEQ ID NO: 26 (positions 10-1668).

For overexpression of the nucleotide sequence encoding the dihydroxyacetone kinase, the nucleotide sequence (to be overexpressed) is placed in an expression construct wherein it is operably linked to suitable expression regulatory regions/sequences to ensure overexpression of the dihydroxyacetone kinase enzyme upon transformation of the expression construct into the host cell of the invention (see above). Suitable promoters for (over)expression of the nucleotide sequence coding for the enzyme having dihydroxyacetone kinase activity include promoters that are preferably insensitive to catabolite (glucose) repression, that are active under anaerobic conditions and/or that preferably do not require xylose or arabinose for induction. Examples of such promoters are given above. In the cells of the invention, a dihydroxyacetone kinase to be overexpressed is preferably overexpressed by at least a factor 1.1, 1.2, 1.5, 2, 5, 10 or 20 as compared to a strain which is genetically identical except for the genetic modification causing the overexpression. Preferably, the dihydroxyacetone kinase is overexpressed under anaerobic conditions by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity (specific activity in the cell), the steady state level of the enzyme's protein as well as to the steady state level of the transcript coding for the enzyme in the cell. Overexpression of the nucleotide sequence in the host cell produces a specific dihydroxyacetone kinase activity of at least 0.002, 0.005, 0.01, 0.02 or 0.05 U min$^{-1}$ (mg protein)$^{-1}$, determined in cell extracts of the transformed host cells at 30° C. as described in the Examples herein.

In a further embodiment, the host cell of the invention further comprises a genetic modification that increases transport of glycerol into the cell. Preferably, the genetic modification that increases transport of glycerol into the cell preferably is a genetic modification that causes overexpression of a nucleotide sequence encoding at least one of a glycerol uptake protein and a glycerol channel.

A glycerol uptake protein is herein understood as a multimembrane-spanning protein that belongs to the included in the membrane bound O-acyltransferases (MBOAT) superfamily including e.g. the S. cerevisiae glycerol uptake proteins encoded by the GUP1 and GUP2 genes. Preferably the genetic modification causes overexpression of a glycerol uptake protein, e.g. by overexpression of a nucleotide sequence encoding a glycerol uptake protein. The nucleotide sequence encoding the glycerol uptake protein may be endogenous to the cell or may be a glycerol uptake protein that is heterologous to the cell. Nucleotide sequences that may be used for overexpression of glycerol uptake protein in the cells of the invention are e.g. the glycerol uptake protein genes from S. cerevisiae (GUP1) and (GUP2) and orthologues thereof as e.g. described by Neves et al. (2004, FEMS Yeast Res. 5:51-62). Preferably, the nucleotide sequence encoding the glycerol uptake protein comprises a nucleotide sequence coding for an amino acid sequence with at least 45, 50, 60, 65, 70, 75, 80, 85, 90, 95, 98, 99% amino acid sequence identity with at least one of SEQ ID NO's: 10 (Gup1p) and 11 (Gup2p). In a preferred embodiment a codon-optimised (see above) nucleotide sequence encoding the glycerol uptake protein is overexpressed, such as e.g. a codon optimised nucleotide sequence encoding the glycerol uptake protein SEQ NO: 10 or a codon optimised nucleotide sequence encoding the glycerol uptake protein of SEQ ID NO: 11. Although the exact nature of the influence of GUP1 on glycerol transport is not yet clear, Yu et al. (2010, supra) have shown that overexpression of GUP1 in S. cerevisiae improves ethanol production on glycerol grown cells. A preferred nucleotide sequence for overexpression of a glycerol uptake protein is therefore a nucleotide sequence encoding a glycerol uptake protein that is capable of rescuing salt stress-associated phenotype of a S. cerevisiae gup1Δ mutant by complementation as described by Neves et al. (2004, supra). Such complementing orthologues of S. cerevisiae GUP1 include nucleotide sequences encoding amino acid sequences having at least 60, 68, 72, 75, 80, 85, 90, 95, 98, 99% identity with the amino acid sequence of SEQ ID NO: 10 and may be obtained from yeast species belonging to the genera of Saccharomyces, Zygosaccharomyces, Kluyveromyces, Candida, Pichia, Hansenula, Kloeckera, Schwanniomyces, and Yarrowia.

A glycerol channel is herein understood as a member of the MIP family of channel proteins reviewed by Reiter et al. (1993, CRC Crit. Rev. Biochem. Mol. Biol., 28: 235-257), which channel proteins comprise a 250-280 amino acid transmembrane domain consisting of six membrane-spanning domains and have at least 30, 35, 40, 45, 50, 60, 70, 80, 90, 95, 98 or 99% amino acid identity, or at least 55, 60, 65, 70, 80, 90, 95, 98 or 99% amino acid similarity with the amino acid sequence between amino acids 250 and 530 of SEQ ID NO: 12, the S. cerevisiae FPS1 aquaglyceroporin. Nucleotide sequences that may be used for overexpression of a glycerol channel in the cells of the invention include nucleotide sequences encoding the yeast aquaglyceroporin FPS1 gene from e.g. S. cerevisiae (Van Aelst et al., 1991, EMBO J. 10:2095-2104) and orthologues thereof from other yeasts including Kluyveromyces lactis, Kluyveromyces marxianus and Zygosaccharomyces rouxii as e.g. described by Neves et al. (2004, supra). However, the use of bacterial or plant glycerol channels is not excluded as e.g. Luyten et al. (1995, EMBO J. 14:1360-1371) have shown that the E. coli glycerol facilitator, having only 30% sequence identity with the amino acid sequence between amino acids 250 and 530 of the S. cerevisiae FPS1 aquaglyceroporin, can complement glycerol uptake in a S. cerevisiae fps1Δ mutant. The nucleotide sequence encoding the glycerol channel may be endogenous to the cell or may be a glycerol channel that is heterologous to the cell. In a preferred embodiment a codon-optimised (see above) nucleotide sequence encoding the glycerol channel is overexpressed, such as e.g. a codon optimised nucleotide sequence encoding the aquaglyceroporin of SEQ ID NO: 12.

For overexpression of the nucleotide sequence encoding the glycerol uptake protein and/or the glycerol channel protein, the nucleotide sequence (to be overexpressed) is placed in an expression construct wherein it is operably linked to suitable expression regulatory regions/sequences to ensure overexpression of the glycerol uptake protein and/or the glycerol channel protein upon transformation of the expression construct into the host cell of the invention (see above). Suitable promoters for (over) expression of the nucleotide sequence coding for the glycerol uptake protein and/or the glycerol channel protein include promoters that are preferably insensitive to catabolite (glucose) repression, that are active under anaerobic conditions and/or that preferably do not require xylose or arabinose for induction. Examples of such promoters are given above. In the cells of the invention, a glycerol uptake protein and/or a glycerol channel protein to be overexpressed are preferably overexpressed by at least a factor 1.1, 1.2, 1.5, 2, 5, 10 or 20 as compared to a strain which is genetically identical except for the genetic modification causing the overexpression. Preferably, the glycerol uptake protein and/or the glycerol channel protein are overexpressed under anaerobic conditions by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity (specific activity in the cell), the steady state level of the enzyme's protein as well as to the steady state level of the transcript coding for the enzyme in the cell.

In a preferred embodiment of the host cell of the invention, the expression of the glycerol channel protein as defined above is reduced or inactivated. A genetic modification reducing or inactivating the expression of the glycerol channel protein may be useful to reduce or prevent transport of glycerol out of the cell. Preferably, the reduction or inactivation of the expression of the glycerol channel protein is combined with overexpression of the nucleotide sequence encoding the glycerol uptake protein as defined above.

In a further embodiment, the host cell of the invention further comprises a genetic modification that increases the specific acetyl-CoA synthetase activity in the cell, preferably under anaerobic conditions as this activity is rate-limiting under these conditions. Acetyl-CoA synthetase or acetate-CoA ligase (EC 6.2.1.1) is herein understood as an enzyme that catalyzes the formation of a new chemical bond between acetate and coenzyme A (CoA). Preferably the genetic modification causes overexpression of a acetyl-CoA synthetase, e.g. by overexpression of a nucleotide sequence encoding a acetyl-CoA synthetase. The nucleotide sequence encoding the acetyl-CoA synthetase may be endogenous to the cell or may be a acetyl-CoA synthetase that is heterologous to the cell. Nucleotide sequences that may be used for overexpression of acetyl-CoA synthetase in the cells of the invention are e.g. the acetyl-CoA synthetase genes from S. cerevisiae (ACS1 and ACS2) as e.g. described by de Jong-Gubbels et al. (1998, FEMS Microbiol Lett. 165: 15-20). Preferably, the nucleotide sequence encoding the acetyl-CoA synthetase comprises an amino acid sequence with at least 45, 50, 60, 65, 70, 75, 80, 85, 90, 95, 98, 99% amino acid sequence identity with at least one of SEQ ID NO's: 13 and 14.

In one embodiment, the nucleotide sequence that is overexpressed encodes an acetyl-CoA synthetase with a high affinity for acetate. Use of an acetyl-CoA synthetase with a high affinity for acetate is preferred for conditions under which there is a relatively low concentration of acetic acid in the culture medium, e.g. no more than 2 g acetic acid/L culture medium. An acetyl-CoA synthetase with a high affinity tier acetate is herein defined as an acetyl-CoA synthetase with a higher affinity for acetate than the acetyl-CoA synthetase encoded by the S. cerevisiae ACS2. Preferably, an acetyl-CoA synthetase with a high affinity tier acetate has a Km for acetate of no more than 10, 5, 2, 1, 0.5, 0.2 or 0.1 mM, such e.g. the acetyl-CoA synthetase encoded by the S. cerevisiae ACS1 gene. More preferably a codon-optimised (see above) nucleotide sequence encoding the amino acid sequence of SEQ ID NO: 13 is overexpressed.

In another embodiment, the nucleotide sequence that is overexpressed encodes an acetyl-CoA synthetase with a high maximum rate ($v_{max}$). Use of an acetyl-CoA synthetase with a high maximum rate is preferred for condition under which there is a relatively high concentration of acetic acid in the culture medium, e.g. at least 2, 3, 4 or 5 g acetic acid/L culture medium. An acetyl-CoA synthetase with a high maximum rate is herein defined as an acetyl-CoA synthetase with a higher maximum rate than the acetyl-CoA synthetase encoded by the S. cerevisiae ACS1. Preferably, the acetyl-CoA synthetase with a high maximum rate is the acetyl-CoA synthetase encoded by the S. cerevisiae ACS2 gene. More preferably a codon-optimised (see above) nucleotide sequence encoding the amino acid sequence of SEQ ID NO: 14 is overexpressed.

For overexpression of the nucleotide sequence encoding the acetyl-CoA synthetase (to be overexpressed) is placed in an expression construct wherein it is operably linked to suitable expression regulatory regions/sequences to ensure overexpression of the acetyl-CoA synthetase enzyme upon transformation of the expression construct into the host cell of the invention (see above). Suitable promoters for (over) expression of the nucleotide sequence coding for the enzyme having acetyl-CoA synthetase activity include promoters that are preferably insensitive to catabolite (glucose) repression, that are active under anaerobic conditions and/or that preferably do not require xylose or arabinose for induction. Examples of such promoters are given above. In the cells of the invention, an acetyl-CoA synthetase to be overexpressed is overexpressed by at least a factor 1.1, 1.2, 1.5, 2, 5, 10 or 20 as compared to a strain which is genetically identical except for the genetic modification causing the overexpression. Preferably, the acetyl-CoA synthetase is overexpressed under anaerobic conditions by at least a factor 2, 5, 10, 20, 50, or 100 as compared to a strain which is genetically identical except for the genetic modification causing the overexpression. It is to be understood that these levels of overexpression may apply to the steady state level of the enzyme's activity (specific activity), the steady state level of the enzyme's protein as well as to the steady state level of the transcript coding for the enzyme.

In a further embodiment, the host cell of the invention further comprises a genetic modification that reduces specific $NAD^+$-dependent glycerol 3-phosphate dehydrogenase activity in the cell. Glycerol 3-phosphate dehydrogenase or glycerolphosphate dehydrogenase (EC 1.1.1.8) katalyses the reduction of dihydroxyacetone phosphate to sn-glycerol 3-phosphate while oxidising NADH to $NAD^+$. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the overexpression, preferably under anaerobic conditions.

Preferably, glycerolphosphate dehydrogenase activity is reduced in the host cell by one or more genetic modifications that reduce the expression of or inactivates a gene encoding an glycerolphosphate dehydrogenase. Preferably, the genetic modifications reduce or inactivate the expression of each endogenous copy of the gene encoding a specific glycerolphosphate dehydrogenase in the cell's genome. A given cell may comprise multiple copies of the gene encoding a specific glycerolphosphate dehydrogenase with one and the same amino acid sequence as a result of di-, poly- or aneu-ploidy. In such instances preferably the expression of each copy of the specific gene that encodes the glycerolphosphate dehydrogenase is reduced or inactivated. Alternatively, a cell may contain several different (iso)enzymes with glycerolphosphate dehydrogenase activity that differ in amino acid sequence and that are each encoded by a different gene. In such instances, in some embodiments of the invention it is preferred that only certain types of the isoenzymes are reduced or inactivated while other types remain unaffected (see below). Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of glycerolphosphate dehydrogenase activity in the host cell.

A preferred gene encoding a glycerolphosphate dehydrogenase whose activity is to be reduced or inactivated in the cell of the invention is the *S. cerevisiae* GPD2 gene as described by Eriksson et al. (1995, Mol. Microbiol. 17: 95-107), encoding the amino acid sequence of SEQ ID NO: 15 and orthologues thereof in other species. Therefore a gene encoding a glycerolphosphate dehydrogenase whose activity is to be reduced or inactivated in the cell of the invention preferably is a gene encoding a glycerolphosphate dehydrogenase having an amino acid sequence with at least 70, 75, 80, 85, 90, 95, 98 or 99% sequence identity to SEQ ID NO: 15.

In a preferred embodiment of the invention, the host cell of the invention comprises a functional high-osmolarity glycerol response pathway. Preferably therefore, only the activity of the gene(s) encoding a glycerolphosphate dehydrogenase having an amino acid sequence with at least 70% sequence identity to SEQ ID NO: 15 are reduced or inactivated, while at least one endogenous gene encoding a glycerolphosphate dehydrogenase having an amino acid sequence with at least 70, 75, 80, 85, 90, 95, 98 or 99% sequence identity to SEQ ID NO: 16 is functional. SEQ ID NO: 16 depicts the amino acid sequence encoded by the *S. cerevisiae* GPD1 gene as described by Albertyn et al. (1994, Mol. Cell. Biol. 14: 4135-4144), which has 69% amino acid identity with the *S. cerevisiae* GPD2 glycerolphosphate dehydrogenase. The *S. cerevisiae* GPD1 gene is the stress-induced glycerolphosphate dehydrogenase of *S. cerevisiae*, which is important for growth under osmotic stress as may occur under industrial fermentations conditions. Its expression is inter alia regulated by the high-osmolarity glycerol response pathway. It is therefore advantageous that a host cell of the invention has at least one functional copy of a endogenous gene encoding a glycerolphosphate dehydrogenase having an amino acid sequence with at least 70, 75, 80, 85, 90, 95, 98 or 99% sequence identity to SEQ ID NO: 16.

Notwithstanding the above, the inventors have now surprisingly found that inactivation of the *S. cerevisiae* GPD1 glycerolphosphate dehydrogenase has a more advantageous effect on the reduction of glycerol production and the increase of glycerol and acetate consumption as compared to inactivation of the *S. cerevisiae* GPD2 glycerolphosphate dehydrogenase. Therefore, in a more preferred embodiment, the host cell of the invention comprises a genetic modification that reduces or inactivates the expression of at least the gene(s) encoding a glycerolphosphate dehydrogenase having an amino acid sequence with at least 70, 75, 80, 85, 90, 95, 98 or 99% sequence identity to SEQ ID NO: 16 (GPD1).

In a further embodiment, the activity of all the genes in the host cell encoding a glycerolphosphate dehydrogenase is reduced or inactivated. In such cells preferably all copies of endogenous genes encoding a glycerolphosphate dehydrogenase having an amino acid sequence with at least 70, 75, 80, 85, 90, 95, 98 or 99% sequence identity to SEQ ID NO: 15 or 16 are inactivated or at least reduced in expression.

In another embodiment of the invention, the host cell is not a yeast cell comprising an exogenous gene coding for a enzyme with the ability to convert pyruvate and coenzyme-A into formate and acetyl-CoA. Preferably the host cell is not a yeast cell comprising a nucleotide sequence encoding a pyruvate formate lyase.

In yet another embodiment of the invention, the host cell is a host cell wherein the specific formate dehydrogenase activity is at least 81, 85, 90, 95, or 100% of the specific formate dehydrogenase activity in a strain of the host cell which is genetically identical except for a genetic modification selected from the group consisting of: a) (the introduction of) an exogenous gene coding for an enzyme with acetaldehyde dehydrogenase activity, which gene confers to the cell the ability to convert acetic acid into ethanol; b) (the introduction of) a bacterial gene coding for an enzyme with NAD$^+$-linked glycerol dehydrogenase activity; and c) any of the other genetic modifications described herein above. Thus, a preferred host cell of the invention is not a yeast cell comprising a genetic modification that reduces specific NAD$^+$-dependent formate dehydrogenase activity in the cell.

In a further preferred embodiment, the host cell of the invention has at least one of: a) the ability of isomerising xylose to xylulose; and, b) the ability to convert L-arabinose into D-xylulose 5-phosphate. For a) the cell preferably has a functional exogenous xylose isomerase gene, which gene confers to the cell the ability to isomerise xylose into xylulose. For b) the cell preferably has functional exogenous genes coding for a L-arabinose isomerase, a L-ribulokinase and a L-ribulose-5-phosphate 4-epimerase, which genes together confers to the cell the ability to isomerise convert L-arabinose into D-xylulose 5-phosphate.

Fungal host cells having the ability of isomerising xylose to xylulose as e.g. described in WO 03/0624430 and in WO 06/009434. The ability of isomerising xylose to xylulose is preferably conferred to the cell by transformation with a nucleic acid construct comprising a nucleotide sequence encoding a xylose isomerase. Preferably the cell thus acquires the ability to directly isomerise xylose into xylulose. More preferably the cell thus acquires the ability to grow aerobically and/or anaerobically on xylose as sole energy and/or carbon source though direct isomerisation of xylose into xylulose (and further metabolism of xylulose). It is herein understood that the direct isomerisation of xylose into xylulose occurs in a single reaction catalysed by a xylose isomerase, as opposed to the two step conversion of xylose into xylulose via a xylitol intermediate as catalysed by xylose reductase and xylitol dehydrogenase, respectively.

Several xylose isomerases (and their amino acid and coding nucleotide sequences) that may be successfully used to confer to the cell of the invention the ability to directly isomerise xylose into xylulose have been described in the art. These include the xylose isomerases of *Piromyces* sp. and of other anaerobic fungi that belongs to the families *Neocallimastix, Caecomyces, Piromyces* or *Ruminomyces* (WO 03/0624430), *Cyllamyces aberensis* (US 20060234364), *Orpinomyces* (Madhavan et al., 2008, DOI 10.1007/s00253-008-1794-6), the xylose isomerase of the bacterial genus *Bacteroides*, including e.g. *B. thetaiotaomicron* (WO 06/009434), *B. fragilis*, and *B. uniformis* (WO 09/109633), the xylose isomerase of the anaerobic bacterium *Clostridium phytofermentans* (Brat et al., 2009, Apple Environ. Microbiol. 75: 2304-2311), and the xylose isomerases of *Clostridium difficile, Ciona intestinales* and *Fusobacterium mortiferum*.

Fungal host cells having the ability to convert L-arabinose into D-xylulose 5-phosphate as e.g. described in Wisselink et al. (2007, AEM Accepts, published online ahead of print on 1 Jun. 2007; Appl. Environ. Microbiol. doi:10.1128/AEM.00177-07) and in EP 1 499 708. The ability of to converting L-arabinose into D-xylulose 5-phosphate is preferably conferred to the cell by transformation with a nucleic acid constructs) comprising nucleotide sequences encoding a) an arabinose isomerase; b) a ribulokinase, preferably a L-ribulokinase a xylose isomerase; and c) a ribulose-5-P-4-epimerase, preferably a L-ribulose-5-P-4-epimerase. Preferably, in the cells of the invention, the ability to convert L-arabinose into D-xylulose 5-phosphate is the ability to convert L-arabinose into D-xylulose 5-phosphate through the subsequent reactions of 1) isomerisation of arabinose into ribulose; 2) phosphorylation of ribulose to ribulose 5-phosphate; and, 3) epimerisation of ribulose 5-phosphate into D-xylulose 5-phosphate. Suitable nucleotide sequences encoding arabinose isomerases, a ribulokinases and ribulose-5-P-4-epimerases may be obtained from *Bacillus subtilis, Escherichia coli* (see e.g. EP 1 499 708), *Lactobacilli*, e.g. *Lactobacillus plantarum* (see e.g. Wisselink et al. supra), or species of *Clavibacter, Arthrobacter* and *Gramella*, of which preferably *Clavibacter michiganensis, Arthrobacter aurescens* and *Gramella forsetii* (see WO2009/011591).

The transformed host cell of the invention further preferably comprises xyluose kinase activity so that xylulose isomerised from xylose may be metabolised to pyruvate. Preferably, the cell contains endogenous xylulose kinase activity. More preferably, a cell of the invention comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the cell or may be a xylulose kinase that is heterologous to the cell. A nucleotide sequence that may be used for overexpression of xylulose kinase in the cells of the invention is e.g. the xylulose kinase gene from *S. cerevisiae* (XKS1) as described by Deng and Ho (1990, Appl. Biochem. Biotechnol. 24-25: 193-199). Another preferred xylulose kinase is a xylose kinase that is related to the xylulose kinase from *Piromyces* (xylB; see WO 03/0624430). This *Piromyces* xylulose kinase is actually more related to prokaryotic kinase than to all of the known eukaryotic kinases such as the yeast kinase. The eukaryotic xylulose kinases have been indicated as non-specific sugar kinases, which have a broad substrate range that includes xylulose. In contrast, the prokaryotic xylulose kinases, to which the *Piromyces* kinase is most closely related, have been indicated to be more specific kinases for xylulose, i.e. having a narrower substrate range. In the cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

A cell of the invention further preferably comprises a genetic modification that increases the flux of the pentose phosphate pathway as described in WO 06/009434. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured as described in WO 06/009434.

Genetic modifications that increase the flux of the pentose phosphate pathway may be introduced in the cells of the invention in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred cell of the invention, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate 3-epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate 3-epimerase; or at least the enzymes ribulose-5-phosphate isomerase and transketolase; or at least the enzymes ribulose-5-phosphate isomerase and transaldolase; or at least the enzymes ribulose-5-phosphate 3-epimerase and transketolase; or at least the enzymes ribulose-5-phosphate 3-epimerase and transaldolase; or at least the enzymes transketolase and transaldolase; or at least the enzymes ribulose-5-phosphate 3-epimerase, transketolase and transaldolase; or at least the enzymes ribulose-5-phosphate isomerase, transketolase and transaldolase; or at least the enzymes ribulose-5-phosphate isomerase, ribulose-5-phosphate 3-epimerase, and transaldolase; or at least the enzymes ribulose-5-phosphate isomerase, ribulose-5-phosphate 3-epimerase, and transketolase. In one embodiment of the invention each of the enzymes ribulose-5-phosphate isomerase, ribulose-5-phosphate 3-epimerase, transketolase and transaldolase are overexpressed in the cell of the invention. Preferred is a cell in which the genetic modification comprises at least overexpression of the enzyme transaldolase. More preferred is a cell in which the genetic modification comprises at least overexpression of both the enzymes transketolase and transaldolase as such a host cell is already capable of anaerobic growth on xylose. In fact, under some conditions we have found that cells overexpressing only the transketolase and the transaldolase already have the same anaerobic growth rate on xylose as do cells that overexpress all four of the enzymes, i.e. the ribulose-5-phosphate isomerase, ribulose-5-phosphate 3-epimerase, transketolase and transaldolase. Moreover, cells of the invention overexpressing both of the enzymes ribulose-5-phosphate isomerase and ribulose-5-phosphate 3-epimerase are preferred over cells overexpressing only the isomerase or only the 3-epimerase as overexpression of only one of these enzymes may produce metabolic imbalances.

There are various means available in the art for overexpression of enzymes in the cells of the invention. In particular, an enzyme may be overexpressed by increasing the copynumber of the gene coding for the enzyme in the cell, e.g. by integrating additional copies of the gene in the cell's genome, by expressing the gene from an episomal multicopy expression vector or by introducing a episomal expression vector that comprises multiple copies of the gene. The coding sequence used for overexpression of the enzymes preferably is homologous to the host cell of the invention. However, coding sequences that are heterologous to the host cell of the invention may likewise be applied.

Alternatively overexpression of enzymes in the cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the cell of the invention. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence, preferably under conditions where xylose or xylose and glucose are available as carbon sources, more preferably as major carbon sources (i.e. more than 50% of the available carbon source consists of xylose or xylose and glucose), most preferably as sole carbon sources.

A further preferred cell of the invention comprises a genetic modification that reduces unspecific aldose reductase activity in the cell. Preferably, unspecific aldose reductase activity is reduced in the host cell by one or more genetic modifications that reduce the expression of or inactivates a gene encoding an unspecific aldose reductase. Preferably, the genetic modifications reduce or inactivate the expression of each endogenous copy of a gene encoding an unspecific aldose reductase that is capable of reducing an aldopentose, including, xylose, xylulose and arabinose, in the cell's genome. A given cell may comprise multiple copies of genes encoding unspecific aldose reductases as a result of di-, poly- or aneu-ploidy, and/or a cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell. A nucleotide sequence encoding an aldose reductase whose activity is to be reduced in the cell of the invention and amino acid sequences of such aldose reductases are described in WO 06/009434 and include e.g. the (unspecific) aldose reductase genes of *S. cerevisiae* GRE3 gene (Träff et al., 2001, Appl. Environm. Microbiol. 67: 5668-5674) and orthologues thereof in other species.

A further preferred transformed host cell according to the invention may comprises further genetic modifications that result in one or more of the characteristics selected from the group consisting of (a) increased transport of xylose and/or arabinose into the cell; (b) decreased sensitivity to catabolite repression; (c) increased tolerance to ethanol, osmolarity or organic acids; and, (d) reduced production of by-products. By-products are understood to mean carbon-containing molecules other than the desired fermentation product and include e.g. xylitol, arabinitol, glycerol and/or acetic acid. Any genetic modification described herein may be introduced by classical mutagenesis and screening and/or selection for the desired mutant, or simply by screening and/or selection for the spontaneous mutants with the desired characteristics. Alternatively, the genetic modifications may consist of overexpression of endogenous genes and/or the inactivation of endogenous genes. Genes the overexpression of which is desired for increased transport of arabinose and/or xylose into the cell are preferably chosen form genes encoding a hexose or pentose transporter. In *S. cerevisiae* and other yeasts these genes include HXT1, HXT2, HXT4, HXT5, HXT7 and GAL2, of which HXT7, HXT5 and GAL2 are most preferred (see Sedlack and Ho, Yeast 2004; 21: 671-684). Another preferred transporter for expression in yeast is the glucose transporter encoded by the *P. stipitis* SUT1 gene (Katahira et al., 2008, Enzyme Microb. Technol. 43: 115-119). Similarly orthologues of these transporter genes in other species may be overexpressed. Other genes that may be overexpressed in the cells of the invention include genes coding for glycolytic enzymes and/or ethanologenic enzymes such as alcohol dehydrogenases. Preferred endogenous genes for inactivation include hexose kinase genes e.g. the *S. cerevisiae* HXK2 gene (see Diderich et al., 2001, Appl. Environ. Microbiol, 67: 1587-1593); the *S. cerevisiae* MIG1 or MIG2 genes; genes coding for enzymes involved in glycerol metabolism such as the *S. cerevisiae* glycerol-phosphate dehydrogenase 1 and/or 2 genes; or (hybridising) orthologues of these genes in other species. Other preferred further modifications of host cells for xylose fermentation are described in van Maris et al. (2006, Antonie van Leeuwenhoek 90:391-418), WO2006/009434, WO2005/023998, WO2005/111214, and WO2005/091733. Any of the genetic modifications of the cells of the invention as described herein are, in as far as possible, preferably introduced or modified by self cloning genetic modification.

A preferred host cell according to the invention has the ability to grow on at least one of xylose and arabinose as carbon/energy source, preferably as sole carbon/energy source, and preferably under anaerobic conditions, i.e. conditions as defined herein below for anaerobic fermentation process. Preferably, when grown on xylose as carbon/energy source the host cell produces essentially no xylitol, e.g. the xylitol produced is below the detection limit or e.g. less than 5, 2, 1, 0.5, or 0.3% of the carbon consumed on a molar basis. Preferably, when grown on arabinose as carbon/energy source, the cell produces essentially no arabinitol, e.g. the arabinitol produced is below the detection limit or e.g. less than 5, 2, 1, 0.5, or 0.3% of the carbon consumed on a molar basis.

A preferred host cell of the invention has the ability to grow on a combination of: a) at least one of a hexose and a pentose; b) acetic acid; and c) glycerol at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. Therefore, preferably the host cell has the ability to grow on at least one of xylose and arabinose as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions. More preferably, the host cell has the ability to grow on a mixture of a hexose (e.g. glucose) and at least one of xylose and arabinose (in a 1:1 weight ratio) as sole carbon/energy source at a rate of at least 0.01, 0.02, 0.05, 0.1, 0.2, 0.25 or 0.3 $h^{-1}$ under aerobic conditions, or, more preferably, at a rate of at least 0.005, 0.01, 0.02, 0.05, 0.08, 0.1, 0.12, 0.15 or 0.2 $h^{-1}$ under anaerobic conditions.

In a one aspect, the invention relates to the use of a yeast cell according to the invention for the preparation of a fermentation product selected from the group consisting of ethanol, lactic acid, 3-hydroxy-propionic acid, acrylic acid, 1,3-propane-diol, butanols and isoprenoid-derived products.

In another aspect the invention relates to a process for producing a fermentation product selected from the group consisting of ethanol, lactic acid, 3-hydroxy-propionic acid, acrylic acid, 1,3-propane-diol, butanols (1-butanol, 2-butanol, isobutanol) and isoprenoid-derived products. The process preferably comprises the step of: a) fermenting a medium with a yeast cell, whereby the medium contains or is fed with: a) a source of at least one of a hexose and a pentose; b) a source of acetic acid; and, c) a source of glycerol and whereby the yeast cell ferments acetic acid, glycerol and at least one of the hexose and pentose to ethanol. The yeast cell preferably is a (host) cell as herein defined above. The process preferably comprise a further step wherein the fermentation product is recovered. The process may be a batch process, a fed-batch process or a continuous process as are well known in the art. In the process of the invention, the source of glycerol may be a any carbon source that has a more reduced state than glucose. A carbon source having a more reduced state than glucose is understood as a carbon source of which the average reduction state per C-mol (of the compounds therein) is higher than the reduction state per C-mol of glucose. Examples of carbon sources having a more reduced state than glucose include e.g. alkanols such as propanol and butanol; polyols such as 1,3-propane-diol, butandiol, glycerol, mannitol and xylitol.

In a preferred process the source of hexose comprises or consists of glucose. Preferably the source pentose comprises or consists of at least one of xylose and arabinose. Preferably, the medium fermented by the cells of the invention comprises or is fed with (fractions of) hydrolysed biomass comprising at least one at least one of a hexose and a pentose such as glucose, xylose and/or arabinose. The (fractions of) hydrolysed biomass comprising the hexoses and pentose will usually also comprise acetic acid (or a salt thereof). An example of hydrolysed biomass to be fermented in the processes of the invention is e.g. hydrolysed lignocellulosic biomass. Lignocellulosic biomass is herein understood as plant biomass that is composed of cellulose, hemicellulose, and lignin. The carbohydrate polymers (cellulose and hemicelluloses) are tightly bound to the lignin Examples of lignocellulosic biomass to be hydrolysed for use in the present invention include agricultural residues (including corn stover and sugarcane bagasse), wood residues (including sawmill and paper mill discards and (municipal) paper waste. Methods for hydrolysis of biomass such as lignocelluloses are known in the art per se and include e.g. acids, such as sulphuric acid and enzymes such as cellulases and hemicellulases.

In the process of the invention, the sources of xylose, glucose and arabinose may be xylose, glucose and arabinose as such (i.e. as monomeric sugars) or they may be in the form of any carbohydrate oligo- or polymer comprising xylose, glucose and/or arabinose units, such as e.g. lignocellulose, arabinans, xylans, cellulose, starch and the like. For release of xylose, glucose and/or arabinose units from such carbohydrates, appropriate carbohydrases (such as arabinases, xylanases, glucanases, amylases, cellulases, glucanases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases preferably during the fermentation. This, in turn, will prevent repression of systems required for metabolism and transport of non-glucose sugars such as xylose and arabinose. In a preferred process the modified host cell ferments both the glucose and at least one of xylose and arabinose, preferably simultaneously in which case preferably a modified host cell is used which is insensitive to glucose repression to prevent diauxic growth. In addition to a source of at least one of xylose and arabinose (and glucose) as carbon source, the fermentation medium will further comprise the appropriate ingredient required for growth of the modified host cell. Compositions of fermentation media for growth of eukaryotic microorganisms such as yeasts are well known in the art.

In the process of the invention, the medium further preferably comprises and/or is fed a source of glycerol. Glycerol for use in the process of the present invention may advantageously be glycerol that is generated as a by-product in biodiesel production from transesterification reactions using vegetable oils or animal fats and an alcohol.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating NAD$^+$. Thus, in a preferred anaerobic fermentation process pyruvate is used as an electron (and hydrogen acceptor) and is reduced to fermentation products such as ethanol, as well as non-ethanol fermentation products such as lactic acid, 3-hydroxy-propionic acid, acrylic acid, 1,3-propane-diol, butanols (1-butanol, 2-butanol, isobutanol) isoprenoid-derived products. Anaerobic processes of the invention are preferred over aerobic processes because anaerobic processes do not require investments and energy for aeration and in addition, anaerobic processes produce higher product yields than aerobic processes.

Alternatively, the fermentation process of the invention may be run under aerobic oxygen-limited conditions. Preferably, in an aerobic process under oxygen-limited conditions, the rate of oxygen consumption is at least 5.5, more preferably at least 6 and even more preferably at least 7 mmol/L/h. In a preferred aerobic oxygen-limited fermentation process of the invention, the yeast cell of the invention consumes less than 30, 20, 18, 15, 12, 10, 8 or 5% of the amount of oxygen on a C-molar basis related to the carbon source consumed during the conversion of the carbon source into the fermentation product. The conversion coefficient of oxygen consumed over substrate utilised on a C-molar basis ($C_{OS}$) is herein understood to mean mol $O_2$ used per C-mol carbon source consumed. Thus, a process of the invention can be carried out under strict anaerobic conditions (i.e. $C_{OS}$=0.0), or the process of the invention can be carried out under aerobic, preferably oxygen-limited conditions wherein the $C_{OS}$ is preferably less than 0.3, 0.2, 0.18, 0.15, 0.12, 0.1, 0.08, or 0.05.

The fermentation process is preferably run at a temperature that is optimal for the modified cells of the invention. Thus, for most yeasts cells, the fermentation process is performed at a temperature which is less than 42° C., preferably less than 38° C. For yeast cells, the fermentation process is preferably performed at a temperature which is lower than 35, 33, 30 or 28° C. and at a temperature which is higher than 20, 22, or 25° C.

A preferred fermentation process according to the invention is a process for the production of ethanol, whereby the process comprises the step of fermenting a medium with a yeast cell, whereby the medium contains or is fed with: a) a source of at least one of a hexose and a pentose; b) a source of acetic acid; and, c) a source of glycerol, whereby the yeast cell ferments acetic acid, glycerol and at least one of the hexose and pentose to ethanol, and optionally, b) recovery of the ethanol. The fermentation medium may further be performed as described above. In the process the volumetric ethanol productivity is preferably at least 0.5, 1.0, 1.5, 2.0, 2.5, 3.0, 5.0 or 10.0 g ethanol per litre per hour. The ethanol yield on xylose and/or glucose and/or arabinose and/or acetate and/or glycerol in the process preferably is at least 50, 60, 70, 80, 90, 95 or 98%. The ethanol yield is herein defined as a percentage of the theoretical maximum yield, which, for xylose, glucose and arabinose is 0.51 g. ethanol per g. xylose, glucose or arabinose. For glycerol the theoretical maximum yield is 0.50 g. ethanol per g. glycerol and for acetic acid the theoretical maximum yield is 0.77 g. ethanol per g. acetic acid.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

1. Enzyme Activity Assays

Figure 1:
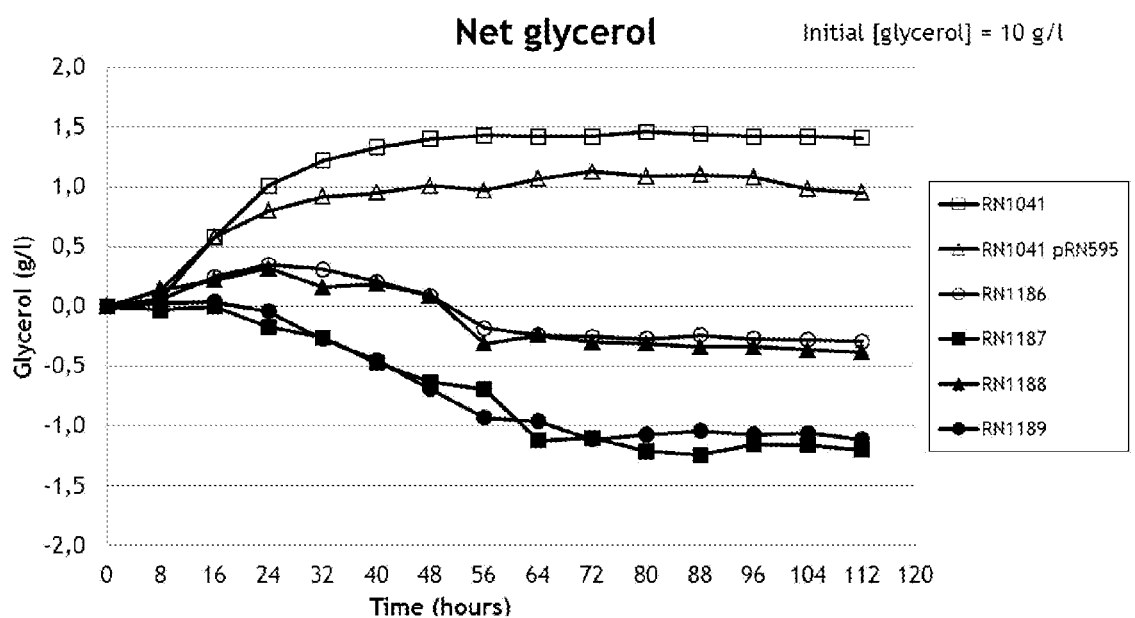
FIG. 1. The evolution of the net glycerol levels (g/l) (i.e. production minus consumption) over time (hours) is shown for *S. cerevisiae* strains RN1041, RN1041+pRN595, RN1186, RN1187, RN1188 and RN1189.

Cell extracts for activity assays were prepared from exponentially growing aerobic or anaerobic batch cultures and analysed for protein content as described by Abbot et al., (2009, Appl. Environ. Microbiol. 75: 2320-2325).

NAD$^+$-dependent acetaldehyde dehydrogenase (EC 1.2.1.10) activity was measured at 30° C. by monitoring the oxidation of NADH at 340 nm. The reaction mixture (total volume 1 ml) contained 50 mM potassium phosphate buffer (pH 7.5), 0.15 mM NADH and cell extract. The reaction was started by addition of 0.5 mM acetyl-Coenzyme A.

For glycerol 3-phosphate dehydrogenase (EC 1.1.1.8) activity determination, cell extracts were prepared as described above except that the phosphate buffer was replaced by triethanolamine buffer (10 mM, pH 5). Glycerol-3-phosphate dehydrogenase activities were assayed in cell extracts at 30° C. as described previously (Blomberg and Adler, 1989, J. Bacteria 171: 1087-1092.9). Reaction rates were proportional to the amounts of cell extract added.

Acetyl-CoA synthase (EC 6.2.1.1) activity was measured as described by Frenkel and Kitchens (1977, J. Biol., Chem. 252: 504-507) which is a modification of the method of Webster (Webster, 1969, Methods Enzymol. 13: 375-381). NADH formation measured is spectrophotometrically when the acetyl-CoA produced is coupled with citrate synthase and malate dehydrogenase reactions. The assay system contained 100 mM Tris-Cl (pH 7.6), 10 mM $MgCl_2$, 6 mM ATP, 5 mM malate, 1 mM $NAD^+$, 0.1 mM NADH, 2.5 mM dithreitol or 2-mercaptoethanol, 0.2 mM coenzyme A, 25 µg citrate synthase (80 units/mg), 20 µg malate dehydrogenase (1000 units/mg), and 10 mM acetate and the reaction was measured rate was measured at 340 nm and calculated from the extinction coefficient of NADH ($6.22 \times 10^6$ $cm^2$/mol).

The activity of glycerol dehydrogenase and dihydroxyacetone kinase are measured at 30° C. in cell extracts, essentially as previously described (Gonzalez et al., 2008, Metab. Eng. 10, 234-245). Enzyme activities of glycerol dehydrogenase and dihydroxyacetone kinase are reported as µmoles of substrate/min/mg of cell protein.

2. Strain Construction

All modifications start with the xylose and arabinose fermenting strain RN1008 his⁻. RN1008 his⁻, also referred to herein as RN1041, is a CEN.PK-based arabinose and xylose fermenting strain) with the genotype:

Mat a, ura3-52, leu2-112, his3::loxP, gre3::loxP, loxP-Ptpi::TAL1, loxP-Ptpi::RKI1, loxP-Ptpi-TKL1, loxP-Ptpi-RPE1, delta::-LEU2, delta:: Padh1XKS1Tcyc1-URA3-Ptpi-xylA-Tcyc1, delta:: LEU2-AAAaraABD.

Mat a=mating type a ura3-52, leu2-112, his3::loxP mutations in the genes ura3, leu2 and his3, the ura3 is complemented by the xylA-XKS overexpression construct, leu2 is complemented by the AraABD overexpression construct. his3 could be used for selection of additional plasmids, RN1041 needs histidine in the medium for growth.

gre3::loxP=deletion of the gre3 gene encoding xylose reductase, loxP site is left after marker removal.

loxP-Ptpi . . . =overexpression of het pentose phosphate pathway, loxP site upstream of constitutive promoter is left after marker removal delta::=integration of the construct after recombination on the long terminal repeats of the Ty1 reterotransposon.

AAAaraABD=codon optimized *Arthrobacter aurescens* araA, araB and araD genes (see WO2009/011591)

Deletion Constructs for GPD1 and GPD2

The deletion of GPD1 in RN1041 produces strain RN1197. The deletion of GPD2 in RN1041 produces strain RN1198. In this strain subsequently gpd1 is deleted to produce strain RN1199. In these strains plasmids were introduced for overexpression of the ACS genes (RN1200 to RN1207, Table 4) and further genes as indicated in Table 4.

gpd1::hphMX

Primers gpd1uf, gpd1ur, gpd1df and gpd1dr are used for amplification of genomic sequences fragments upstream and downstream of the GPD1 gene for its inactivation. Both the up- and downstream GPD1 fragments are cloned into a topo blunt vector (InVitrogen) to yield pGPD1up and pGPD1down, respectively.

```
gpd1uf:
                                     (SEQ ID NO: 41)
AAGCTTGGTACCCGCCTTGCTTCTCTCCCC gpd1ur:
                                     (SEQ ID NO: 42)
TCTAGACCAGCATTCAAGTGGCCGGA gpd1df:
                                     (SEQ ID NO: 43)
CGTACGAGTTGTTGAATGGCCAATCCGCT gpd1dr:
                                     (SEQ ID NO: 44)
CCATGGTACCGAGTGGTGTTGTAACCACCCT gpd1cf:
                                     (SEQ ID NO: 45)
ACCAATACGTAAACGGGGCG gpd1cr:
                                     (SEQ ID NO: 46)
AATACACCCATACATACGGACGC
```

Plasmid pRN593 (SEQ ID NO: 40) is constructed by ligation of the fragment cut with HindIII and XbaI from pGPD1up to the hphMX fragment cut with SpeI and BsrGI (plasmid collection C5YeastCompany) and the fragment cut with BsiWI and NcoI from pGPD1down into the HindIII and NcoI cut topo T/A vector (Invitrogen). Plasmid pRN593 is cut with KpnI to obtain deletion fragment for disrupting the genomic copy (SEQ ID NO: 17). The mixture of linear fragments is used for transformation of yeast. Transformants are selected for hygromycin resistance. Correct integration results in deletion of the GPD1 open reading frame. The integration is PCR verified with the primers gpd1cf and gpd1cr.

gpd2::natMX

Primers GPD2uf, GPD2ur, GPD2df and GPD2dr are used for amplification of genomic sequences fragments upstream and downstream of the GPD2 gene for its inactivation. A 407 bp upstream PCR fragment with an AflII site at the 3'-end (derived from the GPD2 sequence) and a BglII site at the 5'-end (for isolation of the deletion construct) is amplified using GPD2uf, GPD2ur and cloned in pCR2.1 (topo T/A, Invitrogen).

```
GPD2uf:
                                     (SEQ ID NO: 32)
GGTACCAGATCTTTTGCGGCGAGGTGCCG

GPD2ur:
                                     (SEQ ID NO: 33)
TCTAGACTTAAGGAATGTGTATCTTGTTAATCTTCTGACAGC
```

A 417 bp downstream PCR fragment with a XhoI site at the 5'-end and a BglII site at the 3'-end is amplified using GPD2df and GPD2dr.

```
GPD2df:
                                     (SEQ ID NO: 34)
CTCGAGATAGTCTACAACAACGTCCGCA

GPD2dr:
                                     (SEQ ID NO: 35)
CCATGGAGATCTGCAGTGAAAAAGCTCGAAGAAACAGCT
```

For the final construction the plasmid containing the upstream fragment is cut with AflII and Kpn, the downstream fragment is cut with XhoI en NcoI and the natMX marker (plasmid collection Royal Nedalco) is cut with AflII en XhoI and the fragments are ligated to produce plasmid pRN594 (SEQ ID NO: 36). pRN594 is cut with BglII prior to yeast transformation. Transformants are selected for nourseotricin resistance. Correct integration is verified by PCR.

Cloning Method for Overexpression of the
Saccharomyces cerevisiae ACS1 and ACS2 Genes The ACS1 open reading frame is PCR amplified with the primers acs1f and acs1r.

```
acs1f:
                                            (SEQ ID NO: 47)
TTAAGCTTAAAATGTCGCCCTCTGCCGT acs1r:
                                            (SEQ ID NO: 48)
AAGCGCGCTACAACTTGACCGAATCAATTAGATGTCTAACAATGCCAGGG
```

This PCR fragment is cut with the restriction enzymes HindIII and BssHII and ligated to the SalI and HindIII cut TEF1 promoter fragment (collection C5YeastCompany) and the BssHII and BsiWI cut ADH1 terminator fragment (collection C5YeastCompany). This combined fragment is PCRed with promoter and terminator specific primers and cloned into the topo Blunt vector (InVitrogen) to give pACS1.

The ACS2 open reading frame is PCR amplified with the primers acs2f and acs2r.

```
acs2f:
                                            (SEQ ID NO: 49)
AACTGCAGAAAATGACAATCAAGGAACATAAAGTAGTTTATGAAGCTCA acs2r:
                                            (SEQ ID NO: 50)
ACGTCGACTATTTCTTTTTTTGAGAGAAAAATTGGTTCTCTACAGCAGA
```

This PCR fragment is cut with the restriction enzymes PstI and SalI and ligated to the SpeI and PstI cut PGK1 promoter fragment (collection C5YeastCompany) and the XhoI and BsiWI cut PGI1 terminator fragment (collection C5YeastCompany). This combined fragment is PCRed with promoter and terminator specific primers and cloned into the topo Blunt vector (InVitrogen) to give plasmid pACS2.

The ACS1 overexpression construct is cut from pACS1 with the restriction enzymes SalI and BsiWI, the ACS2 overexpression construct is cut from pACS2 with the restriction enzymes SpeI and BsiWI, the KanMX marker is cut with BspEI and XbaI (plasmid collection C5YeastCompany). These fragments are ligated to the plasmid pRS306+2 mu ORI (plasmid collection C5Yeast company) cut with BspEI and XhoI to give the final plasmid pRN753 (SEQ ID NO: 51). This plasmid is used to transform yeast strains as indicated in Table 4 and transformants are selected on G418 resistance. Overexpression is verified by qPCR. An alternative plasmid that may be used for overexpression of ACS1 and ACS 2 is pRN500 (SEQ ID NO: 20).

Expression of E. coli adhE, E. histolytica ADH2 or
E. coli mphF

The PGK1 promoter (SpeI-PstI) and the ADH1 terminator sequence (AflII-NotI) are added to the codon optimized synthetic fragments and cloned into pRS303 with 2µ ori cut with SpeI and NotI and the expression construct is cloned in this vector. Expression is qPRC verified. Codon optimized sequences for E. coli mphF (SEQ ID NO: 2), E. coli adhE (SEQ ID NO: 4) and E. histolytica ADH2 (SEQ ID NO: 6) are as indicated in the sequence listing.

For expression of the E. coli mhpF gene, a yeast PGK1 promoter fragment (SpeI-PstI) and an ADH1 terminator fragment (AflII-NotI) (both from the Nedalco plasmid collection) were ligated onto the codon-optimized synthetic fragment encoding the E. coli mhpF (SEQ ID NO: 2). pRS 303 with 2µ ori (=pRN347, Royal Nedalco plasmid collection) was cut with SpeI and NotI and the mhpF expression construct was cloned into this vector to produce pRN558 (SEQ ID NO: 29).

For expression of the E. coli adhE gene, a codon optimized synthetic fragment encoding the E. coli adhE (SEQ ID NO: 4) is cut with XbaI and AflII and ligated into pRN558 cut with XbaI and AflII (replacing the E. coli mhpF gene in pRN558) to produce pRN595 (SEQ ID NO: 30).

For expression of the Entamoeba histolytica adh2, a codon optimized synthetic fragment encoding the E. histolytica adh2 (SEQ ID NO: 6) is cut with XbaI and AflII and ligated into pRN558 cut with XbaI and AflII (replacing the E. coli mhpF gene in pRN558) to produce pRN596 (SEQ ID NO: 31).

pRN595 is used for further construction of pRN957 and pRN977 (see below). It is clear that pRN558 and pRN596 can be used in the same way, thereby replacing expression of E. coli adhE with E. coli mhpF or E. histolytica adh2, respectively.

Expression of E. coli gldA

The construct for expression in yeast of the E. coli gldA was made by ligating a yeast ACT1 promoter fragment (cut with the restriction enzymes SpeI and PstI), a synthetic ORF (SEQ ID NO: 21), encoding the E. coli gldA, (cut with PstI en BssHII) and a yeast CYC1 terminator fragment (cut with BssHII and BsiWI) together into pCRII blunt (Invitrogen) to yield pRNgldA (SEQ ID NO: 28).

DAK1 Overexpression

PCR is performed on genomic DNA of S. cerevisiae with primers introducing a XbaI site 5' of the ATG and a SalI site 3' of the TAA to produce the fragment of SEQ ID NO: 22. A DNA fragment comprising the S. cerevisiae TPI1 promoter is ligated upstream of the DAK1 ORF and DNA fragment comprising the S. cerevisiae PGI1 terminator fragment is ligated downstream of the DAK1 ORF to produce pRNDAK (SEQ ID NO: 38).

Expression of C. freundii dhaK

The construct for expression in yeast of the Citrobacter freundii dhaK was made by ligating the yeast TPI1 promoter fragment (cut with the restriction enzymes XhoI and XbaI), a synthetic ORF (SEQ ID NO: 26), encoding the C. freundii dhaK, (cut with XbaI and SalI) and a yeast PGI1 terminator fragment (cut with XhoI and BsiWI) together into pCRII blunt (Invitrogen) to yield pRNdhaK (SEQ ID NO: 27).

GUP1 Overexpression

PCR is performed on genomic DNA of S. cerevisiae with primers introducing a HindIII site 5' of the ATG and a BamHI site 3' of the TAA to produce the fragment of SEQ ID NO: 23. A DNA fragment comprising the *S. cerevisiae* TDH3 promoter is ligated upstream of the GUP1 ORF and DNA fragment comprising the *S. cerevisiae* CYC1 terminator fragment is ligated downstream of the GUP1 ORF.

FPS1 Overexpression

PCR is performed on genomic DNA of *S. cerevisiae* with primers introducing a NsiI site 5' of the ATG and a BamII site 3' of the TAA to produce the fragment of SEQ ID NO: 24. A DNA fragment comprising the *S. cerevisiae* ADH1 (medium) promoter is ligated upstream of the FSP1 ORF and DNA fragment comprising the *S. cerevisiae* CYC1 terminator fragment is ligated downstream of the FSP1 ORF.

Construction of pRN347 and Yeast Strain RN1151 pRN347 is constructed by cloning the 2μ origin of replication (that was PCR-amplified from pYES2) in pRS303 (with HIS3 gene for complementation). RN1041 is transformed with the plasmid pRN347 to produce strain RN1151.

Strains Expressing *E. coli* gldA and *C. freundii* dhaK or Overexpressing DAK1

For construction of pRN957, the *E. coli* gldA expression construct is cut from plasmid pRNgldA with the restriction enzymes SpeI and BsiWI. The *C. freundii* dhaK expression construct is cut from plasmid pRNdhaK with the restriction enzymes BsiWI and XhoI. These fragments are ligated into plasmid pRN595 cut with the restriction enzymes SpeI and SalI to yield pRN957 (SEQ ID NO: 37).

For construction of pRN977, the *E. coli* gldA expression construct is cut from plasmid pRNgldA with the restriction enzymes SpeI and BsiWI. The DAK1 expression construct is cut from the plasmid pRNDAK with the restriction enzymes BsiWI and XhoI. These fragments are ligated to plasmid pRN595 cut with the restriction enzymes SpeI and SalI to yield pRN977 (SEQ ID NO: 39).

Plasmids pRN957 and pRN977 are used to transform RN1041, RN1197, RN1198 and RN1199 to yield yeast strains as indicated in Table 4.

Tables 4A and B: Overview of Constructed Strains

TABLE 4B

| | ACS1/2 | gpd1Δ | gpd2Δ | adhE, gldA, DAK1 | adhE, gldA, dhaK | HIS3 |
|---|---|---|---|---|---|---|
| RN1041 | | | | | | |
| RN1151 | | | | | | pRN347 |
| RN1197 | | pRN593 | | | | pRN347 |
| RN1198 | | | | | | pRN347 |
| RN1199 | | pRN593 | pRN594 | | | pRN347 |
| RN1200 | pRN753 | | | pRN957 | | |
| RN1201 | pRN753 | | | | pRN977 | |
| RN1202 | pRN753 | pRN593 | | pRN957 | | |
| RN1203 | pRN753 | pRN593 | | | pRN977 | |
| RN1204 | pRN753 | | pRN594 | pRN957 | | |
| RN1205 | pRN753 | | pRN594 | | pRN977 | |
| RN1206 | pRN753 | pRN593 | pRN594 | pRN957 | | |
| RN1207 | pRN753 | pRN593 | pRN594 | | pRN977 | |

3. Anoxic Fermentations in Sterile Yeast Extract Peptone Medium with Constructed Strains in the Presence and Absence of Glycerol and or Acetic Acid The proof of principle of concomitant reduction of acetic acid and oxidation of glycerol was obtained by using a medium containing 1% yeast extract and 1% peptone. Experiments were run in chemostat culture (1 litre working volume) at D=0.05 h$^{-1}$ and the pH was kept at 5.5 by automatic addition of either KOH or $H_2SO_4$. Glucose (50 g/l) and xylose (50 g/l) were added as carbon and energy source to the yeast extract peptone medium. For these experiments demonstrating the proof of principle, no arabinose was included. Where relevant, acetic acid was added to the yeast extract peptone medium at 4 g/l and glycerol at 10 g/l. The temperature was kept at 32° C.

Precultures of strains are prepared by inoculating a frozen glycerol stock culture of the yeast in an YP (Yeast extract at 1% w/v and Peptone at 1% w/v) medium with addition of each of the sugars glucose and xylose (each at 1% w/v) at 32° C. and pH 5.5. After 24 h incubation under oxic conditions in shake flasks, 50 ml of this culture is used to inoculate the chemostat cultures.

At steady state of the fermentations (5 volume changes), a sample was taken for analysis of sugar (glucose and xylose) consumption, consumption of acetic acid, and metabolite (ethanol and glycerol). Ethanol, glycerol and acetic acid concentrations are monitored by HPLC analysis. To determine the sugar consumption, glucose and xylose are determined by HPAEC (Dionex) analysis.

TABLE 4A

| Strain marker | ACS1 kanMX | ACS2 kanMX | GPD1 hphMX | GPD2 natMX | adhE HIS3 | DAK1 HIS3 | Cf dhaK HIS3 | Ec gldA HIS3 | HIS3 |
|---|---|---|---|---|---|---|---|---|---|
| RN1041 | wt | wt | wt | wt | absent | wt | absent | absent | del |
| RN1151 | wt | wt | wt | wt | absent | wt | absent | absent | wt |
| RN1197 | wt | wt | del | wt | absent | wt | absent | absent | wt |
| RN1198 | wt | wt | wt | del | absent | wt | absent | absent | wt |
| RN1199 | wt | wt | del | del | absent | wt | absent | absent | wt |
| RN1200 | up | up | wt | wt | expression | up | absent | expression | |
| RN1201 | up | up | wt | wt | expression | wt | expression | expression | |
| RN1202 | up | up | del | wt | expression | up | absent | expression | |
| RN1203 | up | up | del | wt | expression | wt | expression | expression | |
| RN1204 | up | up | wt | del | expression | up | absent | expression | |
| RN1205 | up | up | wt | del | expression | wt | expression | expression | |
| RN1206 | up | up | del | del | expression | up | absent | expression | |
| RN1207 | up | up | del | del | expression | wt | expression | expression | |

Strain RN1151 is not able to reach a steady state situation in the medium containing 4 g/l acetic acid either in the presence or absence of glycerol. If no acetic acid is added to the medium, the organism at steady state consumed all glucose and xylose (less than 1 g/l remaining). No glycerol was consumed, but instead it was produced.

Strains RN1200 and RN1201 are similarly tested on media with acetic acid and either with or without glycerol added. These strains perform distinctly different from strain RN1151. In the glycerol-containing medium the sugars glucose and xylose are consumed almost to completion (less than 1 g/l remaining). Acetic acid levels decreases to 0.5 g/l and the concentrations of glycerol at the end of the fermentation is 3 g/l in all three instances. The amounts of ethanol produced by strain RN1200 and RN1201 ranged between 43 and 47 g/l in various experiments. In the medium not containing glycerol, but containing 4 g/l acetic acid, no stable steady state was obtained. The strains cannot grow under these conditions. From these results we conclude that expression of the E. coli gldA and adhE genes in combination with upregulation of DAK1 or expression of C. freundii dhaK, has a profound effect on the performance of the strains. In the presence of glycerol, they are able to consume glycerol and acetic acid, Strains RN1202 to RN1207 are similar to strains RN1200 and RN1201 except for the fact that GPD1 and/or GPD2 genes have been deleted. In the medium containing 4 g/l acetic acid, the sugars glucose and xylose are consumed almost to completion (less than 1 g/l remaining) if glycerol is added to the medium as is the case for strains RN1200 and RN1201. If no glycerol is added, no steady state is obtained.

4. Anoxic Fermentations with the Constructed Strains in Acetic Acid Comprising Lignocellulosic Hydrolysates in the Presence or Absence of Glycerol The corn fiber hydrolysate contains: glucose (38 g/l), xylose (28 g/l), arabinose (12 g/l) and acetic acid (4 g/l). It had been prepared by treating corn fibers at 160 C and at pH 3.0 during 20 minutes, followed by enzymatic hydrolysis by cellulases and hemicellulases. Acetic acid was added to this hydrolysate resulting in a total concentration of acetic acid in the hydrolysate of 10 g/l. The pH of this hydrolysate enriched in acetic acid was restored to pH=4.5 by KOH addition. Yeast extract was added to this hydrolysate to reach a final concentration of 5 g/l. In all subsequent experiments, this enriched hydrolysate was employed. The pH during fermentations was kept at 6.5 by automatic addition of either KOH or $H_2SO_4$.

Precultures of strains are prepared by inoculating a frozen glycerol stock culture of the yeast in an YP (Yeast extract at 1% w/v and Peptone at 1% w/v) medium with addition of each of the sugars glucose, xylose and arabinose (each at 1% w/v) at 32° C. and pH 5.5. After 24 h incubation under oxic conditions in shake flasks, 50 ml of this culture is used to inoculate the fermenter cultures. Fermentations are performed in a fed-batch fermentation setup. Hydrolysate (either with or without glycerol added at 50 g/l) is pumped into the fermenter. If no glycerol was added, then 40 ml of water was added. During the first 6 hours, the flow rate for hydrolysate is set at a rate of 5 ml per hour. During the next 6 hours, the flow rate is set at 10 ml per hour. Subsequently, for another 43 hours, the flow rate is set at 20 ml per hour. The total volume at the end of the fermentation reaches 1000 ml. These anoxic fed-batch fermentations are performed at about pH=4.5 with gentle stirring at 100 rpm. The temperature during the fermentations is set at 32° C. To minimize infection, the hydrolysates are heated for 10 min at 105° C. prior to fermentations and the antibiotic kanamycine with at final concentration of 50 µg/ml is added.

At the end of the fermentations after 55 h, a sample was taken for analysis of sugar (glucose, xylose and arabinose) consumption, consumption of acetic acid, and metabolite (ethanol and glycerol). Ethanol, glycerol and acetic acid concentrations over time are monitored by HPLC analysis. To determine the sugar consumption, glucose, xylose, and arabinose are determined by HPAEC (Dionex) analysis.

Strain RN1151 (=RN1041 complemented with HIS3) is tested on hydrolysate either with or without glycerol added. In both instances, the concentration of glucose at the end of the fermentation run (55 h) is 35 g/l whereas xylose and arabinose remain at their initial concentrations of 28 and 12 g/l, respectively. The amounts of ethanol produced are 2 g/l and acetic acid is present at 9.5 g/l. No glycerol consumption is detected in the glycerol-containing hydrolysate. The fermentation of the sugars halts during the course of the fed-batch operation because of increasing levels of acetic acid. Initially, no acetic acid is present in the fermenter, but while pumping the hydrolysate that contained toxic levels of acetic acid, the concentration quickly reaches toxic levels.

Strains RN1200 and RN1201 are similarly tested on hydrolysate either with or without glycerol added. These strains perform distinctly different from strain RN1151. In the glycerol-containing hydrolysate, the sugars glucose, xylose and arabinose are consumed to completion. Acetic acid levels decreases to 2 g/l and the concentrations of glycerol at the end of the fermentation is 29.5 g/l in all three instances. The amounts of ethanol produced by strains RN1200 and RN1201 are 51.7, and 52.2 g/l, respectively. In the hydrolysate that did not contain glycerol, considerably less sugar is consumed. Xylose and arabinose levels are unchanged at 28 and 12 g/l, respectively. Glucose is consumed but to a limited extent only. At the end of the fermentation, the remaining concentration is 32 g/l in all three instances with ethanol reaching a concentration of 3 g/l. The concentration of acetic acid drops to 9.1 g/l at the end of the fermentation whereas some glycerol is produced (less than 0.5 g/l). From these results we conclude that expression of the E. coli gldA and adhE genes in combination with upregulation of DAK1 or expression of C. freundii dhaK, has a profound effect on the performance of the strains. In the presence of glycerol, they are able to consume glycerol and acetic acid, and produce additional ethanol (as compared to strain RN1151). In the absence of glycerol, the strains consume some acetic acid. But during the fermentation, the acetic acid level rises to toxic levels.

Strains RN1202 to RN1207 are similar to strains RN1200 and RN1201 except for the fact that GPD1 and/or GPD2 genes have been deleted. In the glycerol-containing hydrolysate, the sugars glucose, xylose and arabinose are consumed to completion as was the case for strain RN1200. Acetic acid levels similarly decrease to approximately 2 g/l and the concentrations of glycerol at the end of the fermentation is 28 g/l in these three instances. The amounts of ethanol produced for strains RN1202, RN1203, RN1204, RN1205, RN1206 and RN1207 are 51.6, 52.9, 52.1, 52.5, 53.1 and 52.3 g/l, respectively. In the hydrolysate that not containing glycerol, considerably less sugar is consumed. Xylose and arabinose levels are unchanged at 28 and 12 g/l, respectively. Glucose is consumed but to a limited extent only. At the end of the fermentation, the remaining concentration in the non-glycerol hydrolysate for glucose is 31 g/l in all three instances with ethanol reaching a concentration of 3 g/l. The concentration of acetic acid drops to 9.1 g/l at the end of the fermentation whereas some glycerol is produced (less than 0.5 g/l). From these results we conclude that deleting GPD1 and/or GPD2 genes along with the other modifications in RN1202, RN1203, RN1204, RN1205, RN1206 and RN1207 result in strains that can perform the desired reactions.

Materials and Methods for Examples 5-8

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Media

The media used in the experiments was either YEP-medium (10 g/l yeast extract, 20 g/l peptone) or solid YNB-medium (6.7 g/l yeast nitrogen base, 15 g/l agar), supplemented with sugars as indicated in the examples. For solid YEP medium, 15 g/l agar was added to the liquid medium prior to sterilization.

In the AFM experiments, Mineral Medium was used. The composition of Mineral Medium has been described by Verduyn et al. (Yeast (1992), Volume 8, 501-517) and was supplemented with 2.325 g/l urea and sugars as indicated in the examples.

Transformation of Yeast Cells

Yeast transformation was done according to the method described by Schiestl and Gietz (Current Genetics (1989), Volume 16, 339-346).

Colony PCR

Genomic DNA was extracted from single yeast colonies for PCR according to the method described by Lõoke et al. (BioTechniques (2011), Volume 50, 325-328).

AFM Procedure

The Alcohol Fermentation Monitor (AFM; Halotec, Veenendaal, the Netherlands) is a robust and user-friendly laboratory parallel bioreactor that allows for accurate comparisons of carbon conversion rates and yields for six simultaneous anaerobic fermentations.

The starting culture of the AFM experiment contained 50 mg of yeast (dry weight). To determine this, a calibration curve was made of the RN1041 strain of biomass vs. OD700. This calibration curve was used in the experiment to determine the volume of cell culture needed for 50 mg of yeast (dry weight).

Prior to the start of the AFM experiment, precultures were grown as indicated in the examples. For each strain the $OD_{700}$ was measured and 50 mg of yeast (dry weight) was inoculated in 400 ml Mineral Medium (Verduyn et al. (Yeast (1992), Volume 8, 501-517), supplemented with 2,325 g/l urea and sugars as indicated in the examples.

Glycerodehydrogenase Activity Assay

The method for the determination of the glycerodehydrogenase activity assay was adopted from Lin and Magasanik (1960) J Biol Chem. 235:1820-1823.

TABLE 5

| Assay conditions | |
|---|---|
| 1.0M Carbonate/bicarbonate buffer pH 10 | 800 µl |
| 1.0M ammoniumsulfate | 33 µl |
| 0.1M NAD+ | 33 µl |
| Cell Free Extract | 5 µl |

Cell free extract was prepared by harvesting cells by centrifugation. Cells were harvested in the exponential phase. The cell pellet was washed once with 1 M carbonate/bicarbonate buffer (pH 10) and a cell free extract was prepared in the same by the addition of glass beads and vortexing at maximum speed for 1 minute intervals until the cells were disrupted. The latter was checked microscopically.

Shake Flask Experiments

Anaerobic shake flask experiments were performed as indicated in the examples. Typical experiments use 100 ml Erlenmeyer flasks with 25 ml of medium. In order to ensure anaerobic conditions, the flask was closed with a waterlock.

For each time point, a separate shake flask was inoculated, thereby omitting aeration during sampling.

Strains

The parent strain used in the experiments described in examples 5 through 8 is RN1041.

RN1041 has been described in WO 2012067510. This strain has the following genotype:

MAT a, ura3-52, leu2-112, his3::loxP, gre3::loxP, loxP-pTPI1::TAL1, loxP-pTPI1::RKI1, loxP-pTPI1-TKL1, loxP-pTPI1-RPE1, delta::pADH1-XKS1-tCYC1-LEU2, delta::URA3-pTPI1-xylA-tCYC1

MAT a=mating type a ura3-52, leu2-112, HIS3::loxP mutations in the URA3, LEU2 and HIS3 genes respectively. The ura3-52 mutation is complemented by the URA3 gene on the xylA overexpression construct; the leu2-112 mutation is complemented by the LEU2 gene on the XKS1 overexpression construct. The deletion of the HIS3-gene causes a histidine auxotrophy. For this reason, RN1041 needs histidine in the medium for growth.

gre3::loxP is a deletion of the GRE3 gene, encoding aldose reductase. The loxP site is left behind in the genome after marker removal.

loxP-pTPI1 designates the overexpression of genes of, in the experiments described herein, the non-oxidative pentose phosphate pathway by replacement of the native promoter by the promoter of the TPI1 gene. The loxP site upstream of the strong, constitutive TPI1 promoter remains in the genome after marker removal (Kuyper et al, FEMS Yeast Research 5 (2005) 925-934).

delta:: means chromosomal integration of the construct after recombination on the long terminal repeats of the Ty1 retrotransposon.

Example 5

Construction of Strains

The following strains were constructed:

TABLE 6 strains constructed

| | |
|---|---|
| RN1041 | Parent strain (see above) |
| RN1067 | RN1041 gpd1::hphMX |
| RN1068 | RN1041 gpd2::natMX |
| RN1069 | RN1041 gpd1::hphMX gpd2::natMX |
| RN1186 | RN1041 + pRN977 |
| RN1187 | RN1067 + pRN977 |
| RN1188 | RN1068 + pRN977 |
| RN1189 | RN1069 + pRN977 |

The deletion of the GPD1-gene (gpd1) and/or the GPD2-gene (gpd2) was brought about as described in Example 2.

Strains RN1041, RN1067, RN1068 and RN1069 were transformed with plasmid pRN977. This plasmid contains the following features: the HIS3-gene for selection of transformants, the 2µ origin of replication, the ampicillin resistance marker for selection in E. coli, the adhE-gene from E. coli under control of the PGK1-promoter and the ADH1-terminator, the DAK1-gene from S. cerevisiae under control of the TPI1-promoter and the PGI1-terminator and the E. coli gldA-gene, under control of the ACT1-promoter and CYC1-terminator. All promoters and terminators are from S. cerevisiae. The sequence of plasmid pRN977 is set out in SEQ ID NO: 39.

After transformation of strains RN1041, RN1067, RN1068 and RN1069, single colony isolates were subjected to colony PCR analysis, in order to check the presence of plasmid pRN977. A representative colony of each transformation was selected for further experimentation. These selected strains are designated RN1186, RN1187, RN1188 and RN1189.

Similarly, transformants were generated with the following specifications:

TABLE 7 transformants

| | |
|---|---|
| RN1190 | RN1041 + pRN957 |
| RN1191 | RN1067 + pRN957 |
| RN1192 | RN1068 + pRN957 |
| RN1193 | RN1069 + pRN957 |

Plasmid pRN957 is similar to pRN977; however, the DAK1-gene from S. cerevisiae has been replaced by the dhaK-gene from Citrobacter freundii. The sequence of this plasmid, pRN957, is set out in SEQ ID NO: 37.

As a control strain, strain RN1041 was transformed with plasmid pRN595 (RN1041+pRN595). This plasmid, pRN595, is similar to pRN977; however, it lacks the gldA and DAK1 genes. The sequence of plasmid pRN595 is set out in SEQ ID NO: 30.

Example 6

Shake Flask Experiments

The performance of the constructed strains was tested in an anaerobic shake flask experiment. To this end, cells were pregrown in Mineral Medium (Verduyn) supplemented with glucose as carbon source. The cultures were incubated overnight in a rotary shaker at 280 rpm and 30° C.

An aliquot of the cells was taken from the overnight cultures for inoculation of the anaerobic cultures. The amount of cells was such, that the anaerobic culture had an initial optical density at 600 nm of approximately 0.1.

The carbon composition of the Mineral Medium: 2.5% glucose, 2.5% xylose, 1% glycerol and 2 g/l HAc. The pH was adjusted to pH 4.5. The shake flasks were closed with a waterlock in order to ensure anaerobic conditions. For each time point, a separate flask was inoculated.

The results of net glycerol increase or decrease, after 94 hours of fermentation, and the HAc consumption, are indicated in the table below.

TABLE 8

Glycerol and HAc consumption, and ethanol production values per strain

| Strain | Net Glycerol Increase (+) or Decrease (−) (in grams/liter) | HAc consumption (in grams/liter) | Ethanol titer (in grams per liter) |
|---|---|---|---|
| RN1041 | +1.47 | 0.24 | 23.28 |
| RN1186 | −1.20 | 0.99 | 25.32 |
| RN1187 | −1.52 | 0.99 | 23.76 |
| RN1188 | −0.80 | 0.97 | 25.01 |
| RN1189 | −0.86 | 0.89 | 24.85 |
| RN1190 | −0.47 | 0.71 | 24.38 |
| RN1191 | −0.80 | 0.93 | 24.77 |
| RN1192 | +0.93 | 0.29 | 23.60 |
| RN1193 | −0.84 | 0.92 | 24.93 |

The strain indicated in table 8 as RN1041 was transformed with plasmid pRS323, a standard cloning vector containing the HIS3-gene and a 2µ origin of replication, thereby complementing the histidine auxotrophy.

The results show:

RN1041 produces glycerol, which makes sense since both GPD1- and GPD2-genes are active and gldA and DAK1 are not overexpressed. Since adhE is not expressed in this strain, HAc consumption is low.

Strains RN1186 through RN1189 show glycerol and HAc consumption, resulting in an increased ethanol titer as compared to RN1041.

The experiments with the transformants RN1190, RN1191 and RN1193 show the same results, i.e. consumption of glycerol and acetate, however to a slightly lesser extent. Also here, the ethanol titer is higher as compared to RN1041. The result of strain RN1192 is an artefact, as later characterization showed that this strain had lost its plasmid pRN957.

Overexpression of either a homologous or heterologous dihydroxyacetone kinase, in combination with overexpression of gldA and adhE, results in a simultaneous consumption of acetate and glycerol under anaerobic conditions.

Example 7

AFM Experiments

The experiment described in Example 6 was repeated in a slightly different set-up, i.e. the AFM (Alcoholic Fermentation Monitor), which allows on-line carbondioxide determination, during the experiment.

The strains tested were RN1041, RN1041+pRN595, RN1186, RN1187, RN1188 and RN1189. The strain RN1041 was transformed with plasmid pRS323, a standard cloning vector containing the HIS3-gene and a 2μ origin of replication, thereby complementing the histidine auxotrophy.

The strains were pre-cultured overnight in Mineral Medium with 2% glucose as carbon source, in a rotary shaker at 280 rpm and 30° C.

The cells were harvested and an AFM experiment was started as described above.

Samples were taken at regular intervals and sugars, ethanol, glycerol and HAc were determined by HPLC.

Results are shown in the Table below.

TABLE 9

Glycerol and HAc consumption and ethanol production values per strain at time = 112 hours.

| Strain | Net glycerol increase (−) or decrease (+) (grams per litre) | HAc consumption (grams per litre) | Ethanol production (grams per litre) |
|---|---|---|---|
| RN1041 | +1.4 | 0.1 | 24.0 |
| RN1041 + pRN595 | +1.1 | 0.4 | 24.1 |
| RN1186 | −0.3 | 0.7 | 25.5 |
| RN1187 | −1.2 | 1.0 | 25.5 |
| RN1188 | −0.3 | 0.7 | 25.2 |
| RN1189 | −1.1 | 1.0 | 25.6 |

Figure 2:
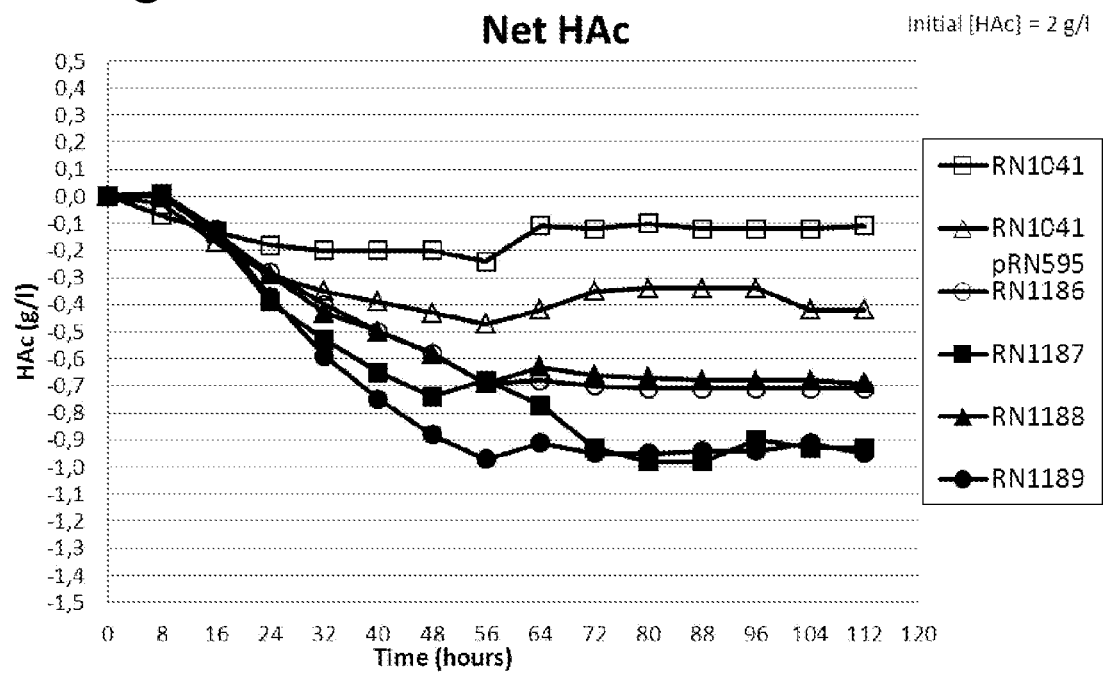
FIG. 2. The evolution of the net acetic acid levels (g/l) (i.e. production minus consumption) over time (hours) is shown for *S. cerevisiae* strains RN1041, RN1041+pRN595, RN1186, RN1187, RN1188 and RN1189.

The evolution of the glycerol and HAc levels in time are shown in FIGS. 1 and 2.

Strains RN1041 and RN1041+pRN595 are showing a net glycerol production. Strains RN1186 and RN1188 are initially showing glycerol production; however, after approximately 24 to 32 hours, glycerol consumption commenced and continued until in the end a net glycerol consumption was observed.

Strains RN1187 and RN1189 do not exhibit the initial glycerol production, as seen with RN1186 and RN1188. After 24 hours, glycerol consumption commences. The glycerol consumption is significantly higher in these strains as compared to RN1186 and RN1188. These results indicate that deletion of the GPD1-gene results in higher glycerol consumption than the deletion of the GPD2-gene.

Strain RN1041+pRN595 is showing a higher HAc consumption than the reference strain RN1041. RN1186 and RN1188 are exhibiting a higher HAc consumption than RN1041+pRN595. This result indicated that glycerol consumption enhanced HAc consumption. This effect is even stronger in strains RN1187 and RN1189.

Example 8

Glycerol Dehydrogenase Activity Assay

Cell free extracts (CFE) of strain RN1041 and RN1190 were prepared as described above. The glycerol dehydrogenase activity assay, adopted from the protocol of Lin and Magasanik (1960) J Biol Chem. 235:1820-1823, was performed. The results are shown in the Table below.

TABLE 10

| glycerol dehydrogenase activity assay | | |
|---|---|---|
| Sample | Cofactor | Increase in A340/min |
| RN1041 5 μl CFE | NAD+ | 0.00 |
| RN1190 5 μl CFE | NAD+ | 0.02 |
| RN1041 20 μl CFE | NAD+ | 0.00 |
| RN1190 20 μl CFE | NAD+ | 0.09 |
| RN1041 5 μl CFE | NADP+ | 0.00 |
| RN1190 5 μl CFE | NADP+ | 0.00 |
| RN1041 20 μl CFE | NADP+ | 0.00 |
| RN1190 20 μl CFE | NADP+ | 0.00 |

The strain indicated in table 10 as RN1041 was transformed with plasmid pRS323, a standard cloning vector containing the HIS3-gene and a 2μ origin of replication, thereby complementing the histidine auxotrophy.

These results indicate that: a) *E. coli* gldA, expressed in RN1190, is NADH+-dependent, and b) that increase in the amount of CFE resulted in a proportional increase of the conversion rate of NAD+, and hence of glycerol into dihydroxyacetone.

What is claimed:

1. A process for producing ethanol, wherein the process comprises the step of fermenting a medium with a *Saccharomyces* cell in the presence of:
   a) at least one of a hexose or a pentose sugar;
   b) acetic acid; and,
   c) glycerol,
wherein the *Saccharomyces* cell comprises an exogenous gene encoding an enzyme with acetaldehyde dehydrogenase activity, wherein the exogenous gene encoding the enzyme with acetaldehyde dehydrogenase activity comprises a nucleotide sequence encoding an amino acid sequence having:
   i) at least 80% amino acid sequence identity with SEQ ID NO:1,
   ii) at least 80% amino acid sequence identity with SEQ ID NO:3 and,
   iii) at least 80% amino acid sequence identity with SEQ ID NO:5;
wherein the *Saccharomyces* cell further comprises a bacterial gene encoding an enzyme with $NAD^+$-linked glycerol dehydrogenase activity, wherein the bacterial gene encoding the enzyme with $NAD^+$-linked glycerol dehydrogenase activity comprises a nucleotide sequence encoding an amino acid sequence with at least 80% amino acid sequence identity with SEQ ID NO:7;
wherein the yeast cell comprises a genetic modification that increases the specific activity of dihydroxyacetone kinase as compared to the specific activity of dihydroxyacetone kinase in an otherwise identical *Saccharomyces* cell not having the genetic modification and
wherein the yeast cell ferments acetic acid, glycerol and at least one of the hexose or pentose sugars to ethanol.

2. The process of claim 1, wherein the *Saccharomyces* cell further comprises at least one of:
   i) a functional exogenous xylose isomerase gene, which gene confers to the cell the ability to isomerise xylose into xylulose; and
   ii) functional exogenous genes encoding a L-arabinose isomerase, a L-ribulokinase and a L-ribulose-5-phosphate 4-epimerase, which genes together confers to the cell the ability to convert L-arabinose into D-xylulose 5-phosphate.

3. The process of claim 2, wherein the *Saccharomyces* cell comprises at least one further genetic modification selected from the group consisting of:
   a) increased xylulose kinase specific activity;
   b) increased flux of the pentose phosphate pathway
   c) reduced unspecific aldose reductase specific activity
   d) increased transport of at least one of xylose and arabinose into the host cell;
   e) decreased sensitivity to catabolite repression;
   f) increased tolerance to ethanol, osmolarity or organic acids; or
   g) reduced production of by-products
   wherein the increase or decrease is measured as compared to that in an otherwise identical *Saccharomyces* cell not having the at least one further genetic modification.

4. The process of claim 1, wherein the *Saccharomyces* cell further comprises a genetic modification that increases at least one of:
   i) acetyl-CoA synthetase activity;
   ii) transport of glycerol into the cell
wherein the increase is measured as compared to that in an otherwise identical *Saccharomyces* cell not having the genetic modification.

5. The process of claim 4, wherein the genetic modification increases the specific acetyl-CoA synthetase activity under anaerobic conditions as compared to the specific activity of acetyl-CoA synthetase in an otherwise identical *Saccharomyces* cell not having the genetic modification.

6. The process of claim 4, wherein the genetic modification is overexpression of a nucleotide sequence encoding an acetyl-CoA synthetase, wherein
   the nucleotide sequence encoding an acetyl-CoA synthetase encodes an acetyl-CoA synthetase with
      (a) a higher maximum rate than the acetyl-CoA synthetase encoded by the *S. cerevisiae* ACS1 gene, or
      (b) a higher affinity for acetate than the acetyl-CoA synthetase encoded by the *S. cerevisiae* ACS2 gene,
   and wherein the genetic modification that increases transport of glycerol into the cell is overexpression of a nucleotide sequence encoding at least one of a glycerol uptake protein and a glycerol channel.

7. The process of claim 6, wherein:
   (i) the nucleotide sequence encoding the glycerol uptake protein comprises a nucleotide sequence encoding an amino acid sequence with at least 50% amino acid sequence identity with at least one of SEQ ID Nibs: 10 and 11; and
   (b) the nucleotide sequence encoding the glycerol channel comprises a nucleotide sequence encoding an amino acid sequence with at least 30% amino acid sequence identity with the amino acid sequence between amino acids 250 and 530 of SEQ ID NO:12.

8. The process of claim 1, wherein the *Saccharomyces* yeast cell further comprises a genetic modification that reduces specific activity of $NAD^+$-dependent glycerol 3-phosphate dehydrogenase in the cell as compared to the specific activity of $NAD^+$-dependent glycerol 3-phosphate dehydrogenase in an otherwise identical *Saccharomyces* cell not having the genetic modification.

9. The process of claim 8, wherein the genetic modification that reduces the specific activity of $NAD^+$-dependent glycerol 3-phosphate dehydrogenase in the cell is a genetic modification that reduces or inactivates the expression of an endogenous gene encoding a glycerolphosphate dehydrogenase having an amino acid sequence with at least 70% sequence identity to SEQ ID NO:16.

10. The process of claim 1, wherein the genetic modification that increases the specific activity of dihydroxyacetone kinase, is overexpression of a nucleotide sequence encoding a dihydroxyacetone kinase.

11. The process of claim 10, wherein the nucleotide sequence encoding the dihydroxyacetone kinase comprises a nucleotide sequence encoding an amino acid sequence with at least 50% amino acid sequence identity with at least one of SEQ ID NOs: 8, 9, and 25.

12. The process of claim 1, wherein the medium comprises a lignocellulosic hydrolysate.

13. The process of claim 1, wherein the *Saccharomyces* cell ferments under anaerobic conditions.

* * * * *

SEQUENCE LISTING

<160> NUMBER OF SEQ ID NOS: 51

<210> SEQ ID NO 1
<211> LENGTH: 316
<212> TYPE: PRT
<213> ORGANISM: Escherichia coli

<400> SEQUENCE: 1

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315

<210> SEQ ID NO 2
<211> LENGTH: 968
<212> TYPE: DNA
<213> ORGANISM: Artificial
<220> FEATURE:
<223> OTHER INFORMATION: mhpF codon optimised

<400> SEQUENCE: 2
ctgcagtcta gatgtctaag agaaaggttg ctatcatcgg ttctggtaac atcggtactg      60
acttgatgat caagatccta agacacggtc aacacttgga aatggctgtt atggttggta     120
tcgacccaca atctgacggt ttggctagag ctagaagaat gggtgttgct accacccacg     180
aaggtgttat cggtttgatg aacatgccag aattcgctga catcgacatc gttttcgacg     240
ctacctctgc tggtgctcac gttaagaacg acgctgcttt gagagaagct aagccagaca     300
tcagattgat cgacttgacc ccagctgcta tcggtccata ctgtgttcca gttgttaact     360
tggaagctaa cgttgaccaa ttaaacgtta acatggttac ctgtggtggt caagctacca     420
tcccaatggt tgctgctgtt tcaagagttg ctagagttca ctacgctgaa atcatcgctt     480
ctatcgcttc taagtctgct ggtccaggta ccagagctaa catcgacgaa ttcaccgaaa     540
ccacctctag gctatcgaa gttgttggtg gtgctgctaa gggtaaggct atcatcgttt     600
tgaacccagc tgaaccacca ttgatgatga gagacaccgt ttacgttttg tctgacgaag     660
catctcaaga cgacatcgaa gcttcaatca acgaaatggc tgaagctgtt caagcatacg     720

```
ttccaggtta cagattgaag caaagagttc aattcgaagt tatcccacaa gacaagccag    780
ttaacttgcc aggtgttggt caattctctg gtttgaagac cgctgtttgg ttggaagttg    840
aaggtgctgc tcactacttg ccagcttacg ctggtaactt ggacattatg acctcttctg    900
ctttggctac cgctgaaaag atggctcaat ctttggctag aaaggctggt gaagctgctt    960
aagcgcgc                                                              968
```

<210> SEQ ID NO 3
<211> LENGTH: 891
<212> TYPE: PRT
<213> ORGANISM: Escherichia coli

<400> SEQUENCE: 3

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320
```

```
Gly Glu Val Thr Val Asp Glu Ser Glu Pro Phe Ala His Glu Lys
            325                 330                 335

Leu Ser Pro Thr Leu Ala Met Tyr Arg Ala Lys Asp Phe Glu Asp Ala
        340                 345                 350

Val Glu Lys Ala Glu Lys Leu Val Ala Met Gly Gly Ile Gly His Thr
            355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
```

```
            740                 745                 750
Ala Asn Asp Asn Pro Thr Lys Gln Thr Ala Phe Ser Gln Tyr Asp Arg
                755                 760                 765

Pro Gln Ala Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 4
<211> LENGTH: 2690
<212> TYPE: DNA
<213> ORGANISM: Artificial
<220> FEATURE:
<223> OTHER INFORMATION: synthetic codon optimimised adhE

<400> SEQUENCE: 4
tctagaaaat ggctgttacc aacgttgctg aattgaacgc tttggttgaa agggttaaga      60
aggctcaaag agaatacgct tctttcaccc aagaacaagt tgacaagatc ttcagagctg     120
ctgctttggc tgctgctgac gctagaatcc cattggctaa gatggctgtt gctgaatctg     180
gtatgggtat cgttgaagac aaggttatca agaaccactt cgcttctgaa tacatctaca     240
acgcttacaa ggacgaaaag acctgtggtg ttttgtcaga agacgacacc ttcggtacca     300
tcaccatcgc tgaaccaatc ggtatcatct gtggtatcgt tccaaccacc aacccaacct     360
ctaccgctat cttcaagtct ttgatctctt tgaagaccag aaacgctatc atcttctctc     420
cacacccaag agctaaagac gctaccaaca aggctgctga catcgttttg caagctgcta     480
tcgctgctgg tgctccaaag acttgatcg gttggatcga ccaaccatct gttgaattgt     540
ctaacgcttt gatgcaccac ccagacatca acttgatctt ggctaccggt ggtccaggta     600
tggttaaggc tgcttactct tctggtaagc cagctatcgg tgttggtgct ggtaacaccc     660
cagttgttat cgacgaaacc gctgacatca agagagctgt tgcttctgtt ttgatgtcta     720
agaccttcga caacggtgtt atctgtgctt ctgaacaatc tgttgttgtt gttgactctg     780
tttacgacgc tgttagagaa agattcgcta cccacggtgg ttacttgttg caaggtaagg     840
aattgaaggc tgttcaagac gttatcttga gaacggtgc tttgaacgct gctatcgttg     900
gtcaaccagc ttacaagatc gctgaattag ctggtttctc tgttccagaa aacaccaaga     960
tcttgatcgg tgaagttacc gttgttgacg aatctgaacc attcgctcac gaaaagttgt    1020
ctccaacctt ggctatgtac agagctaagg acttcgaaga cgctgttgaa aagctgaaa     1080 agttggttgc tatgggtggt attggtcaca ctcttgtttt gtacaccgac caagacaacc    1140
aaccagctag agtttcttac ttcggtcaaa agatgaagac cgctagaatc ttgatcaaca    1200
```

```
cccccagcttc tcaaggtggt atcggtgact tgtacaactt caagttggct ccatctttga   1260
ccttgggttg tggttcttgg ggtggtaact ctatctctga aaacgttggt ccaaagcact   1320
tgatcaacaa gaagaccgtt gctaagagag ctgaaaacat gttgtggcac aagttgccaa   1380
aatctatcta cttcagaaga ggttctttgc caatcgcttt ggacgaagtt atcaccgacg   1440
gtcacaagag agctttgatc gttaccgaca gattcttgtt caacaacggt tacgctgacc   1500
aaatcacctc tgttttgaag gctgctggtg ttgaaaccga agttttcttc gaagttgaag   1560
ctgacccaac cttgtctatc gttagaaagg gtgctgaatt ggctaactct ttcaagccag   1620
acgttatcat cgctttgggt ggtggttctc caatggacgc tgctaagatc atgtgggtta   1680
tgtacgaaca cccagaaacc cacttcgaag aattggcttt gagattcatg acatcagaa   1740 agagaatcta caagttccca agatgggtgt taaggctaa gatgatcgct gttaccacca   1800
cctctggtac cggttctgaa gttaccccat cgctgttgt taccgacgac gctaccggtc   1860
aaaagtaccc attggctgac tacgctttga ccccagacat ggctatcgtt gacgctaact   1920
tggttatgga catgccaaag tctttgtgtg ctttcggtgg tttggacgct gttacccacg   1980
ctatggaagc ttacgtttct gttttggctt ctgaattctc tgacggtcaa gctttgcaag   2040 cttttgaagtt gttgaaggaa tacttgccag cttcttacca cgaaggttct aagaacccag   2100
ttgctagaga aagagttcac tctgctgcta ccatcgctgg tatcgctttc gctaacgctt   2160
tcttgggtgt tgtcactct atggctcaca agttgggttc tcaattccac atcccacacg   2220
gtttggctaa cgctttgttg atctgtaacg ttatcagata caacgctaac gacaacccaa   2280
ccaagcaaac cgctttctct caatacgaca gaccacaagc tagaagaaga tacgctgaaa   2340
tcgctgacca cttgggtttg tctgctccag gtgacagaac cgctgcaaag atcgaaaagt   2400
tgttggcttg gttggaaacc ttgaaggctg aattgggtat cccaaagtct atcagagaag   2460
ctggtgttca agaagctgac ttcttggcta acgttgacaa gttgtctgaa gacgctttcg   2520
acgaccaatg taccggtgct aacccaagat acccattgat ctctgaattg aagcaaatct   2580
tgttggacac ctactacggt agagactacg ttgaaggtga aaccgctgct aagaaggaag   2640
ctgctccagc taaggctgaa aagaaggcta agaagtctgc ttagcttaag   2690
```

<210> SEQ ID NO 5
<211> LENGTH: 870
<212> TYPE: PRT
<213> ORGANISM: Entamoeba histolytica

<400> SEQUENCE: 5

```
Met Ser Thr Gln Gln Thr Met Thr Val Asp Glu His Ile Asn Gln Leu
1               5                   10                  15

Val Arg Lys Ala Gln Val Ala Leu Lys Glu Tyr Leu Lys Pro Glu Tyr
            20                  25                  30

Thr Gln Glu Lys Ile Asp Tyr Ile Val Lys Lys Ala Ser Val Ala Ala
        35                  40                  45

Leu Asp Gln His Cys Ala Leu Ala Ala Ala Val Glu Glu Thr Gly
    50                  55                  60

Arg Gly Ile Phe Glu Asp Lys Ala Thr Lys Asn Ile Phe Ala Cys Glu
65                  70                  75                  80

His Val Thr His Glu Met Arg His Ala Lys Thr Val Gly Ile Ile Asn
                85                  90                  95

Val Asp Pro Leu Tyr Gly Ile Thr Glu Ile Ala Glu Pro Val Gly Val
            100                 105                 110
```

-continued

```
Val Cys Gly Val Thr Pro Val Thr Asn Pro Thr Ser Thr Ala Ile Phe
            115                 120                 125
Lys Ser Leu Ile Ser Ile Lys Thr Arg Asn Pro Ile Val Phe Ser Phe
130                 135                 140
His Pro Ser Ala Leu Lys Cys Ser Ile Met Ala Ala Lys Ile Val Arg
145                 150                 155                 160
Asp Ala Ala Ile Ala Ala Gly Ala Pro Glu Asn Cys Ile Gln Trp Ile
                165                 170                 175
Glu Phe Gly Gly Ile Glu Ala Ser Asn Lys Leu Met Asn His Pro Gly
            180                 185                 190
Val Ala Thr Ile Leu Ala Thr Gly Gly Asn Ala Met Val Lys Ala Ala
        195                 200                 205
Tyr Ser Ser Gly Lys Pro Ala Leu Gly Val Gly Ala Gly Asn Val Pro
210                 215                 220
Thr Tyr Ile Glu Lys Thr Cys Asn Ile Lys Gln Ala Ala Asn Asp Val
225                 230                 235                 240
Val Met Ser Lys Ser Phe Asp Asn Gly Met Ile Cys Ala Ser Glu Gln
                245                 250                 255
Ala Ala Ile Ile Asp Lys Glu Ile Tyr Asp Gln Val Val Glu Glu Met
            260                 265                 270
Lys Thr Leu Gly Ala Tyr Phe Ile Asn Glu Glu Glu Lys Ala Lys Leu
        275                 280                 285
Glu Lys Phe Met Phe Gly Val Asn Ala Tyr Ser Ala Asp Val Asn Asn
290                 295                 300
Ala Arg Leu Asn Pro Lys Cys Pro Gly Met Ser Pro Gln Trp Phe Ala
305                 310                 315                 320
Glu Gln Val Gly Ile Lys Val Pro Glu Asp Cys Asn Ile Ile Cys Ala
            325                 330                 335
Val Cys Lys Glu Val Gly Pro Asn Glu Pro Leu Thr Arg Glu Lys Leu
        340                 345                 350
Ser Pro Val Leu Ala Ile Leu Lys Ala Glu Asn Thr Gln Asp Gly Ile
355                 360                 365
Asp Lys Ala Glu Ala Met Val Glu Phe Asn Gly Arg Gly His Ser Ala
370                 375                 380
Ala Ile His Ser Asn Asp Lys Ala Val Val Glu Lys Tyr Ala Leu Thr
385                 390                 395                 400
Met Lys Ala Cys Arg Ile Leu His Asn Thr Pro Ser Ser Gln Gly Gly
            405                 410                 415
Ile Gly Ser Ile Tyr Asn Tyr Ile Trp Pro Ser Phe Thr Leu Gly Cys
        420                 425                 430
Gly Ser Tyr Gly Gly Asn Ser Val Ser Ala Asn Val Thr Tyr His Asn
435                 440                 445
Leu Leu Asn Ile Lys Arg Leu Ala Asp Arg Arg Asn Asn Leu Gln Trp
450                 455                 460
Phe Arg Val Pro Pro Lys Ile Phe Phe Glu Pro His Ser Ile Arg Tyr
465                 470                 475                 480
Leu Ala Glu Leu Lys Glu Leu Ser Lys Ile Phe Ile Val Ser Asp Arg
            485                 490                 495
Met Met Tyr Lys Leu Gly Tyr Val Asp Arg Val Met Asp Val Leu Lys
        500                 505                 510
Arg Arg Ser Asn Glu Val Glu Ile Glu Ile Phe Ile Asp Val Glu Pro
515                 520                 525
Asp Pro Ser Ile Gln Thr Val Gln Lys Gly Leu Ala Val Met Asn Thr
```

Phe Gly Pro Asp Asn Ile Ile Ala Ile Gly Gly Ser Ala Met Asp
545                 550                 555                 560

Ala Ala Lys Ile Met Trp Leu Leu Tyr Glu His Pro Glu Ala Asp Phe
                565                 570                 575

Phe Ala Met Lys Gln Lys Phe Ile Asp Leu Arg Lys Arg Ala Phe Lys
                580                 585                 590

Phe Pro Thr Met Gly Lys Ala Arg Leu Ile Cys Ile Pro Thr Thr
            595                 600                 605

Ser Gly Thr Gly Ser Glu Val Thr Pro Phe Ala Val Ile Ser Asp His
        610                 615                 620

Glu Thr Gly Lys Lys Tyr Pro Leu Ala Asp Tyr Ser Leu Thr Pro Ser
625                 630                 635                 640

Val Ala Ile Val Asp Pro Met Phe Thr Met Ser Leu Pro Lys Arg Ala
                645                 650                 655

Ile Ala Asp Thr Gly Leu Asp Val Leu Val His Ala Thr Glu Ala Tyr
                660                 665                 670

Val Ser Val Met Ala Asn Glu Tyr Thr Asp Gly Leu Ala Arg Glu Ala
            675                 680                 685

Val Lys Leu Val Phe Glu Asn Leu Leu Lys Ser Tyr Asn Gly Asp Leu
            690                 695                 700

Glu Ala Arg Glu Lys Met His Asn Ala Ala Thr Ile Ala Gly Met Ala
705                 710                 715                 720

Phe Ala Ser Ala Phe Leu Gly Met Asp His Ser Met Ala His Lys Val
                725                 730                 735

Gly Ala Ala Phe His Leu Pro His Gly Arg Cys Val Ala Val Leu Leu
                740                 745                 750

Pro His Val Ile Arg Tyr Asn Gly Gln Lys Pro Arg Lys Leu Ala Met
            755                 760                 765

Trp Pro Lys Tyr Asn Phe Tyr Lys Ala Asp Gln Arg Tyr Met Glu Leu
            770                 775                 780

Ala Gln Met Val Gly Leu Lys Cys Asn Thr Pro Ala Glu Gly Val Glu
785                 790                 795                 800

Ala Phe Ala Lys Ala Cys Glu Glu Leu Met Lys Ala Thr Glu Thr Ile
                805                 810                 815

Thr Gly Phe Lys Lys Ala Asn Ile Asp Glu Ala Ala Trp Met Ser Lys
            820                 825                 830

Val Pro Glu Met Ala Leu Leu Ala Phe Glu Asp Gln Cys Ser Pro Ala
            835                 840                 845

Asn Pro Arg Val Pro Met Val Lys Asp Met Glu Lys Ile Leu Lys Ala
850                 855                 860

Ala Tyr Tyr Pro Ile Ala
865             870

<210> SEQ ID NO 6
<211> LENGTH: 2627
<212> TYPE: DNA
<213> ORGANISM: Artificial
<220> FEATURE:
<223> OTHER INFORMATION: synthetic codon optimised ADH2

<400> SEQUENCE: 6
tctagaaaat gtctacccaa caaaccatga ccgttgacga acacatcaac caattagtta      60
gaaaggctca agttgctttg aaggaatact tgaagccaga atacacccaa gaaaagatcg     120

```
actacatcgt taagaaggct tctgttgctg cttttggacca acactgtgct ttggctgctg    180
ctgctgttga agaaaccggt agaggtatct tcgaagacaa ggctaccaag aacatcttcg    240
cttgtgaaca cgttacccac gaaatgagac acgctaagac cgttggtatc atcaacgttg    300
acccattgta cggtatcacc gaaatcgctg aaccagttgg tgttgtttgt ggtgttaccc    360
cagttaccaa cccaacctct accgctatct tcaagtcttt gatctctatc aagaccagaa    420
acccaatcgt tttctctttc cacccatctg ctttgaagtg ttctattatg ctgctaaaa    480
tcgttagaga cgctgctatc gctgctggtg ctccagaaaa ctgtatccaa tggatcgaat    540
tcggtggtat cgaagcttct aacaagttga tgaaccaccc aggtgttgct actatcttgg    600
ctaccggtgg taacgctatg gttaaggctg catactcttc tggtaagcca gctttgggtg    660
ttggtgctgg taacgttcca acctacatcg aaaagacctg taacatcaag caagctgcta    720
acgacgttgt tatgtctaag tctttcgaca acggtatgat ctgtgcttct gaacaagctg    780
ctatcatcga caaggaaatc tacgaccaag ttgttgaaga aatgaagacc ttgggtgctt    840
acttcatcaa cgaagaagaa aaggctaagt tggaaaagtt catgttcggt gttaacgctt    900
actctgctga cgttaacaac gctagattga acccaaagtg tccaggtatg tctccacaat    960
ggttcgctga acaagttggt atcaaggtac cagaagactg taacatcatc tgtgctgttt   1020
gtaaggaagt tggtccaaac gaaccattga ccagagaaaa gttgtctcca gttttggcta   1080
tcttgaaagc tgaaaacacc caagacggta tcgacaaggc tgaagctatg gttgaattta   1140
acggtagagg tcactctgct gctatccact ctaacgacaa ggctgttgtt gaaaagtacg   1200
cttttgaccat gaaggcttgt agaatcttgc acaacacccc atcttctcaa ggtggtatcg   1260
gttctatcta caactacatc tggccatctt tcaccttggg ttgtggttct acggtggta    1320
actctgtttc tgctaacgtt acctaccaca acttgttgaa catcaagaga ttggctgaca   1380
gaagaaacaa cttgcaatgg ttcagagttc accaaagat cttcttcgaa ccacactcta   1440
tcagatactt ggctgaattg aaggaattgt ctaagatctt catcgtttct gacagaatga   1500
tgtacaagtt gggttacgtt gacagagtta tggacgtttt gaagagaaga tctaacgaag   1560
ttgaaatcga aatcttcatc gacgttgaac cagacccatc tatccaaacc gttcaaaagg   1620
gtttggctgt tatgaacacc ttcggtccag acaacatcat cgctatcggt ggtggttctg   1680
ctatggacgc tgctaagatc atgtggttgt tgtacgaaca cccagaagct gacttcttcg   1740
ctatgaagca aaagttcatc gacttgagaa agagagcttt caagttccca accatgggta   1800
agaaggctag attgatctgt atcccaacca cctctggtac cggttctgaa gttaccccat   1860
tcgctgttat ctctgaccac gaaaccggta agaagtaccc attggctgac tactctttga   1920
ccccatctgt tgctatcgtt gacccaatgt tcaccatgtc tttgccaaag agagctatcg   1980
ctgacaccgg tttggacgtt ttggttcacg ctaccgaagc ttacgtttct gttatggcta   2040
acgaatacac cgacggtttg gctagagaag ctgttaagtt ggttttttgaa aacttgttga   2100
agtcttacaa cggtgacttg gaagctagag aaaagatgca caacgctgct accatcgctg   2160
gtatggcttt cgcttctgct ttcttgggta tggaccactc tatggctcac aaggttggtg   2220
ctgctttcca cttgccacac ggtagatgtg ttgctgtttt gttgccacac gttatcagat   2280
acaacggtca aaagccaaga agttggcta tgtggccaaa gtacaacttc tacaaggctg   2340
accaaagata catggaattg gctcaaatgg ttggtttgaa gtgtaacacc ccagctgaag   2400
gtgttgaagc tttcgctaag gcttgtgaag aattgatgaa ggctaccgaa accatcaccg   2460
gtttcaagaa ggctaacatc gacgaagctg cttggatgtc taaggttcca gaaatggctt   2520
```

```
tgttggcttt cgaagaccaa tgttctccag ctaacccaag agttccaatg gttaaggaca    2580
tggaaaagat cttgaaggct gcttactacc caatcgctta gcttaag                 2627
```

<210> SEQ ID NO 7
<211> LENGTH: 367
<212> TYPE: PRT
<213> ORGANISM: Escherichia coli

<400> SEQUENCE: 7

```
Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350
```

```
Leu Val Ala Asp Gln Tyr Gly Gln Arg Phe Leu Gln Glu Trp Glu
            355                 360                 365
```

```
<210> SEQ ID NO 8
<211> LENGTH: 584
<212> TYPE: PRT
<213> ORGANISM: Saccharomyces cerevisiae

<400> SEQUENCE: 8

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270

Gly Gly Val Ser Asn Phe Val Ile Ser Ser Ile Thr Ser Lys Thr Thr
        275                 280                 285

Asp Phe Leu Lys Glu Asn Tyr Asn Ile Thr Pro Val Gln Thr Ile Ala
    290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365
```

```
Asp Leu Leu His Asn Glu Val Thr Ala Lys Ala Val Gly Thr Tyr Asp
    370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
    450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
            500                 505                 510

Ser Thr Met Ile Asp Ala Leu Glu Pro Phe Val Lys Glu Phe Thr Ala
        515                 520                 525

Ser Lys Asp Phe Asn Lys Ala Val Lys Ala Ala Glu Glu Gly Ala Lys
    530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580

<210> SEQ ID NO 9
<211> LENGTH: 591
<212> TYPE: PRT
<213> ORGANISM: Saccharomyces cerevisiae

<400> SEQUENCE: 9

Met Ser His Lys Gln Phe Lys Ser Asp Gly Asn Ile Val Thr Pro Tyr
1               5                   10                  15

Leu Leu Gly Leu Ala Arg Ser Asn Pro Gly Leu Thr Val Ile Lys His
            20                  25                  30

Asp Arg Val Val Phe Arg Thr Ala Ser Ala Pro Asn Ser Gly Asn Pro
        35                  40                  45

Pro Lys Val Ser Leu Val Ser Gly Gly Ser Gly His Glu Pro Thr
    50                  55                  60

His Ala Gly Phe Val Gly Glu Gly Ala Leu Asp Ala Ile Ala Ala Gly
65                  70                  75                  80

Ala Ile Phe Ala Ser Pro Ser Thr Lys Gln Ile Tyr Ser Ala Ile Lys
                85                  90                  95

Ala Val Glu Ser Pro Lys Gly Thr Leu Ile Ile Val Lys Asn Tyr Thr
            100                 105                 110

Gly Asp Ile Ile His Phe Gly Leu Ala Ala Glu Arg Ala Lys Ala Ala
        115                 120                 125

Gly Met Lys Val Glu Leu Val Ala Val Gly Asp Asp Val Ser Val Gly
    130                 135                 140

Lys Lys Lys Gly Ser Leu Val Gly Arg Arg Gly Leu Gly Ala Thr Val
```

-continued

```
            145                 150                 155                 160
        Leu Val His Lys Ile Ala Gly Ala Ala Ser His Gly Leu Glu Leu
                        165                 170                 175
        Ala Glu Val Ala Glu Val Ala Gln Ser Val Val Asp Asn Ser Val Thr
                        180                 185                 190
        Ile Ala Ala Ser Leu Asp His Cys Thr Val Pro Gly His Lys Pro Glu
                        195                 200                 205
        Ala Ile Leu Gly Glu Asn Glu Tyr Glu Ile Gly Met Gly Ile His Asn
                        210                 215                 220
        Glu Ser Gly Thr Tyr Lys Ser Ser Pro Leu Pro Ser Ile Ser Glu Leu
        225                 230                 235                 240
        Val Ser Gln Met Leu Pro Leu Leu Leu Asp Glu Asp Glu Asp Arg Ser
                        245                 250                 255
        Tyr Val Lys Phe Glu Pro Lys Glu Asp Val Val Leu Met Val Asn Asn
                        260                 265                 270
        Met Gly Gly Met Ser Asn Leu Glu Leu Gly Tyr Ala Ala Glu Val Ile
                        275                 280                 285
        Ser Glu Gln Leu Ile Asp Lys Tyr Gln Ile Val Pro Lys Arg Thr Ile
                        290                 295                 300
        Thr Gly Ala Phe Ile Thr Ala Leu Asn Gly Pro Gly Phe Gly Ile Thr
        305                 310                 315                 320
        Leu Met Asn Ala Ser Lys Ala Gly Gly Asp Ile Leu Lys Tyr Phe Asp
                        325                 330                 335
        Tyr Pro Thr Thr Ala Ser Gly Trp Asn Gln Met Tyr His Ser Ala Lys
                        340                 345                 350
        Asp Trp Glu Val Leu Ala Lys Gly Gln Val Pro Thr Ala Pro Ser Leu
                        355                 360                 365
        Lys Thr Leu Arg Asn Glu Lys Gly Ser Gly Val Lys Ala Asp Tyr Asp
                        370                 375                 380
        Thr Phe Ala Lys Ile Leu Leu Ala Gly Ile Ala Lys Ile Asn Glu Val
        385                 390                 395                 400
        Glu Pro Lys Val Thr Trp Tyr Asp Thr Ile Ala Gly Asp Gly Asp Cys
                        405                 410                 415
        Gly Thr Thr Leu Val Ser Gly Gly Glu Ala Leu Glu Glu Ala Ile Lys
                        420                 425                 430
        Asn His Thr Leu Arg Leu Glu Asp Ala Ala Leu Gly Ile Glu Asp Ile
                        435                 440                 445
        Ala Tyr Met Val Glu Asp Ser Met Gly Gly Thr Ser Gly Gly Leu Tyr
                        450                 455                 460
        Ser Ile Tyr Leu Ser Ala Leu Ala Gln Gly Val Arg Asp Ser Gly Asp
        465                 470                 475                 480
        Lys Glu Leu Thr Ala Glu Thr Phe Lys Lys Ala Ser Asn Val Ala Leu
                        485                 490                 495
        Asp Ala Leu Tyr Lys Tyr Thr Arg Ala Arg Pro Gly Tyr Arg Thr Leu
                        500                 505                 510
        Ile Asp Ala Leu Gln Pro Phe Val Glu Ala Leu Lys Ala Gly Lys Gly
                        515                 520                 525
        Pro Arg Ala Ala Ala Gln Ala Ala Tyr Asp Gly Ala Glu Lys Thr Arg
                        530                 535                 540
        Lys Met Asp Ala Leu Val Gly Arg Ala Ser Tyr Val Ala Lys Glu Glu
        545                 550                 555                 560
        Leu Arg Lys Leu Asp Ser Glu Gly Gly Leu Pro Asp Pro Gly Ala Val
                        565                 570                 575
```

```
Gly Leu Ala Ala Leu Leu Asp Gly Phe Val Thr Ala Ala Gly Tyr
                580                 585                 590

<210> SEQ ID NO 10
<211> LENGTH: 560
<212> TYPE: PRT
<213> ORGANISM: Saccharomyces cerevisiae

<400> SEQUENCE: 10

Met Ser Leu Ile Ser Ile Leu Ser Pro Leu Ile Thr Ser Glu Gly Leu
1               5                   10                  15

Asp Ser Arg Ile Lys Pro Ser Pro Lys Lys Asp Ala Ser Thr Thr Thr
                20                  25                  30

Lys Pro Ser Leu Trp Lys Thr Thr Glu Phe Lys Phe Tyr Tyr Ile Ala
            35                  40                  45

Phe Leu Val Val Val Pro Leu Met Phe Tyr Ala Gly Leu Gln Ala Ser
        50                  55                  60

Ser Pro Glu Asn Pro Asn Tyr Ala Arg Tyr Glu Arg Leu Leu Ser Gln
65                  70                  75                  80

Gly Trp Leu Phe Gly Arg Lys Val Asp Asn Ser Asp Ser Gln Tyr Arg
                85                  90                  95

Phe Phe Arg Asp Asn Phe Ala Leu Leu Ser Val Leu Met Leu Val His
                100                 105                 110

Thr Ser Ile Lys Arg Ile Val Leu Tyr Ser Thr Asn Ile Thr Lys Leu
            115                 120                 125

Arg Phe Asp Leu Ile Phe Gly Leu Ile Phe Leu Val Ala Ala His Gly
130                 135                 140

Val Asn Ser Ile Arg Ile Leu Ala His Met Leu Ile Leu Tyr Ala Ile
145                 150                 155                 160

Ala His Val Leu Lys Asn Phe Arg Arg Ile Ala Thr Ile Ser Ile Trp
                165                 170                 175

Ile Tyr Gly Ile Ser Thr Leu Phe Ile Asn Asp Asn Phe Arg Ala Tyr
                180                 185                 190

Pro Phe Gly Asn Ile Cys Ser Phe Leu Ser Pro Leu Asp His Trp Tyr
            195                 200                 205

Arg Gly Ile Ile Pro Arg Trp Asp Val Phe Phe Asn Phe Thr Leu Leu
210                 215                 220

Arg Val Leu Ser Tyr Asn Leu Asp Phe Leu Glu Arg Trp Glu Asn Leu
225                 230                 235                 240

Gln Lys Lys Lys Ser Pro Ser Tyr Glu Ser Lys Glu Ala Lys Ser Ala
                245                 250                 255

Ile Leu Leu Asn Glu Arg Ala Arg Leu Thr Ala Ala His Pro Ile Gln
                260                 265                 270

Asp Tyr Ser Leu Met Asn Tyr Ile Ala Tyr Val Thr Tyr Thr Pro Leu
            275                 280                 285

Phe Ile Ala Gly Pro Ile Ile Thr Phe Asn Asp Tyr Val Tyr Gln Ser
        290                 295                 300

Lys His Thr Leu Pro Ser Ile Asn Phe Lys Phe Ile Phe Tyr Tyr Ala
305                 310                 315                 320

Val Arg Phe Val Ile Ala Leu Leu Ser Met Glu Phe Ile Leu His Phe
                325                 330                 335

Leu His Val Val Ala Ile Ser Lys Thr Lys Ala Trp Glu Asn Asp Thr
                340                 345                 350

Pro Phe Gln Ile Ser Met Ile Gly Leu Phe Asn Leu Asn Ile Ile Trp
```

```
                355                 360                 365
Leu Lys Leu Leu Ile Pro Trp Arg Leu Phe Arg Leu Trp Ala Leu Leu
370                 375                 380

Asp Gly Ile Asp Thr Pro Glu Asn Met Ile Arg Cys Val Asp Asn Asn
385                 390                 395                 400

Tyr Ser Ser Leu Ala Phe Trp Arg Ala Trp His Arg Ser Tyr Asn Lys
                405                 410                 415

Trp Val Val Arg Tyr Ile Tyr Ile Pro Leu Gly Gly Ser Lys Asn Arg
                420                 425                 430

Val Leu Thr Ser Leu Ala Val Phe Ser Phe Val Ala Ile Trp His Asp
                435                 440                 445

Ile Glu Leu Lys Leu Leu Leu Trp Gly Trp Leu Ile Val Leu Phe Leu
                450                 455                 460

Leu Pro Glu Ile Phe Ala Thr Gln Ile Phe Ser His Tyr Thr Asp Ala
465                 470                 475                 480

Val Trp Tyr Arg His Val Cys Ala Val Gly Ala Val Phe Asn Ile Trp
                485                 490                 495

Val Met Met Ile Ala Asn Leu Phe Gly Phe Cys Leu Gly Ser Asp Gly
                500                 505                 510

Thr Lys Lys Leu Leu Ser Asp Met Phe Cys Thr Val Ser Gly Phe Lys
                515                 520                 525

Phe Val Ile Leu Ala Ser Val Ser Leu Phe Ile Ala Val Gln Ile Met
                530                 535                 540

Phe Glu Ile Arg Glu Glu Lys Arg His Gly Ile Tyr Leu Lys Cys
545                 550                 555                 560

<210> SEQ ID NO 11
<211> LENGTH: 609
<212> TYPE: PRT
<213> ORGANISM: Saccharomyces cerevisiae

<400> SEQUENCE: 11

Met Ser Met Leu Arg Ile Trp Ser Cys Ile Val His Phe Phe Ser Val
1               5                   10                  15

Gln Ala Leu Asp Ser Arg Ile Lys Pro Asp Ile Glu Phe Lys Arg Arg
                20                  25                  30

Gln Arg Ile Phe Ile Asn Ser Ser Lys Glu Glu Asn Gly Ser Ser Ser
                35                  40                  45

Ser Ala Val Thr Val Thr Arg Asn Pro Val Leu Ser Ser Asn Ser Pro
                50                  55                  60

Ser Pro Pro Leu Trp Asn Thr Trp Glu Phe Arg Leu Tyr Tyr Leu Ala
65              70                  75                  80

Phe Thr Val Val Val Pro Phe Met Ile Lys Ala Ala Leu Ala Thr Ser
                85                  90                  95

Ser Glu Ser Asn Pro Asn Tyr Tyr Lys Phe Ser Gly Leu Leu Ala His
                100                 105                 110

Gly Trp Ile Leu Gly Arg Lys Val Asp Asn Ser Asp Pro Gln Tyr Arg
                115                 120                 125

Phe Phe Arg Ser Asn Phe Phe Leu Leu Ala Ile Leu Ile Leu Leu Gln
                130                 135                 140

Ile Ile Leu Lys Lys Val Phe Val Lys Phe Ser Lys Ile Pro Lys Thr
145                 150                 155                 160

Lys Phe Asp Phe Ala Cys Gly Leu Val Phe Val Cys Phe Met Tyr Gly
                165                 170                 175
```

-continued

```
Ile Asn Ser Val Lys Leu Phe Thr His Ala Phe Ile Phe Phe Thr Leu
            180                 185                 190
Ala His Ser Leu Lys Arg Lys Arg Leu Ile Ala Ala Phe Ala Ile Trp
        195                 200                 205
Ser Tyr Gly Ile Phe Thr Leu Phe Ile Asn Gln Lys Met Lys Asn Leu
    210                 215                 220
Pro Phe Asn Asn Ile Ala Ile Ile Leu Ser Pro Met Asp Gln Trp Tyr
225                 230                 235                 240
Lys Gly Ile Val Pro Arg Trp Asp Phe Phe Asn Phe Thr Leu Leu
                245                 250                 255
Arg Leu Leu Ser Tyr Ser Met Asp Phe Leu Glu Arg Trp His Glu Gln
        260                 265                 270
Leu Ser Arg Gln Pro Ser Ile Asp Tyr Asp Asp Arg Pro Glu Phe
    275                 280                 285
Arg Lys Ser Leu Ser Gly Ser Thr Leu Gln Thr Ile Tyr Glu Ser Gly
        290                 295                 300
Lys Asn Val Leu Glu Glu Lys Glu Arg Leu Val Ala Glu His His Ile
305                 310                 315                 320
Gln Asp Tyr Asn Phe Ile Asn Phe Ile Ala Tyr Ile Thr Tyr Ala Pro
                325                 330                 335
Leu Phe Leu Val Gly Pro Ile Ile Thr Phe Asn Asp Tyr Leu Tyr Gln
                340                 345                 350
Ser Glu Asn Lys Leu Pro Ser Leu Thr Lys Lys Asn Ile Gly Phe Tyr
        355                 360                 365
Ala Leu Lys Val Phe Ser Ser Leu Leu Leu Met Glu Ile Ile Leu His
    370                 375                 380
Tyr Ile Tyr Val Gly Ala Ile Ala Arg Thr Lys Ala Trp Asn Asn Asp
385                 390                 395                 400
Thr Pro Leu Gln Gln Ala Met Ile Ala Leu Phe Asn Leu Asn Ile Met
                405                 410                 415
Tyr Leu Lys Leu Leu Ile Pro Trp Arg Leu Phe Arg Leu Trp Ala Met
        420                 425                 430
Val Asp Gly Ile Asp Ala Pro Glu Asn Met Leu Arg Cys Val Asp Asn
    435                 440                 445
Asn Tyr Ser Thr Val Gly Phe Trp Arg Ala Trp His Thr Ser Phe Asn
450                 455                 460
Lys Trp Val Ile Arg Tyr Ile Tyr Val Pro Phe Gly Gly Ser Asn Asn
465                 470                 475                 480
Lys Ile Leu Thr Ser Phe Ala Val Phe Ser Phe Val Ala Ile Trp His
                485                 490                 495
Asp Ile Gln Leu Arg Val Leu Phe Trp Gly Trp Leu Thr Val Leu Leu
        500                 505                 510
Leu Leu Gly Glu Thr Tyr Ile Thr Asn Cys Phe Ser Arg Tyr Arg Phe
    515                 520                 525
Arg Ser Trp Tyr Arg Phe Val Cys Gly Ile Gly Ala Ala Ile Asn Ile
530                 535                 540
Cys Met Met Met Ile Ile Asn Val Tyr Gly Phe Cys Leu Gly Ala Glu
545                 550                 555                 560
Gly Thr Lys Leu Leu Leu Lys Gly Ile Phe Asn Asn Ser His Ser Pro
                565                 570                 575
Glu Phe Leu Thr Ala Val Met Val Ser Leu Phe Ile Ala Val Gln Val
        580                 585                 590
Met Phe Glu Ile Arg Glu Glu Glu Lys Arg His Gly Ile Asn Leu Lys
```

Cys

<210> SEQ ID NO 12
<211> LENGTH: 669
<212> TYPE: PRT
<213> ORGANISM: Saccharomyces cerevisiae

<400> SEQUENCE: 12

Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His His Ser Gly Gly
        35                  40                  45

Thr Asn Asn Asn Asn Asn Asn Asn Asn Asn Asn Asn Ser Asn Asn
    50                  55                  60

Asn Asn Asn Gly Asn Asp Gly Gly Asn Asp Asp Tyr Asp Tyr Glu
65                  70                  75                  80

Met Gln Asp Tyr Arg Pro Ser Pro Gln Ser Ala Arg Pro Thr Pro Thr
            85                  90                  95

Tyr Val Pro Gln Tyr Ser Val Glu Ser Gly Thr Ala Phe Pro Ile Gln
        100                 105                 110

Glu Val Ile Pro Ser Ala Tyr Ile Asn Thr Gln Asp Ile Asn His Lys
    115                 120                 125

Asp Asn Gly Pro Pro Ser Ala Ser Ser Asn Arg Ala Phe Arg Pro Arg
130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
            165                 170                 175

Arg Arg Ser Arg Ser Arg Ala Thr Ser Asn Ala Gly His Ser Ala Asn
        180                 185                 190

Thr Gly Ala Thr Asn Gly Arg Thr Thr Gly Ala Gln Thr Asn Met Glu
    195                 200                 205

Ser Asn Glu Ser Pro Arg Asn Val Pro Ile Met Val Lys Pro Lys Thr
210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
            245                 250                 255

Leu Ala Glu Phe Met Gly Thr Met Val Met Ile Ile Phe Gly Ser Ala
        260                 265                 270

Val Val Cys Gln Val Asn Val Ala Gly Lys Ile Gln Gln Asp Asn Phe
    275                 280                 285

Asn Val Ala Leu Asp Asn Leu Asn Val Thr Gly Ser Ser Ala Glu Thr
290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Val Val Met
            325                 330                 335

Gly Tyr Phe Cys Ala Gly Gly Ser Ala Ile Ser Gly Ala His Leu Asn
        340                 345                 350

Pro Ser Ile Thr Leu Ala Asn Leu Val Tyr Arg Gly Phe Pro Leu Lys 355                 360                 365
Lys Val Pro Tyr Tyr Phe Ala Gly Gln Leu Ile Gly Ala Phe Thr Gly
    370                 375                 380

Ala Leu Ile Leu Phe Ile Trp Tyr Lys Arg Val Leu Gln Glu Ala Tyr
385                 390                 395                 400

Ser Asp Trp Trp Met Asn Glu Ser Val Ala Gly Met Phe Cys Val Phe
                405                 410                 415

Pro Lys Pro Tyr Leu Ser Ser Gly Arg Gln Phe Phe Ser Glu Phe Leu
            420                 425                 430

Cys Gly Ala Met Leu Gln Ala Gly Thr Phe Ala Leu Thr Asp Pro Tyr
        435                 440                 445

Thr Cys Leu Ser Ser Asp Val Phe Pro Leu Met Met Phe Ile Leu Ile
    450                 455                 460

Phe Ile Ile Asn Ala Ser Met Ala Tyr Gln Thr Gly Thr Ala Met Asn
465                 470                 475                 480

Leu Ala Arg Asp Leu Gly Pro Arg Leu Ala Leu Tyr Ala Val Gly Phe
                485                 490                 495

Asp His Lys Met Leu Trp Val His His His Phe Trp Val Pro
            500                 505                 510

Met Val Gly Pro Phe Ile Gly Ala Leu Met Gly Gly Leu Val Tyr Asp
        515                 520                 525

Val Cys Ile Tyr Gln Gly His Glu Ser Pro Val Asn Trp Ser Leu Pro
    530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
                565                 570                 575

Tyr Asn Asn Asp Asp Asp Glu Glu Phe Gly Glu Arg Met Ala Leu Gln
            580                 585                 590

Lys Thr Lys Thr Lys Ser Ser Ile Ser Asp Asn Glu Asn Glu Ala Gly
        595                 600                 605

Glu Lys Lys Val Gln Phe Lys Ser Val Gln Arg Gly Lys Arg Thr Phe
    610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
            660                 665

<210> SEQ ID NO 13
<211> LENGTH: 713
<212> TYPE: PRT
<213> ORGANISM: Saccharomyces cerevisiae

<400> SEQUENCE: 13

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

```
His Tyr Ser Pro His Leu Asp Gly Leu Gln Asp Tyr Gln Arg Leu His
 65                  70                  75                  80

Lys Glu Ser Ile Glu Asp Pro Ala Lys Phe Phe Gly Ser Lys Ala Thr
                 85                  90                  95

Gln Phe Leu Asn Trp Ser Lys Pro Phe Asp Lys Val Phe Ile Pro Asp
            100                 105                 110

Pro Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
    130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
    210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
    290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
    370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
    450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe
```

Pro Phe Phe Gly Ile Asp Ala Val Val Leu Asp Pro Asn Thr Gly Glu
            485                 490                 495
                500                 505                 510

Glu Leu Asn Thr Ser His Ala Glu Gly Val Leu Ala Val Lys Ala Ala
            515                 520                 525

Trp Pro Ser Phe Ala Arg Thr Ile Trp Lys Asn His Asp Arg Tyr Leu
            530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
                565                 570                 575

Asp Val Val Asn Val Ser Gly His Arg Leu Ser Thr Ala Glu Ile Glu
                580                 585                 590

Ala Ala Ile Ile Glu Asp Pro Ile Val Ala Glu Cys Ala Val Val Gly
                595                 600                 605

Phe Asn Asp Asp Leu Thr Gly Gln Ala Val Ala Ala Phe Val Val Leu
            610                 615                 620

Lys Asn Lys Ser Ser Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
                660                 665                 670

Ser Gly Lys Ile Met Arg Arg Ile Leu Arg Lys Ile Leu Ala Gly Glu
            675                 680                 685

Ser Asp Gln Leu Gly Asp Val Ser Thr Leu Ser Asn Pro Gly Ile Val
            690                 695                 700

Arg His Leu Ile Asp Ser Val Lys Leu
705                 710

<210> SEQ ID NO 14
<211> LENGTH: 683
<212> TYPE: PRT
<213> ORGANISM: Saccharomyces cerevisiae

<400> SEQUENCE: 14

Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
50                  55                  60

Trp Asp Ala Pro Tyr Thr Lys Val Gln Ser Gly Ser Leu Asn Asn Gly
65              70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
            100                 105                 110

Glu Ala Asp Asp Glu Ser Asp Asn Lys Ile Ile Thr Phe Gly Glu Leu
        115                 120                 125

Leu Arg Lys Val Ser Gln Ile Ala Gly Val Leu Lys Ser Trp Gly Val
    130                 135                 140

-continued

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
            180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
    210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
            260                 265                 270

Leu Phe Leu Leu Tyr Thr Ser Gly Ser Thr Gly Ser Pro Lys Gly Val
        275                 280                 285

Val His Thr Thr Gly Gly Tyr Leu Leu Gly Ala Ala Leu Thr Thr Arg
    290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
        355                 360                 365

Tyr Val Ala Pro Thr Ala Leu Arg Leu Ile Lys Arg Val Gly Glu Ala
    370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
            420                 425                 430

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
                485                 490                 495

His Asp Arg Tyr Met Asp Thr Tyr Leu Lys Pro Tyr Pro Gly His Tyr
            500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val

```
                        565                 570                 575
Ala Tyr Val Ser Leu Lys Asp Gly Tyr Leu Gln Asn Asn Ala Thr Glu
                580                 585                 590

Gly Asp Ala Glu His Ile Thr Pro Asp Asn Leu Arg Arg Glu Leu Ile
            595                 600                 605

Leu Gln Val Arg Gly Glu Ile Gly Pro Phe Ala Ser Pro Lys Thr Ile
        610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
                645                 650                 655

Leu Thr Thr Leu Ala Asn Pro Glu Val Val Pro Ala Ile Ile Ser Ala
            660                 665                 670

Val Glu Asn Gln Phe Phe Ser Gln Lys Lys Lys
        675                 680

<210> SEQ ID NO 15
<211> LENGTH: 384
<212> TYPE: PRT
<213> ORGANISM: Saccharomyces cerevisiae

<400> SEQUENCE: 15

Met Thr Ala His Thr Asn Ile Lys Gln His Lys His Cys His Glu Asp
1               5                   10                  15

His Pro Ile Arg Arg Ser Asp Ser Ala Val Ser Ile Val His Leu Lys
            20                  25                  30

Arg Ala Pro Phe Lys Val Thr Val Ile Gly Ser Gly Asn Trp Gly Thr
        35                  40                  45

Thr Ile Ala Lys Val Ile Ala Glu Asn Thr Glu Leu His Ser His Ile
    50                  55                  60

Phe Glu Pro Glu Val Arg Met Trp Val Phe Asp Glu Lys Ile Gly Asp
65                  70                  75                  80

Glu Asn Leu Thr Asp Ile Ile Asn Thr Arg His Gln Asn Val Lys Tyr
                85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
        115                 120                 125

Gln Phe Leu Pro Asn Ile Val Lys Gln Leu Gln Gly His Val Ala Pro
130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
        195                 200                 205

Gly Asp Gly Lys Asp Val Asp His Lys Ile Leu Lys Leu Leu Phe His
    210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255
```

```
Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
        275                 280                 285

Lys Val Glu Thr Tyr Tyr Gln Glu Ser Ala Gly Val Ala Asp Leu Ile
    290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350

Gln Thr Cys Glu Leu Thr Gln Glu Phe Pro Ile Ile Arg Gly Ser Leu
        355                 360                 365

Pro Asp Ser Leu Gln Gln Arg Pro His Gly Arg Pro Thr Gly Asp Asp
    370                 375                 380
```

<210> SEQ ID NO 16
<211> LENGTH: 391
<212> TYPE: PRT
<213> ORGANISM: Saccharomyces cerevisiae

<400> SEQUENCE: 16

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255
```

```
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
    290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
    370                 375                 380
Glu Leu Asp Leu His Glu Asp
385                 390

<210> SEQ ID NO 17
<211> LENGTH: 2573
<212> TYPE: DNA
<213> ORGANISM: Artificial
<220> FEATURE:
<223> OTHER INFORMATION: GDP1 disruption

<400> SEQUENCE: 17 ggtaccccccg ccttgcttct ctcccctttcc ttttcttttt ccagttttcc ctattttgtc      60
ccttttttccg cacaacaagt atcagaatgg gttcatcaaa tctatccaac ctaattcgca     120
cgtagactgg cttggtattg cagtttcgt agttatatat atactaccat gagtgaaact       180
gttacgttac cttaaattct ttctccctttt aattttctttt tatcttactc tcctacataa    240
gacatcaaga aacaattgta tattgtacac cccccccctc cacaaacaca aatattgata     300
atataaagat gtctgctgct gctgatagat taaacttaac ttccggccac ttgaatctag     360
atgcatgctc gagcggccgc cagtgtgatg gatatctgca gaattcgccc ttttgggccc     420
tgtacaccta ggatccgtcg acactggatg gcggcgttag tatcgaatcg acagcagtat     480
agcgaccagc attcacatac gattgacgca tgatattact ttctgcgcac ttaacttcgc     540
atctgggcag atgatgtcga ggcgaaaaaa aatataaatc acgctaacat ttgattaaaa     600
tagaacaact acaatataaa aaaactatac aaatgacaag ttcttgaaaa caagaatctt     660
tttattgtca gtactgatta ttcctttgcc ctcggacgag tgctggggcg tcggtttcca     720
ctatcggcga gtacttctac acagccatcg gtccagacgg ccgcgcttct gcgggcgatt     780
tgtgtacgcc cgacagtccc ggctccggat cggacgattg cgtcgcatcg accctgcgcc     840
caagctgcat catcgaaatt gccgtcaacc aagctctgat agagttggtc aagaccaatg     900
cggagcatat acgcccggag ccgcggcgat cctgcaagct ccggatgcct ccgctcgaag     960
tagcgcgtct gctgctccat acaagccaac cacggcctcc agaagaagat gttggcgacc    1020
tcgtattggg aatccccgaa catcgcctcg ctccagtcaa tgaccgctgt tatgcggcca    1080
ttgtccgtca ggacattgtt ggagccgaaa tccgcgtgca cgaggtgccg gacttcgggg    1140
cagtcctcgg cccaaagcat cagctcatcg agagcctgcg cgacggacgc actgacggtg    1200
tcgtccatca cagtttgcca gtgatacaca tggggatcag caatcgcgca tatgaaatca    1260
```

```
cgccatgtag tgtattgacc gattccttgc ggtccgaatg ggccgaaccc gctcgtctgg    1320
ctaagatcgg ccgcagcgat cgcatccatg gcctccgcga ccggctgcag aacagcgggc    1380
agttcggttt caggcaggtc ttgcaacgtg acaccctgtg cacggcggga gatgcaatag    1440
gtcaggctct cgctgaattc cccaatgtca agcacttccg gaatcgggag cgcggccgat    1500
gcaaagtgcc gataaacata acgatctttg tagaaaccat cggcgcagct atttacccgc    1560
aggacatatc cacgccctcc tacatcgaag ctgaaagcac gagattcttc gcctccgag    1620 agctgcatca ggtcggagac gctgtcgaac ttttcgatca gaaacttctc gacagacgtc    1680
gcggtgagtt caggcttttt acccatggtt gtttatgttc ggatgtgatg tgagaactgt    1740
atcctagcaa gattttaaaa ggaagtatat gaaagaagaa cctcagtggc aaatcctaac    1800
cttttatatt tctctacagg ggcgcggcgt ggggacaatt cacgcgtctg tgaggggagc    1860
gtttccctgc tcgcaggtct gcagcgagga gccgtaattt ttgcttcgcg ccgtgcggcc    1920
atcaaaatgt atggatgcaa atgattatac atggggatgt atgggctaaa tgtacgggcg    1980
acagtcacat catgcccctg agctgcgcac gtcaagactg tcaaggaggg tattctgggc    2040
ctccatgtcg ctggccgggt gaccggcgg ggacgaggcc ttaagttcga acgtacggag    2100 tgttgaatg gccaatccgc tcaaggttta attacctgca aagaagttca cgaatggttg    2160
gaaacatgtg gctctgtcga agacttccca ttatttgaag ccgtatacca atcgtttac    2220 aacaactacc caatgaagaa cctgccggac atgattgaag aattagatct acatgaagat    2280
tagatttatt ggagaaagat aacatatcat actttccccc acttttttcg aggctcttct    2340
atatcatatt cataaattag cattatgtca tttctcataa ctactttatc acgttagaaa    2400
ttacttatta ttattaaatt aatacaaaat ttagtaacca aataaatata aataaatatg    2460
tatatttaaa ttttaaaaaa aaaatcctat agagcaaaag gattttccat tataatatta    2520
gctgtacacc tcttccgcat tttttgaggg tggttacaac accactcggt acc          2573
```

<210> SEQ ID NO 18
<211> LENGTH: 2058
<212> TYPE: DNA
<213> ORGANISM: Artificial
<220> FEATURE:
<223> OTHER INFORMATION: GPD2 disruption

<400> SEQUENCE: 18

```
agatcttttg cggcgaggtg ccgatgggtt gctgagggga agagtgttta gcttacggac     60
ctattgccat tgttattccg attaatctat tgttcagcag ctcttctcta ccctgtcatt    120
ctagtatttt ttttttttt ttttggtttt acttttttt cttcttgcct ttttttcttg     180 ttacttttt tctagttttt tttccttcca ctaagctttt tccttgattt atccttgggt    240
tcttctttct actccttag atttttttt tatatattaa ttttttaagtt tatgtattt     300 ggtagattca attctctttc cctttccttt tccttcgctc cccttcctta tcaatgcttg    360
ctgtcagaag attaacaaga tacacattcc ttaaggcctc gtccccgccg ggtcacccgg    420
ccagcgacat ggaggcccag aatacccctcc ttgacagtct tgacgtgcgc agctcagggg    480
catgatgtga ctgtcgcccg tacatttagc ccatacatcc ccatgtataa tcatttgcat    540
ccatacattt tgatggccgc acggcgcgaa gcaaaaatta cggctcctcg ctgcagacct    600
gcgagcaggg aaacgctccc ctcacagacg cgttgaattg tccccacgcc gcgcccctgt    660
agagaaatat aaaaggttag gatttgccac tgaggttctt ctttcatata cttccttttta    720
```

```
aaatcttgct aggatacagt tctcacatca catccgaaca taaacaacca tgtaaaatga    780
ccactcttga cgacacggct taccggtacc gcaccagtgt cccgggggac gccgaggcca    840
tcgaggcact ggatgggtcc ttcaccaccg acaccgtctt ccgcgtcacc gccaccgggg    900
acggcttcac cctgcgggag gtgccggtgg acccgcccct gaccaaggtg ttccccgacg    960
acgaatcgga cgacgaatcg gacgccgggg aggacggcga cccggactcc cggacgttcg   1020
tcgcgtacgg ggacgacggc gacctggcgg gcttcgtggt cgtctcgtac tccggctgga   1080
accgccggct gaccgtcgag gacatcgagg tcgccccgga gcaccggggg cacggggtcg   1140
ggcgcgcgtt gatggggctc gcgacggagt tcgcccgcga gcggggcgcc gggcacctct   1200
ggctggaggt caccaacgtc aacgcaccgg cgatccacgc gtaccggcgg atggggttca   1260
ccctctgcgg cctggacacc gccctgtacg acggcaccgc ctcggacggc gagcaggcgc   1320
tctacatgag catgccctgc ccctagtact gacaataaaa agattcttgt tttcaagaac   1380
ttgtcatttg tatagttttt ttatattgta gttgttctat tttaatcaaa tgttagcgtg   1440
atttatattt tttttcgcct cgacatcatc tgcccagatg cgaagttaag tgcgcagaaa   1500
gtaatatcat gcgtcaatcg tatgtgaatg ctggtcgcta tactgctgtc gattcgatac   1560
taacgccgcc atccagtgtc gacggatcct aggtgtacag ggcccaaaag ggcgaattct   1620
gcagatatcc atcacactgg cggccgctcg aggatagtct acaacaacgt ccgcatggaa   1680
gacctaccgg agatgattga agagctagac atcgatgacg aatagacact ctcccccccc   1740
ctccccctct gatctttcct gttgcctctt tttcccccaa ccaatttatc attatacaca   1800
agttctacaa ctactactag taacattact acagttatta taattttcta ttctcttttt   1860
ctttaagaat ctatcattaa cgttaatttc tatatataca taactaccat tatacacgct   1920
attatcgttt acatatcaca tcaccgttaa tgaaagatac gacaccctgt acactaacac   1980
aattaaataa tcgccataac ctttctctgtt atctatagcc cttaaagctg tttcttcgag   2040 cttttttcact gcagatct                                                2058

<210> SEQ ID NO 19
<211> LENGTH: 816
<212> TYPE: DNA
<213> ORGANISM: Saccharomyces cerevisiae

<400> SEQUENCE: 19
ccatatgatc atgtgtcgtc gcacacatat atatatgcct gtatgtgtca gcactaaagt     60
tgcctggcca tccacgctat atatacacgc ctggcggatc tgctcgagga ttgcctacgc    120
gtgggcttga tccaccaacc aacgctcgcc aaatgaactg gcgctttggt cttctgccat    180
cgtccgtaaa cccggccaa agagaccgga aagatcggtg aaaacatctt gatcttgctc    240
ccgggaattt tagattcagg taggaaattg attacatcaa tactgttacc ctgaatcata    300
ttcgacgatg tcgtctcaca cggaaatata attcatttct ggttttccaa aaaaaatttt    360 cattttttt cactttttg tttcgtcctc cttttttttt tttttttttt atttttttc       420 ctgtgttcac cttttttttt ttcagttgac atctttctgc attcttttct gtgtttttt    480 tttttttttt cgtttttcca ttgttcgttc gttgcctgtt ttttcgccct attgttctcg    540
agcctaaaaa tttttttcctt tcctgctttc ctttcttcgt tcaaagtttc ctattccatt   600
gttctctttg gtaaactcat tgttgtcgga actcagatat attcaggtca atttactgta    660
cttcaattga ctttttctt gaaatttcaa cttgcctttt caacttgttc ttcttttta     720 atcttattct acactttagt tcccttacct tgttcctaat tattgtctag caaaaagaaa    780
```
acatacacct atttcattca cacactgcag aaaatg         816

<210> SEQ ID NO 20
<211> LENGTH: 12350
<212> TYPE: DNA
<213> ORGANISM: Artificial
<220> FEATURE:
<223> OTHER INFORMATION: pRN500

<400> SEQUENCE: 20
tcgatgataa gctgtcaaag atgagaatta attccacgga ctatagacta tactagatac    60
tccgtctact gtacgataca cttccgctca ggtccttgtc ctttaacgag gccttaccac   120
tcttttgtta ctctattgat ccagctcagc aaaggcagtg tgatctaaga ttctatcttc   180
gcgatgtagt aaaactagct agaccgagaa agagactaga aatgcaaaag gcacttctac   240
aatggctgcc atcattatta tccgatgtga cgctgcagct tctcaatgat attcgaatac   300
gctttgagga gatacagcct aatatccgac aaactgtttt acagatttac gatcgtactt   360
gttacccatc attgaatttt gaacatccga acctgggagt tttccctgaa acagatagta   420
tatttgaacc tgtataataa tatatagtct agcgctttac ggaagacaat gtatgtattt   480
cggttcctgg agaaactatt gcatctattg cataggtaat cttgcacgtc gcatccccgg   540
ttcatttttct gcgtttccat cttgcacttc aatagcatat ctttgttaac gaagcatctg   600
tgcttcattt tgtagaacaa aaatgcaacg cgagagcgct aattttttcaa acaaagaatc   660
tgagctgcat ttttacagaa cagaaatgca acgcgaaagc gctatttttac caacgaagaa   720
tctgtgcttc attttttgtaa aacaaaaatg caacgcgacg agagcgctaa ttttttcaaac   780
aaagaatctg agctgcattt ttacagaaca gaaatgcaac gcgagagcgc tattttacca   840
acaaagaatc tatacttctt ttttgttcta caaaaatgca tcccgagagc gctatttttc   900
taacaaagca tcttagatta cttttttttct cctttgtgcg ctctataatg cagtctcttg   960
ataactttttt gcactgtagg tccgttaagg ttagaagaag gctactttgg tgtctatttt  1020
ctcttccata aaaaaagcct gactccactt cccgcgttta ctgattacta gcgaagctgc  1080
gggtgcattt tttcaagata aaggcatccc cgattatatt ctataccgat gtggattgcg  1140
catactttgt gaacagaaag tgatagcgtt gatgattctt cattggtcag aaaattatga  1200
acggtttctt ctatttttgtc tctatatact acgtatagga aatgtttaca ttttcgtatt  1260
gttttcgatt cactctatga atagttctta ctacaatttt tttgtctaaa gagtaatact  1320
agagataaac ataaaaaatg tagaggtcga gtttagatgc aagttcaagg agcgaaaggt  1380
ggatgggtag gttatatagg gatatagcac agagatatat agcaaagaga tacttttgag  1440
caatgtttgt ggaagcggta ttcgcaatgc cggctttccc cgtcaagctc taaatcgggg  1500
gctccctta gggttccgat ttagtgcttt acggcacctc gaccccaaaa aacttgatta  1560
gggtgatggt tcacgtagtg ggccatcgcc ctgatagacg ttttttcgcc ctttgacgtt  1620
ggagtccacg ttctttaata gtggactctt gttccaaact ggaacaacac tcaaccctat  1680
ctcggtctat tcttttgatt tataagggat tttgccgatt tcggcctatt ggttaaaaaa  1740
tgagctgatt taacaaaaat ttaacgcgaa ttttaacaaa atattaacgt ttacaatttc  1800
ctgatgcggt attttctcct tacgcatctg tgcggtattt cacaccgcag gtaataact  1860
gatataatta aattgaagct ctaatttgtg agtttagtat acatgcattt acttataata  1920
cagtttttta gttttgctgg ccgcatcttc tcaaatatgc ttcccagcct gcttttctgt  1980

```
aacgttcacc ctctacctta gcatcccttc cctttgcaaa tagtcctctt ccaacaataa    2040
taatgtcaga tcctgtagag accacatcat ccacggttct atactgttga cccaatgcgt    2100
ctcccttgtc atctaaaccc acaccgggtg tcataatcaa ccaatcgtaa ccttcatctc    2160
ttccacccat gtctctttga gcaataaagc cgataacaaa atctttgtcg ctcttcgcaa    2220
tgtcaacagt acccttagta tattctccag tagatabgga gcccttgcat gacaattctg    2280
ctaacatcaa aaggcctcta ggttcctttg ttacttcttc tgccgcctgc ttcaaaccgc    2340
taacaatacc tgggcccacc acaccgtgtg cattcgtaat gtctgcccat tctgctattc    2400
tgtatacacc cgcagagtac tgcaatttga ctgtattacc aatgtcagca aattttctgt    2460
cttcgaagag taaaaaattg tacttggcgg ataatgcctt tagcggctta actgtgccct    2520
ccatggaaaa atcagtcaag atatccacat gtgtttttag taaacaaatt ttgggaccta    2580
atgcttcaac taactccagt aattccttgg tggtacgaac atccaatgaa gcacacaagt    2640
ttgtttgctt ttcgtgcatg atattaaata gcttggcagc aacaggacta ggatgagtag    2700
cagcacgttc cttatatgta gctttcgaca tgatttatct tcgtttcctg caggtttttg    2760
ttctgtgcag ttgggttaag aatactgggc aatttcatgt ttcttcaaca ctacatatgc    2820
gtatatatac caatctaagt ctgtgctcct tccttcgttc ttccttctgt tcggagatta    2880
ccgaatcaaa aaatttcaa agaaaccgaa atcaaaaaaa agaataaaaa aaaatgatg    2940
aattgaattg aaaagcgtgg tgcactctca gtacaatctg ctctgatgcc gcatagttaa    3000
gccagccccg acaccgcca acaccgctg acgcgccctg acgggcttgt ctgctcccgg      3060
catccgctta cagacaagct gtgaccgtct ccgggagctg catgtgtcag aggttttcac    3120
cgtcatcacc gaaacgcgcg agacgaaagg gcctcgtgat acgcctattt ttataggtta    3180
atgtcatgat aataatggtt tcttagacgt caggtggcac ttttcgggga aatgtgcgcg    3240
gaaccectat tgtttattt ttctaaatac attcaaatat gtatccgctc atgagacaat     3300
aaccctgata aatgcttcaa taatattgaa aaggaagag tatgagtatt caacattttcc   3360
gtgtcgccct tattccctttt tttgcggcat tttgccttcc tgtttttgct cacccagaaa  3420
cgctggtgaa agtaaaagat gctgaagatc agttgggtgc acgagtgggt tacatcgaac   3480
tggatctcaa cagcggtaag atccttgaga gttttcgccc cgaagaacgt tttccaatga   3540
tgagcacttt taaagttctg ctatgtggcg cggtattatc ccgtattgac gccgggcaag   3600
agcaactcgg tcgccgcata cactattctc agaatgactt ggttgagtac tcaccagtca   3660
cagaaaagca tcttacggat ggcatgacag taagagaatt atgcagtgct gccataacca   3720
tgagtgataa cactgcggcc aacttacttc tgacaacgat cggaggaccg aaggagctaa   3780
ccgcttttt tcacaacatg ggggatcatg taactcgcct tgatcgttgg gaaccggagc    3840
tgaatgaagc cataccaaac gacgagcgtg acaccacgat gcctgtagca atggcaacaa   3900
cgttgcgcaa actattaact ggcgaactac ttactctagc ttcccggcaa caattaatag   3960
actggatgga ggcggataaa gttgcaggac cacttctgcg ctcggccctt ccggctggct   4020
ggtttattgc tgataaatct ggagccggtg agcgtgggtc tcgcggtatc attgcagcac   4080
tggggccaga tggtaagccc tcccgtatcg tagttatcta cacgacgggc agtcaggcaa   4140
ctatggatga acgaaataga cagatcgctg agataggtgc ctcactgatt aagcattggt   4200
aactgtcaga ccaagtttac tcatatatac tttagattga tttaaaactt catttttaat   4260
ttaaaaggat ctaggtgaag atcctttttg ataatctcat gaccaaaatc ccttaacgtg   4320
agttttcgtt ccactgagcg tcagacccccg tagaaaagat caaaggatct tcttgagatc  4380
```

```
cttttttttct gcgcgtaatc tgctgcttgc aaacaaaaaa accaccgcta ccagcggtgg    4440
tttgtttgcc ggatcaagag ctaccaactc tttttccgaa ggtaactggc ttcagcagag    4500
cgcagatacc aaatactgtc cttctagtgt agccgtagtt aggccaccac ttcaagaact    4560
ctgtagcacc gcctacatac ctcgctctgc taatcctgtt accagtggct gctgccagtg    4620
gcgataagtc gtgtcttacc gggttggact caagacgata gttaccggat aaggcgcagc    4680
ggtcgggctg aacggggggt tcgtgcacac agcccagctt ggagcgaacg acctacaccg    4740
aactgagata cctacagcgt gagcattgag aaagcgccac gcttcccgaa gggagaaagg    4800
cggacaggta tccggtaagc ggcagggtcg aacaggaga gcgcacgagg gagcttccag    4860
gggggaacgc ctggtatctt tatagtcctg tcgggtttcg ccacctctga cttgagcgtc    4920 gattttgtg atgctcgtca ggggggccga gcctatggaa aaacgccagc aacgcggcct    4980
ttttacggtt cctggccttt tgctggcctt ttgctcacat gttctttcct gcgttatccc    5040
ctgattctgt ggataaccgt attaccgcct ttgagtgagc tgataccgct cgccgcagcc    5100
gaacgaccga gcgcagcgag tcagtgagcg aggaagcgga agagcgccca atacgcaaac    5160
cgcctctccc cgcgcgttgg ccgattcatt aatgcagctg gcacgacagg tttcccgact    5220
ggaaagcggg cagtgagcgc aacgcaatta atgtgagtta cctcactcat taggcacccc    5280
aggctttaca ctttatgctt ccggctccta tgttgtgtgg aattgtgagc ggataacaat    5340
ttcacacagg aaacagctat gaccatgatt acgccaagct cggaattaac cctcactaaa    5400
gggaacaaaa gctgggtacc gggcccccc tcgaccggtc ccacacacca tagcttcaaa    5460
atgtttctac tccttttta ctcttccaga ttttctcgga ctccgcgcat cgccgtacca    5520
cttcaaaaca cccaagcaca gcatactaaa tttcccctct ttcttcctct agggtgtcgt    5580
taattacccg tactaaaggt ttggaaaaga aaaagagac cgcctcgttt cttttcttc    5640 gtcgaaaaag gcaataaaaa tttttatcac gtttctttt cttgaaaatt ttttttttg    5700 attttttct ctttcgatga cctcccattg atatttaagt taataaacgg tcttcaattt    5760
ctcaagtttc agtttcattt ttcttgttct attacaactt ttttacttc ttgctcatta    5820 gaaagaaagc atagcaatct aatctaagct gcagaagctt aaaatgtcgc cctctgccgt    5880
acaatcatca aaactagaag aacagtcaag tgaaattgac aagttgaaag caaaaatgtc    5940
ccagtctgcc gccactgcgc agcagaagaa ggaacatgag tatgaacatt tgacttcggt    6000
caagatcgtg ccacaacggc ccatctcaga tagactgcag cccgcaattg ctacccacta    6060
ttctccacac ttggacgggt tgcaggacta tcagcgcttg cacaaggagt ctattgaaga    6120
ccctgctaag ttcttcggtt ctaaagctac ccaattttta aactggtcta agccattcga    6180
taaggtgttc atcccagacc ctaaaacggg caggccctcc ttccagaaca atgcatggtt    6240
cctcaacggc caattaaacg cctgttacaa ctgtgttgac agacatgcct tgaagactcc    6300
taacaagaaa gccattattt tcgaaggtga cgagcctggc caaggctatt ccattaccta    6360
caaggaacta cttgaagaag tttgtcaagt ggcacaagtg ctgacttact ctatgggcgt    6420
tcgcaagggc gatactgttg ccgtgtacat gcctatggtc ccagaagcaa tcataacctt    6480
gttggccatt tcccgtatcg gtgccattca ctccgtagtc tttgccgggt tttcttccaa    6540
ctccttgaga gatcgtatca acgatgggga ctctaaagtt gtcatcacta cagatgaatc    6600
caacagaggt ggtaaagtca ttgagactaa aagaattgtt gatgacgcgc taagagagac    6660
cccaggcgtg agacacgtct tggtttatag aaagaccaac aatccatctg ttgctttcca    6720
```

```
tgcccccaga gatttggatt gggcaacaga aaagaagaaa tacaagacct actatccatg    6780
cacacccgtt gattctgagg atccattatt cttgttgtat acgtctggtt ctactggtgc    6840
ccccaagggt gttcaacatt ctaccgcagg ttacttgctg ggagctttgt tgaccatgcg    6900
ctacactttt gacactcacc aagaagacgt tttcttcaca gctggagaca ttggctggat    6960
tacaggccac acttatgtgg tttatggtcc cttactatat ggttgtgcca ctttggtctt    7020
tgaagggact cctgcgtacc caaattactc ccgttattgg gatattattg atgaacacaa    7080
agtcacccaa ttttatgttg cgccaactgc tttgcgtttg ttgaaaagag ctggtgattc    7140
ctacatcgaa aatcattcct taaaatcttt gcgttgcttg ggttcggtcg gtgagccaat    7200
tgctgctgaa gtttgggagt ggtactctga aaaataggt aaaaatgaaa tccccattgt    7260
agacacctac tggcaaacag aatctggttc gcatctggtc accccgctgg ctggtggtgt    7320
tacaccaatg aaaccgggtt ctgcctcatt ccccttcttc ggtattgatg cagttgttct    7380
tgaccctaac actggtgaag aacttaacac cagccacgca gagggtgtcc ttgccgtcaa    7440
agctgcatgg ccatcatttg caagaactat ttggaaaaat catgataggt atctagacac    7500
ttatttgaac ccttaccctg ctactatttt cactggtgat ggtgctgcaa aggataagga    7560
tggttatatc tggattttgg gtcgtgtaga cgatgtggtg aacgtctctg gtcaccgtct    7620
gtctaccgct gaaattgagg ctgctattat cgaagatcca attgtggccg agtgtgctgt    7680
tgtcggattc aacgatgact tgactggtca agcagttgct gcatttgtgg tgttgaaaaa    7740
caaatctagt tggtccaccg caacagatga tgaattacaa gatatcaaga agcatttggt    7800
ctttactgtt agaaaagaca tcgggccatt tgccgcacca aaattgatca ttttagtgga    7860
tgacttgccc aagacaagat ccggcaaaat tatgagacgt attttaagaa aaatcctagc    7920
aggagaaagt gaccaactag cgacgttttc tacattgtca aaccctggca ttgttagaca    7980
tctaattgat tcggtcaagt tgtaacttaa gcgcgcgaat ttcttatgat ttatgatttt    8040
tattattaaa taagttataa aaaaaataag tgtatacaaa tttaaagtg actcttaggt    8100 tttaaaacga aaattcttat tcttgagtaa ctctttcctg taggtcaggt tgctttctca    8160
ggtatagcat gaggtcgctc ttattgacca cacctctacc ggcatgccga gcaaatgcct    8220
gcaaatcgct ccccatttca cccaattgta gatatgctaa ctccagcaat gagttgatga    8280
atctcggtgt gtattttatg tcctcagagg acaacacctg ttgtaatcgt tcttccacac    8340
gtacgtttta aacagttgat gagaaccttt ttcgcaagtt caaggtgctc taattttaa     8400 aattttact tttcgcgaca caataaagtc ttcacgacgc taaactatta gtgcacataa     8460
tgtagttact tggacgctgt tcaataatgt ataaaattta tttcctttgc attacgtaca    8520
ttatataacc aaatcttaaa aatatagaaa tatgatatgt gtataataat ataagcaaaa    8580
tttacgtatc tttgcttata atatagcttt aatgttcttt aggtatatat ttaagagcga    8640
tttgtctcga cttatttctt tttttgagag aaaaattggt tctctacagc agaaatgatg    8700
gcaggtacaa cttctgggtt ggccaaagta gttaggtcac ctagctgttc ggcttcgtta    8760
gaagcaacct ttcttagaac tcttctcata atctttcctg accttgttct tggtagatct    8820
ctaactagaa taatggtttt tggtgaggcg aaaggaccaa tctcacccct aacttgtaag    8880
atcaattctc tacgtaaatt atctggtgtg atgtgttctg catcaccttc agtagcgttg    8940
ttttgtagat aaccatcttt tagggaaaca tatgcaacga cggttgacc ggtcaattca     9000 tctggaatac cgacaacagc agcttccgag acgttttcgt gatttgagat agatgcttca    9060
atttctgatg tggataatct atgaccggaa acatttacaa cgtcgtcaac tctacccctg    9120
```

-continued

```
atccagtagt aaccatcatg atctctacca gcaccatcac ctgtgaaata gtgaccagga    9180
taaggtttca agtaagtatc catgtaacgg tcgtggtggt tccaaacaga tctagccatt    9240
gatggccatg gtgatttaac ggcaaggaca ccttcgacat cattaccttc taattccaca    9300
cctgtaacag ggtcaatgat acaagcgtta ataccaaaga atggcacggt agcagaacca    9360
ggttttgttg ggacagcacc tgccaaagga gcaattaaat gagaaccaga ctctgtttgc    9420
cacatagtgt cacaaatgac acagtttttg ttacccactt tttcatgata ccattcccat    9480
aagtctggag agattggttc accgacggaa cccaagacac gtaatgagga agtgtcatat    9540
ttggcaattt cggcttcacc tacacgtttg attaatctta aagcagttgg agccacatag    9600
aaatgggtag ccttgtgacg ttggataatt ctccaatatc taccataatc tgggtaggca    9660
ggagtggatt cgaaaattat tgaggcggta cccaaggtta atggaccata tagagcatag    9720
gtgtgacccg tgatccagcc gacgtcaccg gcagtgaaga aacatcttc tgggtgaata    9780 tcaaaaacgt atctagttgt taaagcggca cctaataaat aaccacctgt agtgtgaacg    9840 acacccttg gagaaccagt ggaaccggaa gtgtataata aaaatagagg atcttcagcg    9900
tcacatgaaa caggaggtag gtaagttctc tgcttagcgg cctcctcatg ccaccagtaa    9960
tctctaccgg ccttcattgg aataccttca gtaccagttc tttggaaaac caagatacgg   10020
gaaaccaaat cgactccgtt caaaccttcg tcaacaattt ttttagtgtt gatggtctta   10080
ccacctcttt taccttcatc acaagtgatg accactttag aattagcgtc aacgacacga   10140
tctttcaacg aaccagcgga gaacccagca aagacaacag agtgaatagc accaatacga   10200
gccacagcca acatagcaat gaccgcttct ggaatcattg gcaaatagat agccactgtg   10260 tcaccttct taacgcccca gcttttttaag acaccagcga tttgggaaac ttttctgagt   10320
aattcaccaa atgtgatgat tttgttgtcg gattcgtcat cagcttcata gatcaaagct   10380
ggcttgtcgg gattagcaaa ggcatgtctg tcaacacaat tgtatgatgc attcaattta   10440
ccgttcaaaa accatgcaac atcaccattg ttcaatgaac cagattgaac tttggtgtat   10500
ggagcatccc aatgcaagta ttccttagcc atcttatcaa agaattttc tggctcattg   10560 atagattgtt gatacatttc ttgataatgt tgcatatcag taacgtaacc cttgccgggt   10620
tggctgttgt aaaaatgttg aggagcctta agagccttta cgttgtgagc ttcataaact   10680
actttatgtt ccttgattgt cattttctgc agtctagata tatttgttgt aaaaagtaga   10740
taattacttc cttgatgatc tgtaaaaaag agaaaaagaa agcatctaag aacttgaaaa   10800
actacgaatt agaaaagacc aaatatgtat ttcttgcatt gaccaattta tgcaagttta   10860
tatatatgta aatgtaagtt tcacgaggtt ctactaaact aaaccacccc cttggttaga   10920
agaaaagagt gtgtgagaac aggctgttgt tgtcacacga ttcggacaat tctgtttgaa   10980
agagagagag taacagtacg atcgaacgaa cttttgctctg gagatcacag tgggcatcat   11040
agcatgtggt actaaaccct ttcccgccat tccagaacct tcgattgctt gttacaaaac   11100
ctgtgagccg tcgctaggac cttgttgtgt gacgaaattg gaagctgcaa tcaataggaa   11160
gacaggaagt cgagcgtgtc tgggttttt cagtttttgtt cttttttgcaa acaaatcacg   11220 agcgacggta atttctttct cgataagagg ccacgtgctt tatgagggta acatcaattc   11280
aagaaggagg gaaacacttc cttttttctgg ccctgataat agtatgaggg tgaagccaaa   11340
ataaaggatt cgcgcccaaa tcggcatctt taaatgcagg tatgcgatag ttcctcactc   11400
tttccttact cacgagtaat tcttgcaaat gcctattatg cagatgttat aatatctgtg   11460
```

```
cgtcttgagt tgaagagctc gagactagat gcatgctcga gcggccgcca gtgtgatgga    11520
tatctgcaga attcgccctt tgggccctg tacacctagg atccgtcgac actggatggc    11580
ggcgttagta tcgaatcgac agcagtatag cgaccagcat tcacatacga ttgacgcatg    11640
atattacttt ctgcgcactt aacttcgcat ctgggcagat gatgtcgagg cgaaaaaaaa    11700
tataaatcac gctaacattt gattaaaata gaacaactac aatataaaaa aactatacaa    11760
atgacaagtt cttgaaaaca agaatctttt tattgtcagt actgattaga aaaactcatc    11820
gagcatcaaa tgaaactgca atttattcat atcaggatta tcaataccat attttgaaa     11880 aagccgtttc tgtaatgaag gagaaaactc accgaggcag ttccatagga tggcaagatc    11940
ctggtatcgg tctgcgattc cgactcgtcc aacatcaata caacctatta atttccctc     12000 gtcaaaaata aggttatcaa gtgagaaatc accatgagtg acgactgaat ccggtgagaa    12060
tggcaaaagc ttatgcattt cttccagac ttgttcaaca ggccagccat tacgctcgtc     12120
atcaaaatca ctcgcatcaa ccaaaccgtt attcattcgt gattgcgcct gagcgagacg    12180
aaatacgcga tcgctgttaa aaggacaatt acaaacagga atcgaatgca accggcgcag    12240
gaacactgcc agcgcatcaa caatattttc acctgaatca ggatattctt ctaatacctg    12300
gaatgctgtt ttgccgggga tcgcagtggt gagtaaccat gcatcatcag                12350
```

<210> SEQ ID NO 21
<211> LENGTH: 1120
<212> TYPE: DNA
<213> ORGANISM: Artificial
<220> FEATURE:
<223> OTHER INFORMATION: nucleotide seqeunce encoding E.coli gldA
      codon-optimised for yeast

<400> SEQUENCE: 21

```
ctgcagaaaa tggacagaat catccaatct ccaggtaagt acatccaagg tgctgacgtt      60
atcaacagat gggtgaata cttgaagcca ttggctgaaa gatggttggt tgttggtgac      120
aagttcgttt tgggtttcgc tcaatctacc gttgaaaagt ctttcaagga cgctggtttg     180
gttgttgaaa tcgctccatt cggtggtgaa tgttctcaaa acgaaatcga cagattgaga     240
ggtatcgctg aaaccgctca atgtggtgct atccttggta tcggtggtgg taagaccttg     300
gacaccgcta aggctttggc tcacttcatg ggtgttccag ttgctatcgc tccaaccatc     360
gcttctaccg acgctccatg ttctgctttg tctgttatct acaccgacga aggtgaattc     420
gacagatact tgttgttgcc aaacaaccca aacatggtta tcgttgacac caagatcgtt     480
gctggtgctc cagctagatt gttggcagct ggtatcggtg acgctttggc tacctggttc     540
gaagctagag cttgttctag atctggtgct accaccatgg ctggtggtaa gtgtacccaa     600
gctgctttgg ctttggctga attgtgttac aacaccttgt ggaagaagg tgaaaaggct      660 atgttggctg ctgaacaaca cgttgttacc ccagctttgg aaagagttat cgaagctaac     720
acctacttgt ctggtgttgg tttcgaatct ggtggtttgg ctgctgctca cgctgttcac     780
aacggtttga ccgctatccc agacgctcac cactactacc acggtgaaaa ggttgctttc     840
ggtaccttga cccaattggt tttggaaaac gctccagttg aagaaatcga aacgttgct      900 gctttgtctc acgctgttgg tttgccaatc acctgtgctc aattggacat caaggaagac     960
gttccagcta agatgagaat cgttgctgaa gctgcttgtg ctgaaggtga aaccatccac    1020
aacatgccag tggtgctac cccagaccaa gttacgctg ctttgttggt tgctgaccaa     1080
tacggtcaaa gattcctaca agaatgggaa taaggcgcgc                           1120
```

<210> SEQ ID NO 22
<211> LENGTH: 1450
<212> TYPE: DNA
<213> ORGANISM: Artificial
<220> FEATURE:
<223> OTHER INFORMATION: DAK1 PCR fragment

<400> SEQUENCE: 22

| | | | | | |
|---|---|---|---|---|---|
| tctagaaaat | gtccgctaaa | tcgtttgaag | tcacagatcc | agtcaattca | agtctcaaag | 60 |
| ggtttgccct | tgctaacccc | tccattacgc | tggtccctga | agaaaaaatt | ctcttcagaa | 120 |
| agaccgattc | cgacaagatc | gcattaattt | ctggtggtgg | tagtggacat | gaacctacac | 180 |
| acgccggttt | cattggtaag | ggtatgttga | gtggcgccgt | ggttggcgaa | atttttgcat | 240 |
| ccccttcaac | aaaacagatt | ttaaatgcaa | tccgtttagt | caatgaaaat | gcgtctggcg | 300 |
| ttttattgat | tgtgaagaac | tacacaggtg | atgttttgca | ttttggtctg | tccgctgaga | 360 |
| gagcaagagc | cttgggtatt | aactgccgcg | ttgctgtcat | aggtgatgat | gttgcagttg | 420 |
| gcagagaaaa | gggtggtatg | gttggtagaa | gagcattggc | aggtaccgtt | ttggttcata | 480 |
| agattgtagg | tgccttcgca | gaagaatatt | ctagtaagta | tggcttagac | ggtacagcta | 540 |
| aagtggctaa | aattatcaac | gacaatttgg | tgaccattgg | atcttcttta | gaccattgta | 600 |
| aagttcctgg | caggaaattc | gaaagtgaat | taaacgaaaa | acaaatggaa | ttgggtatgg | 660 |
| gtattcataa | cgaacctggt | gtgaaagttt | tagaccctat | tccttctacc | gaagacttga | 720 |
| tctccaagta | tatgctacca | aaactattgg | atccaaacga | taaggataga | gcttttgtaa | 780 |
| agtttgatga | agatgatgaa | gttgtcttgt | tagttaacaa | tctcggcggt | gtttctaatt | 840 |
| ttgttattag | ttctatcact | tccaaaacta | cggatttctt | aaaggaaaat | tacaacataa | 900 |
| ccccggttca | aacaattgct | ggcacattga | tgacctcctt | caatggtaat | gggttcagta | 960 |
| tcacattact | aaacgccact | aaggctacaa | aggctttgca | atctgatttt | gaggagatca | 1020 |
| aatcagtact | agacttgttg | aacgcattta | cgaacgcacc | gggctggcca | attgcagatt | 1080 |
| ttgaaaagac | ttctgcccca | tctgttaacg | atgacttgtt | acataatgaa | gtaacagcaa | 1140 |
| aggccgtcgg | tacctatgac | tttgacaagt | ttgctgagtg | gatgaagagt | ggtgctgaac | 1200 |
| aagttatcaa | gagcgaaccg | cacattacgg | aactagacaa | tcaagttggt | gatggtgatt | 1260 |
| gtggttacac | tttagtggca | ggagttaaag | gcatcaccga | aaaccttgac | aagctgtcga | 1320 |
| aggactcatt | atctcaggcg | gttgcccaaa | tttcagattt | cattgaaggc | tcaatgggag | 1380 |
| gtacttctgg | tggtttatat | tctattcttt | tgtcgggttt | ttcacacgga | ttaattcagg | 1440 |
| tttgtaaatc | | | | | | 1450 |

<210> SEQ ID NO 23
<211> LENGTH: 1698
<212> TYPE: DNA
<213> ORGANISM: Artificial
<220> FEATURE:
<223> OTHER INFORMATION: GUP1 PCR fragment

<400> SEQUENCE: 23

| | | | | | |
|---|---|---|---|---|---|
| gaattcaaaa | tgtcgctgat | cagcatcctg | tctcccctaa | ttacttccga | gggcttagat | 60 |
| tcaagaatca | aaccttcacc | aaaaaaggat | gcctctacta | ccactaagcc | atcactatgg | 120 |
| aaaactactg | agttcaaatt | ctactacatt | gcatttctgg | tcgtggttcc | cttgatgttc | 180 |
| tatgctgggt | tacaagctag | ttcgcccgaa | aatccaaact | atgcaagata | cgaacgtctc | 240 |
| ctatctcaag | gttggttatt | tggcagaaaa | gtagacaata | gtgattctca | atataggttt | 300 |

| | |
|---|---:|
| ttcagggaca attttgcgct attgtcagtt ttaatgctag tccacacttc tataaaacgc | 360 |
| attgtacttt attcaacaaa tatcactaaa ttgaggtttg atctgatatt tggtttgatc | 420 |
| tttttagtgg ccgctcatgg tgtcaattcg ataagaattt tagcccatat gctaatttta | 480 |
| tatgccatcg cccatgtact aaagaacttt agaagaatag ccaccatcag catttggatt | 540 |
| tatggtattt ctacgctttt tattaacgac aacttcagag catatccatt tggtaatatt | 600 |
| tgctcttttt taagcccatt ggaccattgg tatagaggta tcattccaag atgggatgtc | 660 |
| tttttcaatt ttactctttt gagagtctta agttacaact tggacttctt agagaggtgg | 720 |
| gagaatttac aaaagaagaa aagtccatcc tatgaatcaa aagaagctaa atcagccatt | 780 |
| ttgctcaatg aacgtgctag attaactgct gcacacccca tacaggacta cagcttaatg | 840 |
| aattatattg catatgttac ttcacacgcca cttttcattg ccggcccat tataacattc | 900 |
| aatgattatg tttaccaatc gaaacatacc ttgccatcaa taaatttcaa attcattttt | 960 |
| tactatgcgg tgagattcgt tattgctctc ttatctatgg agttcatttt acactttctc | 1020 |
| cacgttgtgg caatctcaaa aaccaaagcg tgggaaaatg acacaccttt ccagatttcc | 1080 |
| atgattggct tatttaattt gaatattatt tggctaaaac tactgattcc gtggaggctg | 1140 |
| tttaggctgt gggctttgct agacggaatc gatacacctg aaaatatgat caggtgtgtt | 1200 |
| gataacaatt acagttcact agcattctgg agagcttggc atagaagcta caataagtgg | 1260 |
| gttgtccgtt acatatatat tcctctaggt ggttcaaaaa atagagtttt gacatcacta | 1320 |
| gcagtctttt ccttcgtagc tatatggcat gacatcgaac taaagttatt attatggggt | 1380 |
| tggctaatag ttttgttcct cttaccagaa attttgcta cccaaatttt ctctcattat | 1440 |
| accgacgcag tctggtacag acacgtttgc gctgtcggtg ctgttttcaa catatgggtt | 1500 |
| atgatgatcg ctaatctttt tggattctgc ttgggctctg acggtactaa aaaattacta | 1560 |
| agcgatatgt tctgtaccgt atctggtttc aaatttgtaa ttttggcaag cgttagttta | 1620 |
| ttcatcgcag tacaaataat gtttgaaatc agagaagaag aaaagaggca cggaatttac | 1680 |
| ctaaaatgct gaggatcc | 1698 |

<210> SEQ ID NO 24
<211> LENGTH: 3037
<212> TYPE: DNA
<213> ORGANISM: Artificial
<220> FEATURE:
<223> OTHER INFORMATION: FPS1 PCR fragment

<400> SEQUENCE: 24

| | |
|---|---:|
| aagagctccg gactagtcgt acgaattcta tccttttgtt gtttccgggt gtacaatatg | 60 |
| gacttcctct tttctggcaa ccaaacccat acatcgggat tcctataata ccttcgttgg | 120 |
| tctccctaac atgtaggtgg cggaggggag atatacaata gaacagatac cagacaagac | 180 |
| ataatgggct aaacaagact acaccaatta cactgcctca ttgatggtgg tacataacga | 240 |
| actaatactg tagccctaga cttgatagcc atcatcatat cgaagtttca ctacccttt | 300 |
| tccatttgcc atctattgaa gtaataatag gcgcatgcaa cttctttct ttttttttct | 360 |
| tttctctctc ccccgttgtt gtctcaccat atccgcaatg acaaaaaaat gatggaagac | 420 |
| actaaaggaa aaaattaacg acaaagacag caccaacaga tgtcgttgtt ccagagctga | 480 |
| tgaggggtat ctcgaagcac acgaaacttt ttccttcctt cattcacgca cactactctc | 540 |
| taatgagcaa cggtatacgg ccttccttcc agttacttga atttgaaata aaaaaagttt | 600 |

```
gctgtcttgc tatcaagtat aaatagacct gcaattatta atcttttgtt tcctcgtcat    660
tgttctcgtt ccctttcttc cttgtttctt tttctgcaca atatttcaag ctataccaag    720
catacaatca actccagctg cattaaaatg agtaatcctc aaaaagctct aaacgacttt    780
ctgtccagtg aatctgttca tacacatgat agttctagga acaatctaa taagcagtca    840
tccgacgaag gacgctcttc atcacaacct tcacatcatc actctggtgg tactaacaac    900
aataataaca ataataataa taataataac agtaacaaca caacaacgg caacgatggg    960
ggaaatgatg acgactatga ttatgaaatg caagattata gaccttctcc gcaaagtgcg   1020
cggcctactc ccacgtatgt tccacaatat tctgtagaaa gtgggactgc tttcccgatt   1080
caagaggtta ttcctagcgc atacattaac acacaagata taaaccataa agataacggt   1140
ccgccgagtg caagcagtaa tagagcattc aggcctagag ggcagaccac agtgtcggcc   1200
aacgtgctta acattgaaga ttttttacaaa aatgcagacg atgcgcatac catcccggag   1260
tcacatttat cgagaaggag aagtaggtcg agggctacga gtaatgctgg gcacagtgcc   1320
aatacaggcg ccacgaatgg caggactact ggtgcccaaa ctaatatgga aagcaatgaa   1380
tcaccacgta acgtccccat tatggtgaag ccaaagacat tataccagaa ccctcaaaca   1440
cctacagtct tgccctccac ataccatcca attaataaat ggtcttccgt caaaaacact   1500
tatttgaagg aattttttagc cgagtttatg ggaacaatgg ttatgattat tttcggtagt   1560
gctgttgttt gtcaggtcaa tgttgctggg aaaatacagc aggacaattt caacgtggct   1620
ttggataacc ttaacgttac cgggtcttct gcagaaacga tagacgctat gaagagttta   1680
acatccttgg tttcatccgt tgcgggcggt accttggatg atgtggcatt gggctgggct   1740
gctgccgtgg tgatgggcta tttctgcgct ggtggtagtg ccatctcagg tgctcatttg   1800
aatccgtcta ttacattagc caatttggtg tatagaggtt ttcccctgaa gaaagttcct   1860
tattactttg ctggacaatt gatcggtgcc ttcacaggcg cttgatctt gtttatttgg   1920
tacaaaaggg tgttacaaga ggcatatagc gattggtgga tgaatgaaag tgttgcggga   1980
atgttttgcg ttttttccaaa gccttatcta agttcaggac ggcaattttt ttccgaattt   2040
ttatgtggag ctatgttaca agcaggaaca tttgcgctga ccgatcctta tacgtgtttg   2100
tcctctgatg ttttcccatt gatgatgttt attttgattt tcattatcaa tgcttccatg   2160
gcttatcaga caggtacagc aatgaatttg gctcgtgatc tgggcccacg tcttgcacta   2220
tatgcagttg gatttgatca taaaatgctt tgggtgcatc atcatcattt cttttgggtt   2280
cccatggtag gcccatttat tggtgcgtta atgggggggt tggtttacga tgtctgtatt   2340
tatcagggtc atgaatctcc agtcaactgg tctttaccag tttataagga aatgattatg   2400
agagcctggt ttagaaggcc tggttggaag aagagaaata gagcaagaag aacatcggac   2460
ctgagtgact tctcatacaa taacgatgat gatgaggaat ttggagaaag aatggctctt   2520
caaaagacaa agaccaagtc atctatttca gacaacgaaa atgaagcagg agaaaagaaa   2580
gtgcaattta atctgttca gcgcggcaaa agaacgtttg gtggtatacc aacaattctt   2640
gaagaagaag attccattga aactgcttcg ctaggtgcga cgacgactga ttctattggg   2700
ttatccgaca catcatcaga agattcgcat tatggtaatg ctaagaaggt aacatgagga   2760
tccccttttc ctttgtcgat atcatgtaat tagttatgtc acgcttacat tcacgccctc   2820
ctcccacatc cgctctaacc gaaaaggaag gagttagaca acctgaagtc taggtcccta   2880
tttatttttt ttaatagtta tgttagtatt aagaacgtta tttatatttc aaattttttct   2940
tttttttctg tacaaacgcg tgtacgcatg taacattata ctgaaaacct tgcttgagaa   3000
```
ggttttggga cgctcgaagg cttcctaggc tcgagtt                                    3037

<210> SEQ ID NO 25
<211> LENGTH: 552
<212> TYPE: PRT
<213> ORGANISM: Citrobacter freundii

<400> SEQUENCE: 25

Met Ser Gln Phe Phe Asn Gln Arg Thr His Leu Val Ser Asp Val
1               5                   10                  15

Ile Asp Gly Thr Ile Ile Ala Ser Pro Trp Asn Asn Leu Ala Arg Leu
                20                  25                  30

Glu Ser Asp Pro Ala Ile Arg Ile Val Val Arg Arg Asp Leu Asn Lys
            35                  40                  45

Asn Asn Val Ala Val Ile Ser Gly Gly Ser Gly His Glu Pro Ala
    50                  55                  60

His Val Gly Phe Ile Gly Lys Gly Met Leu Thr Ala Ala Val Cys Gly
65                  70                  75                  80

Asp Val Phe Ala Ser Pro Ser Val Asp Ala Val Leu Thr Ala Ile Gln
                85                  90                  95

Ala Val Thr Gly Glu Ala Gly Cys Leu Leu Ile Val Lys Asn Tyr Thr
            100                 105                 110

Gly Asp Arg Leu Asn Phe Gly Leu Ala Ala Glu Lys Ala Arg Arg Leu
        115                 120                 125

Gly Tyr Asn Val Glu Met Leu Ile Val Gly Asp Asp Ile Ser Leu Pro
    130                 135                 140

Asp Asn Lys His Pro Arg Gly Ile Ala Gly Thr Ile Leu Val His Lys
145                 150                 155                 160

Ile Ala Gly Tyr Phe Ala Glu Arg Gly Tyr Asn Leu Ala Thr Val Leu
                165                 170                 175

Arg Glu Ala Gln Tyr Ala Ala Asn Asn Thr Phe Ser Leu Gly Val Ala
            180                 185                 190

Leu Ser Ser Cys His Leu Pro Gln Glu Ala Asp Ala Ala Pro Arg His
        195                 200                 205

His Pro Gly His Ala Glu Leu Gly Met Gly Ile His Gly Glu Pro Gly
    210                 215                 220

Ala Ser Val Ile Asp Thr Gln Asn Ser Ala Gln Val Val Asn Leu Met
225                 230                 235                 240

Val Asp Lys Leu Met Ala Ala Leu Pro Glu Thr Gly Arg Leu Ala Val
                245                 250                 255

Met Ile Asn Asn Leu Gly Gly Val Ser Val Ala Glu Met Ala Ile Ile
            260                 265                 270

Thr Arg Glu Leu Ala Ser Ser Pro Leu His Pro Arg Ile Asp Trp Leu
        275                 280                 285

Ile Gly Pro Ala Ser Leu Val Thr Ala Leu Asp Met Lys Ser Phe Ser
    290                 295                 300

Leu Thr Ala Ile Val Leu Glu Glu Ser Ile Glu Lys Ala Leu Leu Thr
305                 310                 315                 320

Glu Val Glu Thr Ser Asn Trp Pro Thr Pro Val Pro Pro Arg Glu Ile
                325                 330                 335

Ser Cys Val Pro Ser Ser Gln Arg Ser Ala Arg Val Glu Phe Gln Pro
            340                 345                 350

Ser Ala Asn Ala Met Val Ala Gly Ile Val Glu Leu Val Thr Thr Thr
        355                 360                 365

```
Leu Ser Asp Leu Glu Thr His Leu Asn Ala Leu Asp Ala Lys Val Gly
    370                 375                 380

Asp Gly Asp Thr Gly Ser Thr Phe Ala Ala Gly Ala Arg Glu Ile Ala
385                 390                 395                 400

Ser Leu Leu His Arg Gln Gln Leu Pro Leu Asp Asn Leu Ala Thr Leu
            405                 410                 415

Phe Ala Leu Ile Gly Glu Arg Leu Thr Val Val Met Gly Gly Ser Ser
            420                 425                 430

Gly Val Leu Met Ser Ile Phe Phe Thr Ala Ala Gly Gln Lys Leu Glu
            435                 440                 445

Gln Gly Ala Ser Val Ala Glu Ser Leu Asn Thr Gly Leu Ala Gln Met
    450                 455                 460

Lys Phe Tyr Gly Gly Ala Asp Glu Gly Asp Arg Thr Met Ile Asp Ala
465                 470                 475                 480

Leu Gln Pro Ala Leu Thr Ser Leu Leu Thr Gln Pro Gln Asn Leu Gln
            485                 490                 495

Ala Ala Phe Asp Ala Ala Gln Ala Gly Ala Glu Arg Thr Cys Leu Ser
            500                 505                 510

Ser Lys Ala Asn Ala Gly Arg Ala Ser Tyr Leu Ser Ser Glu Ser Leu
    515                 520                 525

Leu Gly Asn Met Asp Pro Gly Ala His Ala Val Ala Met Val Phe Lys
    530                 535                 540

Ala Leu Ala Glu Ser Glu Leu Gly
545                 550

<210> SEQ ID NO 26
<211> LENGTH: 1678
<212> TYPE: DNA
<213> ORGANISM: Artificial
<220> FEATURE:
<223> OTHER INFORMATION: nucleotide sequence encoding the C. freundii
      dhaK codon-optimised for yeast

<400> SEQUENCE: 26
tctagaaaaa tgtctcaatt cttcttcaac cagagaaccc acttggtttc tgacgttatc      60
gacggtgcta tcatcgcttc accatggaac aatttggcta gattggaatc tgacccagct     120
atcagaatcg ttgttagaag agacttgaac aagaacaacg ttgctgttat ctctggtggt     180
ggttctggtc acgaaccagc tcacgttggt ttcatcggta agggtatgtt gaccgctgct     240
gtttgtggtg acgttttcgc ttctccatct gttgacgctg ttttgactgc tatccaagct     300
gttaccggtg aagctggttg tttgttgatc gttaagaact acaccggtga cagattgaac     360
ttcggtttgg ctgctgaaaa ggctagaaga ttgggttaca cgttgaaatg ttgatcgtt     420 ggtgacgaca tctctttgcc agacaacaag cacccaagag gtatcgctgg taccatcttg     480
gttcacaaga tcgctggtta cttcgctgaa agaggttaca cttagctac cgttttgaga     540 gaagctcaat acgctgcttc taacaccttc tctttgggtg ttgctttgtc ttcttgtcac     600
ttgccacaag aaaccgacgc tgctccaaga caccacccag gtcacgctga attgggtatg     660
ggtatccacg tgaaccaggt gcttctgtt atcgacaccc aaaactctgc tcaagttgtt     720
aacttgatgg ttgacaagtt gttggctgct tgccagaaa ccggtagatt ggctgttatg     780
atcaacaact gggtggtgt ttctgttgct gaaatggcta tcatcaccag agaattggct     840
tcttctccat gcactcaag aatcgactgg ttgatcggtc cagcttcttt ggtaaccgct     900
ttggacatga agggtttctc tttgaccgct atcgttttgg aagaatctat cgaaaaggct     960
```

```
ttgttgaccg aagttgaaac ctctaactgg ccaaccccag ttccaccaag agaaatcacc    1020
tgtgttgttt cttctcacgc ttctgctaga gttgaattcc aaccatctgc taacgctttg    1080
gttgctggta tcgttgaatt ggttaccgct accttgtctg acttggaaac ccacttgaac    1140
gctttggacg ctaaggttgg tgacggtgac accggttcta ccttcgctgc tgctgctaga    1200
gaaatcgctt ctttgttgca cagacaacaa ttgccattga caacttggc taccttgttc    1260 gctttgatcg gtgaaagatt gaccgttgtt atgggtggtt cttctggtgt tttgatgtct    1320
atcttcttca ccgctgctgg tcaaaagttg aacaaggtg ctaacgttgt tgaagctttg    1380
aacaccggtt tggctcaaat gaagttctac ggtggtgctg acgaaggtga cagaaccatg    1440
atcgacgctt tgcaaccagc tttgacctct ttgttggctc aaccaaagaa cttgcaagct    1500
gctttcgacg ctgctcaagc tggtgctgaa agaacctgtt tgtcttctaa ggctaacgct    1560
ggtagagctt cttacttgtc ttctgaatct ttgttgggta acatggaccc aggtgctcaa    1620
agattggcta tggttttcaa ggctttggct gaatctgaat gggttaata aggtcgac     1678

<210> SEQ ID NO 27
<211> LENGTH: 2951
<212> TYPE: DNA
<213> ORGANISM: Artificial
<220> FEATURE:
<223> OTHER INFORMATION: pRNdhaK

<400> SEQUENCE: 27
ggatccacta gtaacggccg ccagtgtgct ggaattcgcc cttctcgagc ttaagacgcg      60
tttcttcttc agattccctc atggagaaag tgcggcagat gtatatgaca gagtcgccag     120
tttccaagag actttattca ggcacttcca tgataggcaa gagagaagac ccagagatgt     180
tgttgtccta gttacacatg gtatttattc cagagtattc ctgatgaaat ggtttagatg     240
gacatacgaa gagtttgaat cgtttaccaa tgttcctaac gggagcgtaa tggtgatgga     300
actggacgaa tccatcaata gatacgtcct gaggaccgtg ctacccaaat ggactgattg     360
tgagggagac ctaactacat agtgtttaaa gattacggat atttaactta cttagaataa     420
tgccattttt ttgagttata ataatcctac gttagtgtga gcgggattta aactgtgagg     480
accttaatac attcagacac ttctgcggta tcaccctact tattcccttc gagattatat     540
ctaggaaccc atcaggttgg tggaagatta cccgttctaa acttttcag cttcctctat     600 tgatgttaca cctggacacc ccttttctgg catccagttt ttaatcttca gtggcatgtg     660
agattctccg aaattaatta aagcaatcac acaattctct cggataccac ctcggttgaa     720
actgacaggt ggtttgttac gcatgctaat gcaaggagc ctatatacct ttggctcggc     780
tgctgtaaca gggaatataa agggcagcat aatttaggag tttagtgaac ttgcaacatt     840
tactattttc ccttcttacg taaatatttt tcttttaat tctaaatcaa tctttttcaa     900
ttttttgttt gtattctttt cttgcttaaa tctataacta caaaaacac atacataaat     960 ctagaaaaat gtctcaattc ttcttcaacc agagaaccca cttggtttct gacgttatcg    1020
acggtgctat catcgcttca ccatggaaca atttggctag attggaatct gacccagcta    1080
tcagaatcgt tgttagaaga gacttgaaca agaacaacgt tgctgttatc tctggtggtg    1140
gttctggtca cgaaccagct cacgttggtt tcatcggtaa gggtatgttg accgctgctg    1200
tttgtggtga cgttttcgct tctccatctg ttgacgctgt tttgactgct atccaagctg    1260
ttaccggtga agctggttgt ttgttgatcg ttaagaacta caccggtgac agattgaact    1320
```

```
tcggtttggc tgctgaaaag gctagaagat tgggttacaa cgttgaaatg ttgatcgttg      1380
gtgacgacat ctctttgcca gacaacaagc acccaagagg tatcgctggt accatcttgg      1440
ttcacaagat cgctggttac ttcgctgaaa gaggttacaa cttagctacc gttttgagag      1500
aagctcaata cgctgcttct aacaccttct ctttgggtgt tgctttgtct tcttgtcact      1560
tgccacaaga aaccgacgct gctccaagac accacccagg tcacgctgaa ttgggtatgg      1620
gtatccacgg tgaaccaggt gcttctgtta tcgacaccca aaactctgct caagttgtta      1680
acttgatggt tgacaagttg ttggctgctt tgccagaaac cggtagattg gctgttatga      1740
tcaacaactt gggtggtgtt tctgttgctg aaatggctat catcaccaga gaattggctt      1800
cttctccatt gcactcaaga atcgactggt tgatcggtcc agcttctttg gtaaccgctt      1860
tggacatgaa gggtttctct ttgaccgcta tcgttttgga agaatctatc gaaaaggctt      1920
tgttgaccga agttgaaacc tctaactggc aaccccagt tccaccaaga gaaatcacct      1980
gtgttgtttc ttctcacgct tctgctagag ttgaattcca accatctgct aacgctttgg      2040
ttgctggtat cgttgaattg gttaccgcta ccttgtctga cttggaaacc cacttgaacg      2100
cttttggacgc taaggttggt gacggtgaca ccggttctac cttcgctgct gctgctagag      2160
aaatcgcttc tttgttgcac agacaacaat gccattgaa caacttggct accttgttcg      2220
ctttgatcgg tgaaagattg accgttgtta tgggtggttc ttctggtgtt ttgatgtcta      2280
tcttcttcac cgctgctggt caaaagttgg aacaaggtgc taacgttgtt gaagctttga      2340
acaccggttt ggctcaaatg aagttctacg gtggtgctga cgaaggtgac agaaccatga      2400
tcgacgcttt gcaaccagct ttgacctctt tgttggctca accaagaac ttgcaagctg      2460
cttcgacgc tgctcaagct ggtgctgaaa gaacctgttt gtcttctaag gctaacgctg      2520
gtagagcttc ttacttgtct tctgaatctt tgttgggtaa catggaccca ggtgctcaaa      2580
gattggctat ggtttcaag gctttggctg aatctgaatt gggttaataa ggtcgagaca      2640
aatcgctctt aaatatatac ctaaagaaca ttaaagctat attataagca aagatacgta      2700
aattttgctt atattattat acacatatca tatttctata tttttaagat tggttatat      2760
aatgtacgta atgcaaagga aataaatttt tatacattat gaacagcgtc caagtaacta      2820
cattatgtgc actaatagtt tagcgtcgtg aagactttat tgtgtcgcga aaagtaaaaa      2880
ttttaaaaat tagagcacct tgaacttgcg aaaaaggttc tcatcaactg ttttaaaacgt      2940
acgaagctta a                                                         2951

<210> SEQ ID NO 28
<211> LENGTH: 1949
<212> TYPE: DNA
<213> ORGANISM: Artificial
<220> FEATURE:
<223> OTHER INFORMATION: pRNgldA

<400> SEQUENCE: 28
actagtaaat gtgtgggaa gcgggtaagc tgccacagca attaatgcac aacatttaac       60
ctacattctt ccttatcgga tcctcaaaac ccttaaaaac atatgcctca ccctaacata      120
ttttccaatt aaccctcaat atttctctgt caccgggcct ctattttcca ttttcttctt      180
tacccgccac gcgttttttt ctttcaaatt ttttcttcc ttcttctttt cttccacgt       240
cctcttgcat aaataaataa accgttttga aaccaaactc gcctctctct ctccttttg      300
aaatattttt gggtttgttt gatccttccc ttccaatct ctcttgttta atatattc       360
atttatatca cgctctcttt ttatcttcct tttttcctc tctcttgtat tcttccttcc      420
```

```
cctttctact caaaccaaga agaaaaagaa aaggtcaatc tttgttaaag aataggatct    480
tctactacat cagcttttag attttcacg cttactgctt ttttcttccc aagatcgaaa    540
atttactgaa ttaactgcag aaaatggaca gaatcatcca atctccaggt aagtacatcc    600
aaggtgctga cgttatcaac agattgggtg aatacttgaa gccattggct gaaagatggt    660
tggttgttgg tgacaagttc gttttgggtt tcgctcaatc taccgttgaa aagtctttca    720
aggacgctgg tttggttgtt gaaatcgctc cattcgtgg tgaatgttct caaaacgaaa    780
tcgacagatt gagaggtatc gctgaaaccg ctcaatgtgg tgctatcttg ggtatcggtg    840
gtggtaagac cttggacacc gctaaggctt tggctcactt catgggtgtt ccagttgcta    900
tcgctccaac catcgcttct accgacgctc catgttctgc tttgtctgtt atctacaccg    960
acgaaggtga attcgacaga tacttgttgt tgccaaacaa cccaaacatg ttatcgttg    1020 acaccaagat cgttgctggt gctccagcta gattgttggc agctggtatc ggtgacgctt    1080
tggctacctg gttcgaagct agagcttgtt ctagatctgg tgctaccacc atggctggtg    1140
gtaagtgtac ccaagctgct ttggctttgg ctgaattgtg ttacaacacc ttgttggaag    1200
aaggtgaaaa ggctatgttg gctgctgaac aacacgttgt taccccagct ttggaaagag    1260
ttatcgaagc taacacctac ttgtctggtg ttggtttcga atctggtggt ttggctgctg    1320
ctcacgctgt tcacaacggt ttgaccgcta tcccagacgc tcaccactac taccacggtg    1380
aaaaggttgc tttcggtacc ttgacccaat ggttttgga aaacgctcca gttgaagaaa    1440
tcgaaaccgt tgctgctttg tctcacgctg ttggtttgcc aatcaccttg gctcaattgg    1500
acatcaagga agacgttcca gctaagatga gaatcgttgc tgaagctgct tgtgctgaag    1560
gtgaaaccat ccacaacatg ccaggtggtg ctaccccaga ccaagtttac gctgctttgt    1620
tggttgctga ccaatacggt caaagattcc tacaagaatg ggaataaggc gcgcccttt    1680 tcctttgtcg atatcatgta attagttatg tcacgcttac attcacgccc tcctcccaca    1740
tccgctctaa ccgaaaagga aggagttaga caacctgaag tctaggtccc tatttatttt    1800
ttttaatagt tatgttagta ttaagaacgt tatttatat tcaaattttt ctttttttc    1860 tgtacaaacg cgtgtacgca tgtaacatta tactgaaaac cttgcttgag aaggttttgg    1920
gacgctcgaa ggcttcctag gcgtacgtt                                    1949
```

<210> SEQ ID NO 29
<211> LENGTH: 7690
<212> TYPE: DNA
<213> ORGANISM: Artificial
<220> FEATURE:
<223> OTHER INFORMATION: pRN558

<400> SEQUENCE: 29

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataattc cgttttaaga gcttggtgag cgctaggagt cactgccagg tatcgtttga    240
acacggcatt agtcagggaa gtcataacac agtcctttcc cgcaatttc ttttctatt     300 actcttggcc tcctctagta cactctatat ttttatgc ctcggtaatg attttcattt     360 tttttttcc acctagcgga tgactctttt tttttcttag cgattggcat tatcacataa     420
tgaattatac attatataaa gtaatgtgat ttcttcgaag aatatactaa aaaatgagca    480
```

```
ggcaagataa acgaaggcaa agatgacaga gcagaaagcc ctagtaaagc gtattacaaa      540
tgaaaccaag attcagattg cgatctcttt aaagggtggt cccctagcga tagagcactc      600
gatcttccca gaaaagagg cagaagcagt agcagaacag gccacacaat cgcaagtgat       660
taacgtccac acaggtatag ggtttctgga ccatatgata catgctctgg ccaagcattc      720
cggctggtcg ctaatcgttg agtgcattgg tgacttacac atagacgacc atcacaccac      780
tgaagactgc gggattgctc tcggtcaagc ttttaaagag gccctactgg cgcgtggagt      840
aaaaaggttt ggatcaggat ttgcgccttt ggatgaggca ctttccagag cggtggtaga      900
tctttcgaac aggccgtacg cagttgtcga acttggtttg caagggggaga agtaggaga      960 tctctcttgc gagatgatcc cgcatttttct tgaaagcttt gcagaggcta gcagaattac     1020
cctccacgtt gattgtctgc gaggcaagaa tgatcatcac cgtagtgaga gtgcgttcaa     1080
ggctcttgcg gttgccataa gagaagccac ctcgcccaat ggtaccaacg atgttccctc     1140
caccaaaggt gttcttatgt agtgacaccg attatttaaa gctgcagcat acgatatata     1200
tacatgtgta tatatgtata cctatgaatg tcagtaagta tgtatacgaa cagtatgata     1260
ctgaagatga caaggtaatg catcattcta tacgtgtcat tctgaacgag gcgcgctttc     1320
cttttttctt tttgctttt ctttttttt ctcttgaact cgacggatca tatgcggtgt      1380
gaaataccgc acagatgcgt aaggagaaaa taccgcatca ggaaattgta acgttaata      1440 ttttgttaaa attcgcgtta aattttttgtt aaatcagctc attttttaac caataggccg     1500
aaatcggcaa aatcccttat aaatcaaaag aatagaccga gatagggttg agtgttgttc     1560
cagtttggaa caagagtcca ctattaaaga acgtggactc caacgtcaaa gggcgaaaaa     1620
ccgtctatca gggcgatggc ccactacgtg aaccatcacc ctaatcaagt ttttttggggt     1680 cgaggtgccg taaagcacta atcggaacc ctaaagggag cccccgattt agagcttgac      1740
ggggaaagcc ggcattgcga ataccgcttc cacaaacatt gctcaaaagt atctctttgc     1800
tatatatctc tgtgctatat ccctatataa cctaccatc cacctttcgc tccttgaact      1860
tgcatctaaa ctcgacctct acatttttta tgtttatctc tagtattact ctttagacaa     1920
aaaaattgta gtaagaacta ttcatagagt gaatcgaaaa caatacgaaa atgtaaacat     1980
ttcctatacg tagtatatag agacaaaata gaagaaaccg ttcataattt tctgaccaat     2040
gaagaatcat caacgctatc actttctgtt cacaaagtat gcgcaatcca catcggtata     2100
gaatataatc ggggatgcct ttatcttgaa aaaatgcacc cgcagcttcg ctagtaatca     2160
gtaaacgcgg gaagtggagt caggcttttt ttatggaaga gaaaatagac accaaagtag     2220
ccttcttcta accttaacgg acctacagtg caaaaagtta tcaagagact gcattataga     2280
gcgcacaaag gagaaaaaaa gtaatctaag atgctttgtt agaaaaatag cgctctcggg     2340
atgcattttt gtagaacaaa aaagaagtat agattctttg ttggtaaaat agcgctctcg     2400
cgttgcattt ctgttctgta aaaatgcagc tcagattctt tgtttgaaaa attagcgctc     2460
tcgtcgcgtt gcattttttgt tttacaaaaa tgaagcacag attcttcgtt ggtaaaatag     2520
cgctttcgcg ttgcatttct gttctgtaaa aatgcagctc agattctttg tttgaaaaat     2580
tagcgctctc gcgttgcatt tttgttctac aaaatgaagc acagatgctt cgttaacaaa     2640
gatatgctat tgaagtgcaa gatggaaacg cagaaaatga accggggatg cgacgtgcaa     2700
gattacctat gcaatagatg caatagtttc tccaggaacc gaaatacata cattgtcttc     2760
cgtaaagcgc tagactatat attattatac aggttcaaat atactatctg tttcagggaa     2820
aactcccagg ttcggatgtt caaaattcaa tgatgggtaa caagtacgat cgtaaatctg     2880
```

```
taaaacagtt tgtcggatat taggctgtat ctcctcaaag cgtattcgaa tatcattgag    2940
aagctgcagc gtcacatcgg ataataatga tggcagccat tgtagaagtg ccttttgcat    3000
ttctagtctc tttctcggtc tagctagttt tactacatcg cgaagataga atcttagatc    3060
acactgcctt tgctgagctg atcaataga gtaacaaaag agtggtaagg cctcgttaaa    3120
ggacaaggac ctgagcggaa gtgtatcgta cagtagacgg agtatctagt atagtctata    3180
gtccgtggaa ttaattctca tctttgacag cttatcatcg ataatccgga gctagcatgc    3240
ggccgccagt gtgatggata tctgcagaat cgccctttt aagcttcgta cgtgtggaag    3300
aacgattaca acaggtgttg tcctctgagg acataaaata cacaccgaga ttcatcaact    3360
cattgctgga gttagcatat ctacaattgg gtgaaatggg gagcgatttg caggcatttg    3420
ctcggcatgc cggtagaggt gtggtcaata agagcgacct catgctatac ctgagaaagc    3480
aacctgacct acaggaaaga gttactcaag aataagaatt ttcgttttaa aacctaagag    3540
tcactttaaa atttgtatac acttattttt tttataactt atttaataat aaaaatcata    3600
aatcataaga aattcgcgcg cttaagcagc ttccaccagcc tttctagcca aagattgagc    3660
catcttttca gcggtagcca aagcagaaga ggtcataatg tccaagttac cagcgtaagc    3720
tggcaagtag tgagcagcac cttcaacttc caaccaaaca gcggtcttca aaccagagaa    3780
ttgaccaaca cctggcaagt taactggctt gtcttgtggg ataacttcga attgaactct    3840
ttgcttcaat ctgtaacctg gaacgtatgc ttgaacagct tcagccattt cgttgattga    3900
agcttcgatg tcgtcttgag atgcttcgtc agacaaaacg taaacggtgt ctctcatcat    3960
caatggtggt tcagctgggt tcaaaacgat gatagcctta cccttagcag caccaccaac    4020
aacttcgata gccctagagg tggtttcggt gaattcgtcg atgttagctc tggtacctgg    4080
accagcagac ttagaagcga tagaagcgat gatttcagcg tagtgaactc tagcaactct    4140
tgaaacagca gcaaccattg ggatggtagc ttgaccacca caggtaacca tgttaacgtt    4200
taattggtca acgttagctt ccaagttaac aactggaaca cagtatggac cgatagcagc    4260
tggggtcaag tcgatcaatc tgatgtctgg cttagcttct ctcaaagcag cgtcgttctt    4320
aacgtgagca ccagcagagg tagcgtcgaa acgatgtcg atgtcagcga attctggcat    4380
gttcatcaaa ccgataacac cttcgtgggt ggtagcaaca cccattcttc tagctctagc    4440
caaaccgtca gattgtgggt cgataccaac cataacagcc atttccaagt gttgaccgtg    4500
tcttaggatc ttgatcatca agtcagtacc gatgttacca gaaccgatga tagcaacctt    4560
tctcttagac atctgcagtc tagatatatt tgttgtaaaa agtagataat tacttccttg    4620
atgatctgta aaaagagaa aagaaagca tctaagaact tgaaaaacta cgaattagaa    4680
aagaccaaat atgtatttct tgcattgacc aatttatgca agtttatata tatgtaaatg    4740
taagtttcac gaggttctac taaactaaac cacccccttg gttagaagaa aagagtgtgt    4800
gagaacaggc tgttgttgtc acacgattcg gacaattctg tttgaaagag agagagtaac    4860
agtacgatcg aacgaacttt gctctggaga tcacagtggg catcatagca tgtggtacta    4920
aaccctttcc cgccattcca gaaccttcga ttgcttgtta caaaacctgt gagccgtcgc    4980
taggaccttg ttgtgtgacg aaattggaag ctgcaatcaa taggaagaca ggaagtcgag    5040
cgtgtctggg ttttttcagt tttgttcttt ttgcaaacaa atcacgagcg acggtaattt    5100
ctttctcgat aagaggccac gtgctttatg agggtaacat caattcaaga aggagggaaa    5160
cacttccttt ttctggccct gataatagta tgagggtgaa gccaaaataa aggattcgcg    5220
```

```
cccaaatcgg catctttaaa tgcaggtatg cgatagttcc tcactctttc cttactcacg    5280
agtaattctt gcaaatgcct attatgcaga tgttataata tctgtgcgtc ttgagttgaa    5340
gagctcgaga ctagtggatc ccccgggctg caggaattcg atatcaagct tatcgatacc    5400
gtcgacctcg agggggggcc cggtacccag cttttgttcc ctttagtgag ggttaattcc    5460
gagcttggcg taatcatggt catagctgtt tcctgtgtga aattgttatc cgctcacaat    5520
tccacacaac ataggagccg gaagcataaa gtgtaaagcc tggggtgcct aatgagtgag    5580
gtaactcaca ttaattgcgt tgcgctcact gcccgctttc cagtcgggaa acctgtcgtg    5640
ccagctgcat taatgaatcg gccaacgcgc ggggagaggc ggtttgcgta ttgggcgctc    5700
ttccgcttcc tcgctcactg actcgctgcg ctcggtcgtt cggctgcggc gagcggtatc    5760
agctcactca aaggcggtaa tacggttatc cacagaatca ggggataacg caggaaagaa    5820
catgtgagca aaaggccagc aaaaggccag gaaccgtaaa aaggccgcgt tgctggcgtt    5880
tttccatagg ctcggccccc ctgacgagca tcacaaaaat cgacgctcaa gtcagaggtg    5940
gcgaaacccg acaggactat aaagatacca ggcgttcccc cctggaagct ccctcgtgcg    6000
ctctcctgtt ccgaccctgc cgcttaccgg atacctgtcc gcctttctcc cttcgggaag    6060
cgtggcgctt tctcaatgct cacgctgtag gtatctcagt tcggtgtagg tcgttcgctc    6120
caagctgggc tgtgtgcacg aaccccccgt tcagcccgac cgctgcgcct tatccggtaa    6180
ctatcgtctt gagtccaacc cggtaagaca cgacttatcg ccactggcag cagccactgg    6240
taacaggatt agcagagcga ggtatgtagg cggtgctaca gagttcttga agtggtggcc    6300
taactacggc tacactagaa ggacagtatt tggtatctgc gctctgctga gccagttac    6360
cttcggaaaa agagttggta gctcttgatc cggcaaacaa accaccgctg gtagcggtgg    6420
tttttttgtt tgcaagcagc agattacgcg cagaaaaaaa ggatctcaag aagatccttt    6480
gatcttttct acggggtctg acgctcagtg gaacgaaaac tcacgttaag ggattttggt    6540
catgagatta tcaaaaagga tcttcaccta gatcctttta aattaaaaat gaagttttaa    6600
atcaatctaa agtatatatg agtaaacttg gtctgacagt taccaatgct taatcagtga    6660
ggcacctatc tcagcgatct gtctatttcg ttcatccata gttgcctgac tgcccgtcgt    6720
gtagataact acgatacggg agggcttacc atctggcccc agtgctgcaa tgataccgcg    6780
agacccacgc tcaccggctc cagatttatc agcaataaac cagccagccg aagggccga    6840
gcgcagaagt ggtcctgcaa ctttatccgc ctccatccag tctattaatt gttgccggga    6900
agctagagta gtagttcgc cagttaatag tttgcgcaac gttgttgcca ttgctacagg    6960
catcgtggtg tcacgctcgt cgtttggtat ggcttcattc agctccggtt cccaacgatc    7020
aaggcgagtt acatgatccc ccatgttgtg aaaaaaagcg gttagctcct tcggtcctcc    7080
gatcgttgtc agaagtaagt tggccgcagt gttatcactc atggttatgg cagcactgca    7140
taattctctt actgtcatgc catccgtaag atgcttttct gtgactggtg agtactcaac    7200
caagtcattc tgagaatagt gtatgcggcg accgagttgc tcttgcccgg cgtcaatacg    7260
ggataatacc gcgccacata gcagaacttt aaaagtgctc atcattggaa aacgttcttc    7320
ggggcgaaaa ctctcaagga tcttaccgct gttgagatcc agttcgatgt aacccactcg    7380
tgcacccaac tgatcttcag catctttta tttcaccagc gtttctgggt gagcaaaaac    7440
aggaaggcaa aatgccgcaa aaagggaat aagggcgaca cggaaatgtt gaatactcat    7500
actcttcctt tttcaatatt attgaagcat ttatcagggt tattgtctca tgagcggata    7560
catatttgaa tgtatttaga aaataaaca aatagggg t ccgcgcacat ttccccgaaa    7620
```

```
agtgccacct gacgtcttat tatcatgaca ttaacctata aaaataggcg tatcacgagg    7680 cccttt cgtc                                                          7690

<210> SEQ ID NO 30
<211> LENGTH: 9416
<212> TYPE: DNA
<213> ORGANISM: Artificial
<220> FEATURE:
<223> OTHER INFORMATION: pRN595

<400> SEQUENCE: 30
gacgaaaggg cctcgtgata cgcctatttt tataggttaa tgtcatgata ataagacgtc      60
aggtggcact tttcggggaa atgtgcgcgg aaccccta tt tgtttatttt tctaaataca    120
ttcaaatatg tatccgctca tgagacaata accctgataa atgcttcaat aatattgaaa    180
aaggaagagt atgagtattc aacatttccg tgtcgccctt attccctttt ttgcggcatt    240
ttgccttcct gttttt gctc acccagaaac gctggtgaaa gtaaaagatg ctgaagatca    300
gttgggtgca cgagtgggtt acatcgaact ggatctcaac agcggtaaga tccttgagag    360
ttttcgcccc gaagaacgtt ttccaatgat gagcactttt aaagttctgc tatgtggcgc    420
ggtattatcc cgtattgacg ccgggcaaga gcaactcggt cgccgcatac actattctca    480
gaatgacttg gttgagtact caccagtcac agaaaagcat cttacggatg gcatgacagt    540
aagagaatta tgcagtgctg ccataaccat gagtgataac actgcggcca acttacttct    600
gacaacgatc ggaggaccga aggagctaac cgcttttttt cacaacatgg ggatcatgt     660 aactcgcctt gatcgttggg aaccggagct gaatgaagcc ataccaaacg acgagcgtga    720
caccacgatg cctgtagcaa tggcaacaac gttgcgcaaa ctattaactg gcgaactact    780
tactctagct tcccggcaac aattaataga ctggatggag gcggataaag ttgcaggacc    840
acttctgcgc tcggcccttc cggctggctg gtttattgct gataaatctg gagccggtga    900
gcgtgggtct cgcggtatca ttgcagcact ggggccagat ggtaagccct cccgtatcgt    960
agttatctac acgacgggca gtcaggcaac tatggatgaa cgaaatagac agatcgctga   1020
gataggtgcc tcactgatta agcattggta actgtcagac caagtttact catatatact   1080
ttagattgat ttaaaacttc atttttaatt taaaaggatc taggtgaaga tcctttttga   1140
taatctcatg accaaaatcc cttaacgtga gttttcgttc cactgagcgt cagacccc gt   1200 agaaaagatc aaaggatctt cttgagatcc ttttttt ctg cgcgtaatct gctgcttgca   1260
aacaaaaaaa ccaccgctac cagcggtggt ttgtttgccg gatcaagagc taccaactct   1320
ttttccgaag gtaactggct tcagcagagc gcagatacca aatactgtcc ttctagtgta   1380
gccgtagtta ggccaccact tcaagaactc tgtagcaccg cctacatacc tcgctctgct   1440
aatcctgtta ccagtggctg ctgccagtgg cgataagtcg tgtcttaccg ggttggactc   1500
aagacgatag ttaccggata aggcgcagcg gtcgggctga acggggggtt cgtgcacaca   1560
gcccagcttg gagcgaacga cctacaccga actgagatac ctacagcgtg agcattgaga   1620
aagcgccacg cttcccgaag ggagaaaggc ggacaggtat ccggtaagcg cagggtcgg    1680 aacaggagag cgcacgaggg agcttccagg ggggaacgcc tggtatcttt atagtcctgt   1740
cgggtttcgc cacctctgac ttgagcgtcg atttttgtga tgctcgtcag gggggccgag   1800
cctatggaaa aacgccagca acgcggcctt tttacggttc ctggccttt t gctggcctt t   1860 tgctcacatg ttctttcctg cgttatcccc tgattctgtg gataaccgta ttaccgcctt   1920
```

```
tgagtgagct gataccgctc gccgcagccg aacgaccgag cgcagcgagt cagtgagcga    1980
ggaagcggaa gagcgcccaa tacgcaaacc gcctctcccc gcgcgttggc cgattcatta    2040
atgcagctgg cacgacaggt ttcccgactg gaaagcgggc agtgagcgca acgcaattaa    2100
tgtgagttac ctcactcatt aggcacccca ggctttacac tttatgcttc cggctcctat    2160
gttgtgtgga attgtgagcg gataacaatt tcacacagga aacagctatg accatgatta    2220
cgccaagctc ggaattaacc ctcactaaag ggaacaaaag ctgggtaccg gccccccct     2280 cgaggtcgac ggtatcgata agcttgatat cgaattcctg cagcccgggg gatccactag    2340
tctcgagctc ttcaactcaa gacgcacaga tattataaca tctgcataat aggcatttgc    2400
aagaattact cgtgagtaag gaaagagtga ggaactatcg catacctgca tttaaagatg    2460
ccgatttggg cgcgaatcct ttattttggc ttcaccctca tactattatc agggccagaa    2520
aaaggaagtg tttccctcct tcttgaattg atgttaccct cataaagcac gtggcctctt    2580
atcgagaaag aaattaccgt cgctcgtgat ttgtttgcaa aaagaacaaa actgaaaaaa    2640
cccagacacg ctcgacttcc tgtcttccta ttgattgcag cttccaattt cgtcacacaa    2700
caaggtccta gcgacggctc acaggttttg taacaagcaa tcgaaggttc tggaatggcg    2760
ggaaagggtt tagtaccaca tgctatgatg cccactgtga tctccagagc aaagttcgtt    2820
cgatcgtact gttactctct ctcttttcaaa cagaattgtc cgaatcgtgt gacaacaaca    2880
gcctgttctc acacactctt ttcttctaac caaggggtg gtttagttta gtagaacctc     2940
gtgaaactta catttacata tatataaact tgcataaatt ggtcaatgca agaaatacat    3000
atttggtctt ttctaattcg tagttttca agttcttaga tgctttcttt ttctcttttt     3060
tacagatcat caaggaagta attatctact ttttacaaca aatatatcta gaaaatggct    3120
gttaccaacg ttgctgaatt gaacgctttg gttgaaaggg ttaagaaggc tcaaagagaa    3180
tacgcttctt tcacccaaga acaagttgac aagatcttca gagctgctgc tttggctgct    3240
gctgacgcta gaatcccatt ggctaagatg gctgttgctg aatctggtat gggtatcgtt    3300
gaagacaagg ttatcaagaa ccacttcgct tctgaataca tctacaacgc ttacaaggac    3360
gaaaagacct gtggtgtttt gtcagaagac gacaccttcg gtaccatcac catcgctgaa    3420
ccaatcggta tcatctgtgg tatcgttcca accaccaacc caacctctac cgctatcttc    3480 aagtcttttga tctcttttgaa gaccagaaac gctatcatct tctctccaca cccaagagct    3540
aaagacgcta ccaacaaggc tgctgacatc gttttgcaag ctgctatcgc tgctggtgct    3600
ccaaaggact tgatcggttg gatcgaccaa ccatctgttg aattgtctaa cgctttgatg    3660
caccacccag acatcaactt gatcttggct accggtggtc caggtatggt taaggctgct    3720
tactcttctg gtaagccagc tatcggtgtt ggtgctggta acaccccagt tgttatcgac    3780
gaaaccgctg acatcaagag agctgttgct tctgttttga tgtctaagac cttcgacaac    3840
ggtgttatct gtgcttctga acaatctgtt gttgttgttg actctgttta cgacgctgtt    3900
agagaaagat tcgctaccca cggtggttac ttgttgcaag gtaaggaatt gaaggctgtt    3960
caagacgtta tcttgaagaa cggtgctttg aacgctgcta tcgttggtca accagcttac    4020
aagatcgcta attagctgg tttctctgtt ccagaaaaca ccaagatctt gatcggtgaa    4080
gttaccgttg ttgacgaatc tgaaccattc gctcacgaaa agttgtctcc aaccttggct    4140
atgtacagag ctaaggactt cgaagacgct gttgaaaaag ctgaaaagtt ggttgctatg    4200
ggtggtattg tcacacctc ttgtttgtac accgaccaag caaccaacc agctagagtt      4260 tcttacttcg gtcaaaagat gaagaccgct agaatcttga tcaacacccc agcttctcaa    4320
```

```
ggtggtatcg gtgacttgta caacttcaag ttggctccat ctttgacctt gggttgtggt    4380
tcttggggtg gtaactctat ctctgaaaac gttggtccaa agcacttgat caacaagaag    4440
accgttgcta agagagctga aaacatgttg tggcacaagt tgccaaaatc tatctacttc    4500
agaagaggtt ctttgccaat cgctttggac gaagttatca ccgacggtca aagagagct    4560 ttgatcgtta ccgacagatt cttgttcaac aacggttacg ctgaccaaat cacctctgtt    4620
ttgaaggctg ctggtgttga aaccgaagtt ttcttcgaag ttgaagctga cccaaccttg    4680
tctatcgtta gaaagggtgc tgaattggct aactctttca agccagacgt tatcatcgct    4740
ttgggtggtg gttctccaat ggacgctgct aagatcatgt gggttatgta cgaacaccca    4800
gaaacccact tcgaagaatt ggctttgaga ttcatggaca tcagaaagag aatctacaag    4860
ttcccaaaga tgggtgttaa ggctaagatg atcgctgtta ccaccacctc tggtaccggt    4920
tctgaagtta ccccattcgc tgttgttacc gacgacgcta ccggtcaaaa gtacccattg    4980
gctgactacg ctttgacccc agacatggct atcgttgacg ctaacttggt tatggacatg    5040
ccaaagtctt tgtgtgcttt cggtggtttg gacgctgtta cccacgctat ggaagcttac    5100
gtttctgttt tggcttctga attctctgac ggtcaagctt tgcaagcttt gaagttgttg    5160
aaggaatact tgccagcttc ttaccacgaa ggttctaaga acccagttgc tagagaaaga    5220
gttcactctg ctgctaccat cgctggtatc gctttcgcta acgctttctt gggtgtttgt    5280
cactctatgg ctcacaagtt gggttctcaa ttccacatcc cacacggtt gctaacgct    5340 ttgttgatct gtaacgttat cagatacaac gctaacgaca cccaaccaa gcaaaccgct    5400 ttctctcaat acgacagacc acaagctaga agaagatacg ctgaaatcgc tgaccacttg    5460
ggtttgtctg ctccaggtga cagaaccgct gcaaagatcg aaaagttgtt ggcttggttg    5520
gaaaccttga aggctgaatt gggtatccca aagtctatca gagaagctgg tgttcaagaa    5580
gctgacttct tggctaacgt tgacaagttg tctgaagacg ctttcgacga ccaatgtacc    5640
ggtgctaacc caagatacc attgatctct gaattgaagc aaatcttgtt ggacacctac    5700
tacggtagag actacgttga aggtgaaacc gctgctaaga aggaagctgc tccagctaag    5760
gctgaaaaga aggctaagaa gtctgcttag cttaagcgcg cgaatttctt atgatttatg    5820
atttttatta ttaaataagt tataaaaaaa ataagtgtat acaaatttta aagtgactct    5880
taggttttaa aacgaaaatt cttattcttg agtaactctt tcctgtaggt caggttgctt    5940
tctcaggtat agcatgaggt cgctcttatt gaccacacct ctaccggcat gccgagcaaa    6000
tgcctgcaaa tcgctcccca tttcacccaa ttgtagatat gctaactcca gcaatgagtt    6060
gatgaatctc ggtgtgtatt ttatgtcctc agaggacaac acctgttgta atcgttcttc    6120
cacacgtacg aagcttaaaa gggcgaattc tgcagatatc catcacactg gcggccgcat    6180
gctagctccg gattatcgat gataagctgt caaagatgag aattaattcc acggactata    6240
gactatacta gatactccgt ctactgtacg atacacttcc gctcaggtcc ttgtcctta    6300 acgaggcctt accactcttt tgttactcta ttgatccagc tcagcaaagg cagtgtgatc    6360
taagattcta tcttcgcgat gtagtaaaac tagctagacc gagaaagaga ctagaaatgc    6420
aaaaggcact tctacaatgg ctgccatcat tattatccga tgtgacgctg cagcttctca    6480
atgatattcg aatacgcttt gaggagatac agcctaatat ccgacaaact gttttacaga    6540
tttacgatcg tacttgttac ccatcattga attttgaaca tccgacctg ggagttttcc    6600 ctgaaacaga tagtatattt gaacctgtat aataatatat agtctagcgc tttacggaag    6660
```

-continued

```
acaatgtatg tatttcggtt cctggagaaa ctattgcatc tattgcatag gtaatcttgc    6720
acgtcgcatc cccggttcat tttctgcgtt tccatcttgc acttcaatag catatctttg    6780
ttaacgaagc atctgtgctt cattttgtag aacaaaaatg caacgcgaga gcgctaattt    6840
ttcaaacaaa gaatctgagc tgcattttta cagaacagaa atgcaacgcg aaagcgctat    6900
tttaccaacg aagaatctgt gcttcatttt tgtaaaacaa aaatgcaacg cgacgagagc    6960
gctaattttt caaacaaaga atctgagctg cattttttaca gaacgaaat gcaacgcgag    7020
agcgctattt taccaacaaa gaatctatac ttcttttttg ttctacaaaa atgcatcccg    7080
agagcgctat ttttctaaca aagcatctta gattactttt tttctccttt gtgcgctcta    7140
taatgcagtc tcttgataac ttttttgcact gtaggtccgt taaggttaga agaaggctac    7200
tttggtgtct attttctctt ccataaaaaa agcctgactc cacttcccgc gtttactgat    7260
tactagcgaa gctgcgggtg cattttttca agataaaggc atccccgatt atattctata    7320
ccgatgtgga ttgcgcatac tttgtgaaca gaaagtgata gcgttgatga ttcttcattg    7380
gtcagaaaat tatgaacggt ttcttctatt ttgtctctat atactacgta taggaaatgt    7440
ttacattttc gtattgtttt cgattcactc tatgaatagt tcttactaca attttttgt    7500
ctaaagagta atactagaga taaacataaa aaatgtagag gtcgagttta gatgcaagtt    7560
caaggagcga aaggtggatg ggtaggttat atagggatat agcacagaga tatatagcaa    7620
agagatactt ttgagcaatg tttgtggaag cggtattcgc aatgccggct ttccccgtca    7680
agctctaaat cgggggctcc ctttaggggtt ccgatttagt gctttacggc acctcgaccc    7740
caaaaaactt gattagggtg atggttcacg tagtgggcca tcgccctgat agacggtttt    7800
tcgcccttttg acgttggagt ccacgttctt taatagtgga ctcttgttcc aaactggaac    7860
aacactcaac cctatctcgg tctattcttt tgatttataa gggattttgc cgatttcggc    7920
ctattggtta aaaatgagc tgatttaaca aaaatttaac gcgaatttta acaaaatatt    7980
aacgtttaca atttcctgat gcggtatttt ctccttacgc atctgtgcgg tatttcacac    8040
cgcatatgat ccgtcgagtt caagagaaaa aaaagaaaa agcaaaaaga aaaaggaaa    8100
gcgcgcctcg ttcagaatga cacgtataga atgatgcatt accttgtcat cttcagtatc    8160
atactgttcg tatacatact tactgacatt cataggtata catatataca catgtatata    8220
tatcgtatgc tgcagcttta aataatcggt gtcactacat aagaacaccct ttggtggagg    8280
gaacatcgtt ggtaccattg ggcgaggtgg cttctcttat ggcaaccgca agagccttga    8340
acgcactctc actacggtga tgatcattct tgcctcgcag acaatcaacg tggagggtaa    8400
ttctgctagc ctctgcaaag ctttcaagaa aatgcgggat catctcgcaa gagagatctc    8460
ctactttctc cctttgcaaa ccaagttcga caactgcgta cggcctgttc gaaagatcta    8520
ccaccgctct ggaaagtgcc tcatccaaag cgcaaatcc tgatccaaac cttttactc    8580
cacgcgccag tagggcctct ttaaaagctt gaccgagagc aatcccgcag tcttcagtgg    8640
tgtgatggtc gtctatgtgt aagtcaccaa tgcactcaac gattagcgac cagccggaat    8700
gcttggccag agcatgtatc atatggtcca gaaaccctat acctgtgtgg acgttaatca    8760
cttgcgattg tgtggcctgt tctgctactg cttctgcctc ttttctctggg aagatcgagt    8820
gctctatcgc tagggaccac ccctttaaag agatcgcaat ctgaatcttg gtttcatttg    8880
taatacgctt tactagggct ttctgctctg tcatctttgc cttcgtttat cttgcctgct    8940
catttttttag tatattcttc gaagaaatca cattactttta tataatgtat aattcattat    9000
gtgataatgc caatcgctaa gaaaaaaaaa gagtcatccg ctaggtggaa aaaaaaaaat    9060
```

| | | |
|---|---|---|
| gaaaatcatt accgaggcat aaaaaaatat agagtgtact agaggaggcc aagagtaata | 9120 |
| gaaaaagaaa attgcgggaa aggactgtgt tatgacttcc ctgactaatg ccgtgttcaa | 9180 |
| acgatacctg gcagtgactc ctagcgctca ccaagctctt aaaacggaat tatggtgcac | 9240 |
| tctcagtaca atctgctctg atgccgcata gttaagccag ccccgacacc cgccaacacc | 9300 |
| cgctgacgcg ccctgacggg cttgtctgct cccggcatcc gcttacagac aagctgtgac | 9360 |
| cgtctccggg agctgcatgt gtcagaggtt ttcaccgtca tcaccgaaac gcgcga | 9416 |

<210> SEQ ID NO 31
<211> LENGTH: 9352
<212> TYPE: DNA
<213> ORGANISM: Artificial
<220> FEATURE:
<223> OTHER INFORMATION: pRN596

<400> SEQUENCE: 31

| | | |
|---|---|---|
| gacgaaaggg cctcgtgata cgcctatttt tataggttaa tgtcatgata ataagacgtc | 60 |
| aggtggcact tttcggggaa atgtgcgcgg aacccctatt tgtttatttt tctaaataca | 120 |
| ttcaaatatg tatccgctca tgagacaata accctgataa atgcttcaat aatattgaaa | 180 |
| aaggaagagt atgagtattc aacatttccg tgtcgccctt attcccttt ttgcggcatt | 240 |
| ttgccttcct gtttttgctc acccagaaac gctggtgaaa gtaaaagatg ctgaagatca | 300 |
| gttgggtgca cgagtgggtt acatcgaact ggatctcaac agcggtaaga tccttgagag | 360 |
| ttttcgcccc gaagaacgtt ttccaatgat gagcactttt aaagttctgc tatgtggcgc | 420 |
| ggtattatcc cgtattgacg ccgggcaaga gcaactcggt cgccgcatac actattctca | 480 |
| gaatgacttg gttgagtact caccagtcac agaaaagcat cttacggatg gcatgacagt | 540 |
| aagagaatta tgcagtgctg ccataaccat gagtgataac actgcggcca acttacttct | 600 |
| gacaacgatc ggaggaccga aggagctaac cgcttttttt cacaacatgg ggatcatgt | 660 |
| aactcgcctt gatcgttggg aaccggagct gaatgaagcc ataccaaacg acgagcgtga | 720 |
| caccacgatg cctgtagcaa tggcaacaac gttgcgcaaa ctattaactg gcgaactact | 780 |
| tactctagct tcccggcaac aattaataga ctggatggag gcggataaag ttgcaggacc | 840 |
| acttctgcgc tcggcccttc cggctggctg gtttattgct gataaatctg gagccggtga | 900 |
| gcgtgggtct cgcggtatca ttgcagcact ggggccagat ggtaagccct cccgtatcgt | 960 |
| agttatctac acgacgggca gtcaggcaac tatggatgaa cgaaatagac agatcgctga | 1020 |
| gataggtgcc tcactgatta agcattggta actgtcagac caagtttact catatatact | 1080 |
| ttagattgat ttaaaacttc atttttaatt taaaaggatc taggtgaaga tcctttttga | 1140 |
| taatctcatg accaaaatcc cttaacgtga gttttcgttc cactgagcgt cagacccgt | 1200 |
| agaaaagatc aaaggatctt cttgagatcc ttttttctg cgcgtaatct gctgcttgca | 1260 |
| aacaaaaaaa ccaccgctac cagcggtggt ttgtttgccg gatcaagagc taccaactct | 1320 |
| ttttccgaag gtaactggct tcagcagagc gcagatacca atactgtcc ttctagtgta | 1380 |
| gccgtagtta ggccaccact tcaagaactc tgtagcaccg cctacatacc tcgctctgct | 1440 |
| aatcctgtta ccagtggctg ctgccagtgg cgataagtcg tgtcttaccg ggttggactc | 1500 |
| aagacgatag ttaccggata aggcgcagcg gtcgggctga acggggggtt cgtgcacaca | 1560 |
| gcccagcttg gagcgaacga cctacaccga actgagatac ctacagcgtg agcattgaga | 1620 |
| aagcgccacg cttcccgaag ggagaaaggc ggacaggtat ccggtaagcg gcagggtcgg | 1680 |

```
aacaggagag cgcacgaggg agcttccagg ggggaacgcc tggtatcttt atagtcctgt    1740
cgggtttcgc cacctctgac ttgagcgtcg attttttgtga tgctcgtcag ggggccgag    1800 cctatggaaa aacgccagca acgcggcctt tttacggttc ctggccttt gctggccttt     1860 tgctcacatg ttctttcctg cgttatcccc tgattctgtg ataaccgta ttaccgcctt     1920 tgagtgagct gataccgctc gccgcagccg aacgaccgag cgcagcgagt cagtgagcga    1980
ggaagcggaa gagcgcccaa tacgcaaacc gcctctcccc gcgcgttggc cgattcatta    2040
atgcagctgg cacgacaggt ttcccgactg gaaagcgggc agtgagcgca acgcaattaa    2100
tgtgagttac ctcactcatt aggcacccca ggctttacac tttatgcttc cggctcctat    2160
gttgtgtgga attgtgagcg gataacaatt tcacacagga aacagctatg accatgatta    2220
cgccaagctc ggaattaacc ctcactaaag ggaacaaaag ctgggtaccg gccccccct    2280 cgaggtcgac ggtatcgata agcttgatat cgaattcctg cagcccgggg gatccactag    2340
tctcgagctc ttcaactcaa gacgcacaga tattataaca tctgcataat aggcatttgc    2400
aagaattact cgtgagtaag gaaagagtga ggaactatcg catacctgca tttaaagatg    2460
ccgatttggg cgcgaatcct ttattttggc ttcaccctca tactattatc agggccagaa    2520
aaaggaagtg tttccctcct tcttgaattg atgttaccct cataaagcac gtggcctctt    2580
atcgagaaag aaattaccgt cgctcgtgat ttgtttgcaa aaagaacaaa actgaaaaaa    2640
cccagacacg ctcgacttcc tgtcttccta ttgattgcag cttccaattt cgtcacacaa    2700
caaggtccta gcgacggctc acaggttttg taacaagcaa tcgaaggttc tggaatggcg    2760
ggaaagggtt tagtaccaca tgctatgatg cccactgtga tctccagagc aaagttcgtt    2820
cgatcgtact gttactctct ctctttcaaa cagaattgtc cgaatcgtgt gacaacaaca    2880
gcctgttctc acacactctt ttcttctaac caagggggtg gtttagttta gtagaacctc    2940
gtgaaactta catttacata tatataaact tgcataaatt ggtcaatgca agaaatacat    3000
atttggtctt ttctaattcg tagttttttca agttcttaga tgctttcttt ttctcttttt    3060
tacagatcat caaggaagta attatctact ttttacaaca aatatatcta gaaaatgtct    3120
acccaacaaa ccatgaccgt tgacgaacac atcaaccaat tagttagaaa ggctcaagtt    3180
gctttgaagg aatacttgaa gccagaatac acccaagaaa agatcgacta catcgttaag    3240
aaggcttctg ttgctgcttt ggaccaacac tgtgctttgg ctgctgctgc tgttgaagaa    3300
accggtagag gtatcttcga agacaaggct accaagaaca tcttcgcttg tgaacacgtt    3360
acccacgaaa tgagacacgc taagaccgtt ggtatcatca acgttgaccc attgtacggt    3420
atcaccgaaa tcgctgaacc agttggtgtt gtttgtggtg ttacccccagt taccaaccca    3480 acctctaccg ctatcttcaa gtctttgatc tctatcaaga ccagaaaccc aatcgttttc    3540
tctttccacc catctgcttt gaagtgttct attatggctg ctaaaatcgt tagagacgct    3600
gctatcgctg ctggtgctcc agaaaaactgt atccaatgga tcgaattcgg tggtatcgaa    3660
gcttctaaca agttgatgaa ccacccaggt gttgctacta tcttggctac cggtggtaac    3720
gctatggtta aggctgcata ctcttctggt aagccagctt gggtgttgg tgctggtaac    3780 gttccaacct acatcgaaaa gacctgtaac atcaagcaag ctgctaacga cgttgttatg    3840
tctaagtctt tcgacaacgg tatgatctgt gcttctgaac aagctgctat catcgacaag    3900
gaaatctacg accaagttgt tgaagaaatg aagaccttgg gtgcttactt catcaacgaa    3960
gaagaaaagg ctaagttgga aaagttcatg ttcggtgtta acgcttactc tgctgacgtt    4020
aacaacgcta gattgaaccc aaagtgtcca ggtatgtctc cacaatggtt cgctgaacaa    4080
```

```
gttggtatca aggtaccaga agactgtaac atcatctgtg ctgtttgtaa ggaagttggt    4140
ccaaacgaac cattgaccag agaaaagttg tctccagttt tggctatctt gaaagctgaa    4200
aacacccaag acggtatcga caaggctgaa gctatggttg aatttaacgg tagaggtcac    4260
tctgctgcta tccactctaa cgacaaggct gttgttgaaa agtacgcttt gaccatgaag    4320
gcttgtagaa tcttgcacaa caccccatct tctcaaggtg gtatcggttc tatctacaac    4380
tacatctggc catcttttcac cttgggttgt ggttcttacg gtggtaactc tgtttctgct    4440
aacgttacct accacaactt gttgaacatc aagagattgg ctgacagaag aaacaacttg    4500
caatggttca gagttccacc aaagatcttc ttcgaaccac actctatcag atacttggct    4560
gaattgaagg aattgtctaa gatcttcatc gtttctgaca gaatgatgta caagttgggt    4620
tacgttgaca gagttatgga cgttttgaag agaagatcta acgaagttga atcgaaatc     4680
ttcatcgacg ttgaaccaga cccatctatc caaaccgttc aaaagggttt ggctgttatg    4740
aacaccttcg gtccagacaa catcatcgct atcggtggtg ttctgctat ggacgctgct     4800
aagatcatgt ggttgttgta cgaacaccca gaagctgact tcttcgctat gaagcaaaag    4860
ttcatcgact gagaaagag agctttcaag ttcccaacca tgggtaagaa ggctagattg     4920
atctgtatcc caaccacctc tggtaccggt tctgaagtta ccccattcgc tgttatctct    4980
gaccacgaaa ccggtaagaa gtacccattg gctgactact ctttgacccc atctgttgct    5040
atcgttgacc caatgttcac catgtctttg ccaaagagag ctatcgctga caccggtttg    5100
gacgttttgg ttcacgctac cgaagcttac gtttctgtta tggctaacga atacaccgac    5160
ggtttggcta gagaagctgt taagttggtt tttgaaaact tgttgaagtc ttacaacggt    5220
gacttggaag ctagagaaaa gatgcacaac gctgctacca tcgctggtat ggctttcgct    5280
tctgctttct tgggtatgga ccactctatg gctcacaagg ttggtgctgc tttccacttg    5340
ccacacggta gatgtgttgc tgttttgttg ccacacgtta tcagatacaa cggtcaaaag    5400
ccaagaaagt tggctatgtg gccaaagtac aacttctaca aggctgacca aagatacatg    5460
gaattggctc aaatggttgg tttgaagtgt aacaccccag ctgaaggtgt tgaagctttc    5520
gctaaggctt gtgaagaatt gatgaaggct accgaaacca tcaccggttt caagaaggct    5580
aacatcgacg aagctgcttg gatgtctaag gttccagaaa tggctttgtt ggctttcgaa    5640
gaccaatgtt ctccagctaa cccaagagtt ccaatggtta aggacatgga aaagatcttg    5700
aaggctgctt actacccaat cgcttagctt aagcgcgcga atttcttatg atttatgatt    5760
tttattatta aataagttat aaaaaaaata agtgtataca aatttaaaag tgactcttag    5820
gttttaaaac gaaaattctt attcttgagt aactctttcc tgtaggtcag gttgctttct    5880
caggtatagc atgaggtcgc tcttattgac cacacctcta ccggcatgcc gagcaaatgc    5940
ctgcaaatcg ctccccattt cacccaattg tagatatgct aactccagca atgagttgat    6000
gaatctcggt gtgtattta tgtcctcaga ggacaacacc tgttgtaatc gttcttccac     6060
acgtacgaag ctaaaagggc gaattctgca gatatccatc acactggcgg ccgcatgcta    6120
gctccggatt atcgatgata agctgtcaaa gatgagaatt aattccacgg actatagact    6180
atactagata ctccgtctac tgtacgatac acttccgctc aggtccttgt cctttaacga    6240
ggccttacca ctcttttgtt actctattga tccagctcag caaaggcagt gtgatctaag    6300
attctatctt cgcgatgtag taaaactagc tagaccgaga aagagactag aaatgcaaaa    6360
ggcacttcta caatggctgc catcattatt atccgatgtg acgctgcagc ttctcaatga    6420
```

```
tattcgaata cgctttgagg agatacagcc taatatccga caaactgttt tacagattta    6480
cgatcgtact tgttacccat cattgaattt tgaacatccg aacctgggag ttttccctga    6540
aacagatagt atatttgaac ctgtataata atatatagtc tagcgcttta cggaagacaa    6600
tgtatgtatt tcggttcctg agaaactat tgcatctatt gcataggtaa tcttgcacgt     6660
cgcatccccg gttcattttc tgcgttcca tcttgcactt caatagcata tctttgttaa     6720
cgaagcatct gtgcttcatt tgtagaaca aaaatgcaac gcgagagcgc taatttttca     6780
aacaaagaat ctgagctgca ttttacaga acagaaatgc aacgcgaaag cgctatttta     6840
ccaacgaaga atctgtgctt cattttgta aaacaaaaat gcaacgcgac gagagcgcta    6900
atttttcaaa caaagaatct gagctgcatt tttacagaac agaaatgcaa cgcgagagcg    6960 ctatttacc aacaaagaat ctatacttct tttgttct acaaaatgc atcccgagag        7020 cgctattttt ctaacaaagc atcttagatt acttttttc tcctttgtgc gctctataat     7080
gcagtctctt gataactttt tgcactgtag gtccgttaag gttagaagaa ggctactttg    7140
gtgtctattt tctcttccat aaaaaaagcc tgactccact tcccgcgttt actgattact    7200
agcgaagctg cgggtgcatt ttttcaagat aaaggcatcc ccgattatat tctataccga    7260
tgtggattgc gcatactttg tgaacagaaa gtgatagcgt tgatgattct tcattggtca    7320
gaaaattatg aacggtttct tctatttgt ctctatatac tacgtatagg aaatgtttac     7380
attttcgtat tgttttcgat tcactctatg aatagttctt actacaattt ttttgtctaa    7440
agagtaatac tagagataaa cataaaaaat gtagaggtcg agtttagatg caagttcaag    7500
gagcgaaagg tggatgggta ggttatatag ggatatagca cagagatata tagcaaagag    7560
atacttttga gcaatgtttg tggaagcggt attcgcaatg ccggctttcc ccgtcaagct    7620
ctaaatcggg ggctcccttt agggttccga tttagtgctt tacggcacct cgaccccaaa    7680
aaacttgatt agggtgatgg ttcacgtagt gggccatcgc cctgatagac ggtttttcgc    7740
cctttgacgt tggagtccac gttctttaat agtggactct tgttccaaac tggaacaaca    7800
ctcaacccta tctcggtcta ttctttgat ttataaggga ttttgccgat tcggcctat     7860 tggttaaaaa atgagctgat ttaacaaaaa tttaacgcga attttaacaa aatattaacg    7920
tttacaattt cctgatgcgg tattttctcc ttacgcatct gtgcggtatt tcacaccgca    7980
tatgatccgt cgagttcaag agaaaaaaa agaaaaagca aaagaaaaa aggaaagcgc     8040 gcctcgttca gaatgacacg tatagaatga tgcattacct tgtcatcttc agtatcatac    8100
tgttcgtata catacttact gacattcata ggtatacata tatacacatg tatatatatc    8160
gtatgctgca gctttaaata atcggtgtca ctacataaga acacctttgg tggagggaac    8220
atcgttggta ccattgggcg aggtggcttc tcttatggca accgcaagag ccttgaacgc    8280
actctcacta cggtgatgat cattcttgcc tcgcagacaa tcaacgtgga gggtaattct    8340
gctagcctct gcaaagcttt caagaaaatg cgggatcatc tcgcaagaga gatctcctac    8400 tttctcccctt tgcaaaccaa gttcgacaac tgcgtacggc tgttcgaaa gatctaccac    8460 cgctctggaa agtgcctcat ccaaaggcgc aaatcctgat ccaaaccttt ttactccacg    8520
cgccagtagg gcctctttaa aagcttgacc gagagcaatc ccgcagtctt cagtggtgtg    8580
atggtcgtct atgtgtaagt caccaatgca ctcaacgatt agcgaccagc cggaatgctt    8640
ggccagagca tgtatcatat ggtccagaaa ccctatacct gtgtggacgt taatcacttg    8700
cgattgtgtg gcctgttctg ctactgcttc tgcctctttt tctgggaaga tcgagtgctc    8760
tatcgctagg ggaccaccct ttaaagagat cgcaatctga atcttggttt catttgtaat    8820
```

```
acgctttact agggctttct gctctgtcat ctttgccttc gtttatcttg cctgctcatt    8880
ttttagtata ttcttcgaag aaatcacatt actttatata atgtataatt cattatgtga    8940
taatgccaat cgctaagaaa aaaaagagt catccgctag gtggaaaaaa aaaatgaaa      9000 atcattaccg aggcataaaa aaatatagag tgtactagag gaggccaaga gtaatagaaa    9060
aagaaaattg cgggaaagga ctgtgttatg acttccctga ctaatgccgt gttcaaacga    9120
tacctggcag tgactcctag cgctcaccaa gctcttaaaa cggaattatg gtgcactctc    9180
agtacaatct gctctgatgc cgcatagtta agccagcccc gacacccgcc aacacccgct    9240
gacgcgccct gacgggcttg tctgctcccg gcatccgctt acagacaagc tgtgaccgtc    9300
tccgggagct gcatgtgtca gaggttttca ccgtcatcac cgaaacgcgc ga            9352
```

```
<210> SEQ ID NO 32
<211> LENGTH: 29
<212> TYPE: DNA
<213> ORGANISM: Artificial
<220> FEATURE:
<223> OTHER INFORMATION: Primer GPD2uf

<400> SEQUENCE: 32
ggtaccagat cttttgcggc gaggtgccg                                        29

<210> SEQ ID NO 33
<211> LENGTH: 42
<212> TYPE: DNA
<213> ORGANISM: Artificial
<220> FEATURE:
<223> OTHER INFORMATION: Primer GPD2ur

<400> SEQUENCE: 33
tctagactta aggaatgtgt atcttgttaa tcttctgaca gc                         42

<210> SEQ ID NO 34
<211> LENGTH: 28
<212> TYPE: DNA
<213> ORGANISM: Artificial
<220> FEATURE:
<223> OTHER INFORMATION: Primer GPD2df

<400> SEQUENCE: 34
ctcgagatag tctacaacaa cgtccgca                                         28

<210> SEQ ID NO 35
<211> LENGTH: 39
<212> TYPE: DNA
<213> ORGANISM: Artificial
<220> FEATURE:
<223> OTHER INFORMATION: Primer GPD2dr

<400> SEQUENCE: 35
ccatggagat ctgcagtgaa aaagctcgaa gaaacagct                             39

<210> SEQ ID NO 36
<211> LENGTH: 4397
<212> TYPE: DNA
<213> ORGANISM: Artificial
<220> FEATURE:
<223> OTHER INFORMATION: pRN594

<400> SEQUENCE: 36
gacgacggcg acctggcggg cttcgtggtc gtctcgtact ccggctggaa ccgccggctg     60
```

```
accgtcgagg acatcgaggt cgccccggag caccgggggc acggggtcgg gcgcgcgttg    120
atggggctcg cgacggagtt cgcccgcgag cggggcgccg ggcacctctg gctggaggtc    180
accaacgtca acgcaccggc gatccacgcg taccggcgga tggggttcac cctctgcggc    240
ctggacaccg ccctgtacga cggcaccgcc tcggacggcg agcaggcgct ctacatgagc    300
atgccctgcc cctagtactg acaataaaaa gattcttgtt ttcaagaact tgtcatttgt    360
atagttttt  tatattgtag ttgttctatt ttaatcaaat gttagcgtga tttatatttt    420
ttttcgcctc gacatcatct gcccagatgc gaagttaagt gcgcagaaag taatatcatg    480
cgtcaatcgt atgtgaatgc tggtcgctat actgctgtcg attcgatact aacgccgcca    540
tccagtgtcg acggatccta ggtgtacagg gcccaaaagg gcgaattctg cagatatcca    600
tcacactggc ggccgctcga gatagtctac aacaacgtcc gcatggaaga cctaccggag    660
atgattgaag agctagacat cgatgacgaa tagacactct ccccccccct cccctctga    720
tctttcctgt tgcctctttt tccccaacc  aatttatcat tatacacaag ttctacaact    780
actactagta acattactac agttattata attttctatt ctcttttct  ttaagaatct    840
atcattaacg ttaatttcta tatatacata actaccatta tacacgctat tatcgtttac    900
atatcacatc accgttaatg aaagatacga caccctgtac actaacacaa ttaaataatc    960
gccataacct tttctgttat ctatagccct taaagctgtt tcttcgagct ttttcactgc   1020
agatctccat ggcgatgcct gcttgccgaa tatcatggtg gaaaatggcc gcttttctgg   1080
attcatcgac tgtggccggc tgggtgtggc ggaccgctat caggacatag cgttggctac   1140
ccgtgatatt gctgaagagc ttggcggcga atgggctgac cgcttcctcg tgctttacgg   1200
tatcgccgct cccgattcgc agcgcatcgc cttctatcgc cttcttgacg agttcttctg   1260
aattgaaaaa ggaagagtat gagtattcaa catttccgtg tcgcccttat tccctttttt   1320
gcggcatttt gccttcctgt ttttgctcac ccagaaacgc tggtgaaagt aaaagatgct   1380
gaagatcagt tgggtgcacg agtgggttac atcgaactgg atctcaacag cggtaagatc   1440
cttgagagtt ttcgccccga gaacgttttt ccaatgatga gcacttttaa agttctgcta   1500
tgtggcgcgg tattatcccg tattgacgcc gggcaagagc aactcggtcg ccgcatacac   1560
tattctcaga atgacttggt tgagtactca ccagtcacag aaaagcatct tacggatggc   1620
atgacagtaa gagaattatg cagtgctgcc ataaccatga gtgataacac tgcggccaac   1680
ttacttctga caacgatcgg aggaccgaag gagctaaccg cttttttgca caacatgggg   1740
gatcatgtaa ctcgccttga tcgttgggaa ccggagctga atgaagccat accaaacgac   1800
gagcgtgaca ccacgatgcc tgtagcaatg gcaacaacgt tgcgcaaact attaactggc   1860
gaactactta ctctagcttc ccggcaacaa ttaatagact ggatggaggc ggataaagtt   1920
gcaggaccac ttctgcgctc ggcccttccg gctggctggt ttattgctga taaatctgga   1980
gccggtgagc gtgggtctcg cggtatcatt gcagcactgg ggccagatgg taagccctcc   2040
cgtatcgtag ttatctacac gacggggagt caggcaacta tggatgaacg aaatagacag   2100
atcgctgaga taggtgcctc actgattaag cattggtaac tgtcagacca agtttactca   2160
tatatacttt agattgattt aaaacttcat ttttaattta aaaggatcta ggtgaagatc   2220
cttttttgata atctcatgac caaaatccct taacgtgagt tttcgttcca ctgagcgtca   2280
gaccccgtag aaaagatcaa aggatcttct tgagatcctt ttttttctgcg cgtaatctgc   2340
tgcttgcaaa caaaaaaacc accgctacca gcggtggttt gtttgccgga tcaagagcta   2400
ccaactcttt ttccgaaggt aactggcttc agcagagcgc agataccaaa tactgttctt   2460
```

```
ctagtgtagc cgtagttagg ccaccacttc aagaactctg tagcaccgcc tacatacctc    2520
gctctgctaa tcctgttacc agtggctgct gccagtggcg ataagtcgtg tcttaccggg    2580
ttggactcaa gacgatagtt accggataag gcgcagcggt cgggctgaac ggggggttcg    2640
tgcacacagc ccagcttgga gcgaacgacc tacaccgaac tgagatacct acagcgtgag    2700
ctatgagaaa gcgccacgct tcccgaaggg agaaaggcgg acaggtatcc ggtaagcggc    2760
agggtcggaa caggagagcg cacgagggag cttccagggg gaaacgcctg gtatctttat    2820
agtcctgtcg ggtttcgcca cctctgactt gagcgtcgat ttttgtgatg ctcgtcaggg    2880
gggcggagcc tatggaaaaa cgccagcaac gcggcctttt tacggttcct ggccttttgc    2940
tggccttttg ctcacatgtt ctttcctgcg ttatcccctg attctgtgga taaccgtatt    3000
accgcctttg agtgagctga taccgctcgc cgcagccgaa cgaccgagcg cagcgagtca    3060
gtgagcgagg aagcggaaga gcgcccaata cgcaaaccgc ctctccccgc gcgttggccg    3120
attcattaat gcagctggca cgacaggttt cccgactgga aagcgggcag tgagcgcaac    3180
gcaattaatg tgagttagct cactcattag gcaccccagg ctttacactt tatgcttccg    3240
gctcgtatgt tgtgtggaat tgtgagcgga taacaatttc acacaggaaa cagctatgac    3300
catgattacg ccaagctatt taggtgacac tatagaatac tcaagctatg catcaagctt    3360
ggtaccagat cttttgcggc gaggtgccga tgggttgctg aggggaagag tgtttagctt    3420
acggacctat tgccattgtt attccgatta atctattgtt cagcagctct tctctaccct    3480
gtcattctag tatttttttt ttttttttttt ggttttactt tttttcttc ttgccttttt    3540 ttcttgttac ttttttttcta gttttttttc cttccactaa gcttttttcct tgatttatcc    3600 ttgggttctt ctttctactc ctttagattt tttttttata tattaatttt taagtttatg    3660
tattttggta gattcaattc tctttccctt tcctttttcct tcgctcccct tccttatcaa    3720
tgcttgctgt cagaagatta acaagataca cattccttaa ggcctcgtcc ccgccgggtc    3780
acccggccag cgacatggag gcccagaata ccctccttga cagtcttgac gtgcgcagct    3840
caggggcatg atgtgactgt cgcccgtaca tttagcccat acatccccat gtataatcat    3900
ttgcatccat acattttgat ggccgcacgg cgcgaagcaa aaattacggc tcctcgctgc    3960
agacctgcga gcaggggaaac gctcccctca cagacgcgtt gaattgtccc cacgccgcgc    4020
ccctgtagag aaatataaaa ggttaggatt tgccactgag gttcttcttt catatacttc    4080
cttttaaaat cttgctagga tacagttctc acatcacatc cgaacataaa caaccatgta    4140
aaatgaccac tcttgacgac acggcttacc ggtaccgcac cagtgtcccg ggggacgccg    4200
aggccatcga ggcactggat gggtccttca ccaccgacac cgtcttccgc gtcaccgcca    4260
ccggggacgc cttcaccctg cgggaggtgc cggtggaccc gccctgacc aaggtgttcc    4320 ccgacgacga atcggacgac gaatcggacg ccggggagga cggcgacccg gactcccgga    4380
cgttcgtcgc gtacggg                                                  4397
```

<210> SEQ ID NO 37
<211> LENGTH: 14200
<212> TYPE: DNA
<213> ORGANISM: Artificial
<220> FEATURE:
<223> OTHER INFORMATION: pRN957

<400> SEQUENCE: 37

```
gacgaaaggg cctcgtgata cgcctatttt tataggttaa tgtcatgata ataagacgtc      60
```

-continued

```
aggtggcact tttcggggaa atgtgcgcgg aaccccctatt tgtttatttt tctaaataca      120
ttcaaatatg tatccgctca tgagacaata accctgataa atgcttcaat aatattgaaa      180
aaggaagagt atgagtattc aacatttccg tgtcgccctt attccctttt ttgcggcatt      240
ttgccttcct gtttttgctc acccagaaac gctggtgaaa gtaaaagatg ctgaagatca      300
gttgggtgca cgagtgggtt acatcgaact ggatctcaac agcggtaaga tccttgagag      360
ttttcgcccc gaagaacgtt ttccaatgat gagcactttt aaagttctgc tatgtggcgc      420
ggtattatcc cgtattgacg ccgggcaaga gcaactcggt cgccgcatac actattctca      480
gaatgacttg gttgagtact caccagtcac agaaaagcat cttacggatg gcatgacagt      540
aagagaatta tgcagtgctg ccataaccat gagtgataac actgcggcca acttacttct      600
gacaacgatc ggaggaccga aggagctaac cgcttttttt cacaacatgg ggatcatgt       660 aactcgcctt gatcgttggg aaccggagct gaatgaagcc ataccaaacg acgagcgtga      720
caccacgatg cctgtagcaa tggcaacaac gttgcgcaaa ctattaactg gcgaactact      780
tactctagct tcccggcaac aattaataga ctggatggag gcggataaag ttgcaggacc      840
acttctgcgc tcggcccttc cggctggctg gtttattgct gataaatctg gagccggtga      900
gcgtgggtct cgcggtatca ttgcagcact ggggccagat ggtaagccct cccgtatcgt      960
agttatctac acgacgggca gtcaggcaac tatggatgaa cgaaatagac agatcgctga     1020
gataggtgcc tcactgatta agcattggta actgtcagac caagtttact catatatact     1080
ttagattgat ttaaaacttc attttaatt taaaaggatc taggtgaaga tccttttga      1140 taatctcatg accaaaatcc cttaacgtga gttttcgttc cactgagcgt cagacccgt      1200 agaaaagatc aaaggatctt cttgagatcc ttttttctg cgcgtaatct gctgcttgca     1260
aacaaaaaaa ccaccgctac cagcggtggt ttgtttgccg gatcaagagc taccaactct     1320
ttttccgaag gtaactggct tcagcagagc gcagatacca aatactgtcc ttctagtgta     1380
gccgtagtta ggccaccact tcaagaactc tgtagcaccg cctacatacc tcgctctgct     1440
aatcctgtta ccagtggctg ctgccagtgg cgataagtcg tgtcttaccg ggttggactc     1500
aagacgatag ttaccggata aggcgcagcg gtcgggctga acggggggtt cgtgcacaca     1560
gcccagcttg gagcgaacga cctacaccga actgagatac ctacagcgtg agcattgaga     1620
aagcgccacg cttcccgaag ggagaaaggc ggacaggtat ccggtaagcg cagggtcgg      1680 aacaggagag cgcacgaggg agcttccagg ggggaacgcc tggtatcttt atagtcctgt     1740
cgggtttcgc cacctctgac ttgagcgtcg attttgtga tgctcgtcag ggggccgag      1800 cctatggaaa aacgccagca acgcggcctt tttacggttc ctggccttttt gctggccttt     1860 tgctcacatg ttctttcctg cgttatcccc tgattctgtg ataaccgta ttaccgcctt      1920 tgagtgagct gataccgctc gccgcagccg aacgaccgag cgcagcgagt cagtgagcga     1980
ggaagcggaa gagcgcccaa tacgcaaacc gcctctcccc gcgcgttggc cgattcatta     2040
atgcagctgg cacgacaggt ttcccgactg gaaagcgggc agtgagcgca acgcaattaa     2100
tgtgagttac ctcactcatt aggcacccca ggctttacac tttatgcttc cggctcctat     2160
gttgtgtgga attgtgagcg gataacaatt tcacacagga aacagctatg accatgatta     2220
cgccaagctc ggaattaacc ctcactaaag ggaacaaaag ctgggtaccg gccccccct     2280 cgaggtcgag cttaagacgc gtttcttctt cagattccct catggagaaa gtgcggcaga     2340
tgtatatgac agagtcgcca gtttccaaga gacttttattc aggcacttcc atgataggca    2400
agagagaaga cccagagatg ttgttgtcct agttacacat ggtatttatt ccagagtatt     2460
```

```
cctgatgaaa tggtttagat ggacatacga agagtttgaa tcgtttacca atgttcctaa   2520
cgggagcgta atggtgatgg aactggacga atccatcaat agatacgtcc tgaggaccgt   2580
gctacccaaa tggactgatt gtgagggaga cctaactaca tagtgtttaa agattacgga   2640
tatttaactt acttagaata atgccatttt tttgagttat aataatccta cgttagtgtg   2700
agcgggattt aaactgtgag gaccttaata cattcagaca cttctgcggt atcaccctac   2760 ttattcccctt cgagattata tctaggaacc catcaggttg gtggaagatt acccgttcta   2820
agacttttca gcttcctcta ttgatgttac acctggacac cccttttctg gcatccagtt   2880
tttaatcttc agtggcatgt gagattctcc gaaattaatt aaagcaatca cacaattctc   2940
tcggatacca cctcggttga aactgacagg tggtttgtta cgcatgctaa tgcaaaggag   3000
cctatatacc tttggctcgg ctgctgtaac agggaatata aagggcagca taatttagga   3060
gtttagtgaa cttgcaacat ttactatttt cccttcttac gtaaatattt ttctttttaa   3120
ttctaaatca atcttttttca attttttgtt tgtattcttt tcttgcttaa atctataact   3180
acaaaaaaca catacataaa tctagaaaaa tgtctcaatt cttcttcaac cagagaaccc   3240
acttggtttc tgacgttatc gacggtgcta tcatcgcttc accatggaac aatttggcta   3300
gattggaatc tgacccagct atcagaatcg ttgttagaag agacttgaac aagaacaacg   3360
ttgctgttat ctctggtggt ggttctggtc acgaaccagc tcacgttggt ttcatcggta   3420
agggtatgtt gaccgctgct gtttgtggtg acgttttcgc ttctccatct gttgacgctg   3480
ttttgactgc tatccaagct gttaccggtg aagctggttg tttgttgatc gttaagaact   3540
acaccggtga cagattgaac ttcggtttgg ctgctgaaaa ggctagaaga ttgggttaca   3600
acgttgaaat gttgatcgtt ggtgacgaca tctctttgcc agacaacaag cacccaagag   3660
gtatcgctgg taccatcttg gttcacaaga tcgctggtta cttcgctgaa agaggttaca   3720
acttagctac cgttttgaga gaagctcaat acgctgcttc taacaccttc tctttgggtg   3780
ttgctttgtc ttcttgtcac ttgccacaag aaaccgacgc tgctccaaga caccacccag   3840
gtcacgctga attgggtatg ggtatccacg gtgaaccagg tgcttctgtt atcgacaccc   3900
aaaactctgc tcaagttgtt aacttgatgg ttgacaagtt gttggctgct ttgccagaaa   3960
ccggtagatt ggctgttatg atcaacaact gggtggtgt ttctgttgct gaaatggcta   4020
tcatcaccag agaattggct tcttctccat tgcactcaag aatcgactgg ttgatcggtc   4080
cagcttcttt ggtaaccgct ttggacatga agggttttctc tttgaccgct atcgttttgg   4140
aagaatctat cgaaaaggct ttgttgaccg aagttgaaac tctaactgg ccaaccccag   4200 ttccaccaag agaaatcacc tgtgttgttt cttctcacgc ttctgctaga gttgaattcc   4260
aaccatctgc taacgctttg gttgctggta tcgttgaatt ggttaccgct accttgtctg   4320
acttggaaac ccacttgaac gctttggacg ctaaggttgg tgacggtgac accggttcta   4380
ccttcgctgc tgctgctaga gaaatcgctt ctttgttgca cagacaacaa ttgccattga   4440
acaacttggc taccttgttc gctttgatcg gtgaaagatt gaccgttgtt atgggtggtt   4500
cttctggtgt tttgatgtct atcttcttca ccgctgctgg tcaaaagttg gaacaaggtg   4560
ctaacgttgt tgaagctttg aacaccggtt tggctcaaat gaagttctac ggtggtgctg   4620
acgaaggtga cagaaccatg atcgacgctt gcaaccagc tttgacctct tgttggctc   4680 aaccaaagaa cttgcaagct gctttcgacg ctgctcaagc tggtgctgaa agaacctgtt   4740
tgtcttctaa ggctaacgct ggtagagctt cttacttgtc ttctgaatct tgttgggta   4800
```

```
acatggaccc aggtgctcaa agattggcta tggttttcaa ggctttggct gaatctgaat    4860
tgggttaata aggtcgagac aaatcgctct taaatatata cctaaagaac attaaagcta    4920
tattataagc aaagatacgt aaattttgct tatattatta tacacatatc atatttctat    4980
attttttaaga tttggttata taatgtacgt aatgcaaagg aaataaattt tatacattat    5040
tgaacagcgt ccaagtaact acattatgtg cactaatagt ttagcgtcgt gaagacttta    5100
ttgtgtcgcg aaaagtaaaa attttaaaaa ttagagcacc ttgaacttgc gaaaaaggtt    5160
ctcatcaact gtttaaaacg tacgcctagg aagccttcga gcgtcccaaa accttctcaa    5220
gcaaggtttt cagtataatg ttacatgcgt acacgcgttt gtacagaaaa aaagaaaaa    5280
tttgaaatat aaataacgtt cttaatacta acataactat taaaaaaaat aaatagggac    5340
ctagacttca ggttgtctaa ctccttcctt ttcggttaga gcggatgtgg gaggagggcg    5400
tgaatgtaag cgtgacataa ctaattacat gatatcgaca aaggaaaagg ggcgcgcctt    5460
attcccattc ttgtaggaat ctttgaccgt attggtcagc aaccaacaaa gcagcgtaaa    5520
cttggtctgg ggtagcacca cctggcatgt tgtggatggt ttcaccttca gcacaagcag    5580
cttcagcaac gattctcatc ttagctggaa cgtcttcctt gatgtccaat tgagccaagg    5640
tgattggcaa accaacagcg tgagacaaag cagcaacggt tcgatttct tcaactggag    5700
cgttttccaa aaccaattgg gtcaaggtac cgaaagcaac cttttcaccg tggtagtagt    5760
ggtgagcgtc tgggatagcg gtcaaaccgt tgtgaacagc gtgagcagca gccaaaccac    5820
cagattcgaa accaacacca gacaagtagg tgttagcttc gataactctt tccaaagctg    5880
gggtaacaac gtgttgttca gcagccaaca tagccttttc accttcttcc aacaaggtgt    5940
tgtaacacaa ttcagccaaa gccaaagcag cttgggtaca cttaccacca gccatggtgg    6000
tagcaccaga tctagaacaa gctctagctt cgaaccaggt agccaaagcg tcaccgatac    6060
cagctgccaa caatctagct ggagcaccag caacgatctt ggtgtcaacg ataaccatgt    6120
ttgggttgtt tggcaacaac aagtatctgt cgaattcacc ttcgtcggtg tagataacag    6180
acaaagcaga acatggagcg tcggtagaag cgatggttgg agcgatagca actggaacac    6240
ccatgaagtg agccaaagcc ttagcggtgt ccaaggtctt accaccaccg atacccaaga    6300
tagcaccaca ttgagcggtt tcagcgatac ctctcaatct gtcgatttcg ttttgagaac    6360
attcaccacc gaatggagcg atttcaacaa ccaaaccagc gtccttgaaa gacttttcaa    6420
cggtagattg agcgaaaccc aaaacgaact tgtcaccaac aaccaaccat cttttcagcca    6480
atggcttcaa gtattcaccc aatctgttga taacgtcagc accttggatg tacttacctg    6540
gagattggat gattctgtcc attttctgca gttaattcag taaattttcg atcttgggaa    6600
gaaaaagca gtaagcgtga aaatctaaa agctgatgta gtagaagatc ctattctta    6660
acaaagattg acctttctt tttcttcttg gtttgagtag aaagggaag gaagaataca    6720
agagagagga aaaaaggaa gataaaaaga gagcgtgata taaatgaata tatattaaac    6780
aagagagatt gggaaggaaa ggatcaaaca aacccaaaaa tatttcaaaa aggagagaga    6840
gaggcgagtt tggttttcaaa acggtttatt tatttatgca agaggacgtg gaagaaaaag    6900
aagaaggaag aaaaaaattt gaaagaaaaa aacgcgtggc gggtaaagaa gaaatggaa    6960
aatagaggcc gggtgacaga gaaatattga gggttaattg gaaaatatgt tagggtgagg    7020
catatgtttt taagggtttt gaggatccga taaggaagaa tgtaggttaa atgttgtgca    7080
ttaattgctg tggcagctta cccgcttccc cacacattta ctagtctcga gctcttcaac    7140
tcaagacgca cagatattat aacatctgca taataggcat ttgcaagaat tactcgtgag    7200
```

```
taaggaaaga gtgaggaact atcgcatacc tgcatttaaa gatgccgatt tgggcgcgaa   7260
tcctttattt tggcttcacc ctcatactat tatcagggcc agaaaaagga agtgtttccc   7320
tccttcttga attgatgtta ccctcataaa gcacgtggcc tcttatcgag aaagaaatta   7380
ccgtcgctcg tgatttgttt gcaaaaagaa caaaactgaa aaaacccaga cacgctcgac   7440
ttcctgtctt cctattgatt gcagcttcca atttcgtcac acaacaaggt cctagcgacg   7500
gctcacaggt tttgtaacaa gcaatcgaag gttctggaat ggcgggaaag ggtttagtac   7560
cacatgctat gatgcccact gtgatctcca gagcaaagtt cgttcgatcg tactgttact   7620
ctctctcttt caaacagaat tgtccgaatc gtgtgacaac aacagcctgt tctcacacac   7680
tcttttcttc taaccagggg ggtggtttag tttagtagaa cctcgtgaaa cttacattta   7740
catatatata aacttgcata aattggtcaa tgcaagaaat acatatttgg tcttttctaa   7800
ttcgtagttt ttcaagttct tagatgcttt cttttctct tttttacaga tcatcaagga   7860
agtaattatc tactttttac aacaaatata tctagaaaat ggctgttacc aacgttgctg   7920
aattgaacgc tttggttgaa agggttaaga aggctcaaag agaatacgct tctttcaccc   7980
aagaacaagt tgacaagatc ttcagagctg ctgctttggc tgctgctgac gctagaatcc   8040
cattggctaa gatggctgtt gctgaatctg gtatgggtat cgttgaagac aaggttatca   8100
agaaccactt cgcttctgaa tacatctaca acgcttacaa ggacgaaaag acctgtggtg   8160
ttttgtcaga agacgacacc ttcggtacca tcaccatcgc tgaaccaatc ggtatcatct   8220
gtggtatcgt tccaaccacc aacccaacct ctaccgctat cttcaagtct ttgatctctt   8280
tgaagaccag aaacgctatc atcttctctc cacacccaag agctaaagac gctaccaaca   8340
aggctgctga catcgttttg caagctgcta tcgctgctgg tgctccaaag gacttgatcg   8400
gttggatcga ccaaccatct gttgaattgt ctaacgcttt gatgcaccac ccagacatca   8460
acttgatctt ggctaccggt ggtccaggta tggttaaggc tgcttactct tctggtaagc   8520
cagctatcgg tgttggtgct ggtaacaccc cagttgttat cgacgaaacc gctgacatca   8580
agagagctgt tgcttctgtt ttgatgtcta agaccttcga caacggtgtt atctgtgctt   8640
ctgaacaatc tgttgttgtt gttgactctg tttacgacgt tgttagagaa agattcgcta   8700
cccacggtgg ttacttgttg caaggtaagg aattgaaggc tgttcaagac gttatcttga   8760
agaacggtgc tttgaacgct gctatcgttg gtcaaccagc ttacaagatc gctgaattag   8820
ctggtttctc tgttccagaa acaccaagaa tcttgatcgg tgaagttacc gttgttgacg   8880
aatctgaacc attcgctcac gaaaagttgt ctccaacctt ggctatgtac agagctaagg   8940
acttcgaaga cgctgttgaa aaagctgaaa agttggttgc tatgggtggt attggtcaca   9000
cctcttgttt gtacaccgac caagacaacc aaccagctag agtttcttac ttcggtcaaa   9060
agatgaagac cgctagaatc ttgatcaaca ccccagcttc tcaaggtggt atcggtgact   9120
tgtacaactt caagttggct ccatctttga ccttgggttg tggttcttgg ggtggtaact   9180
ctatctctga aaacgttggt ccaaagcact tgatcaacaa gaagaccgtt gctaagagag   9240
ctgaaaacat tgttgtggcac aagttgccaa aatctatcta cttcagaaga ggttctttgc   9300
caatcgcttt ggacgaagtt atcaccgacg gtcacaagag agctttgatc gttaccgaca   9360
gattcttgtt caacaacggt tacgctgacc aaatcacctc tgttttgaag gctgctggtg   9420
ttgaaaccga gttttcttc gaagttgaag ctgacccaac cttgtctatc gttagaaagg   9480
gtgctgaatt ggctaactct ttcaagccag acgttatcat cgctttgggt ggtggttctc   9540
```

```
caatggacgc tgctaagatc atgtgggtta tgtacgaaca cccagaaacc cacttcgaag    9600
aattggcttt gagattcatg gacatcagaa agagaatcta caagttccca agatgggtg    9660 ttaaggctaa gatgatcgct gttaccacca cctctggtac cggttctgaa gttaccccat    9720
tcgctgttgt taccgacgac gctaccggtc aaaagtaccc attggctgac tacgctttga    9780
ccccagacat ggctatcgtt gacgctaact tggttatgga catgccaaag tctttgtgtg    9840 cttttcggtgg tttggacgct gttacccacg ctatggaagc ttacgtttct gttttggctt    9900
ctgaattctc tgacggtcaa gctttgcaag ctttgaagtt gttgaaggaa tacttgccag    9960
cttcttacca cgaaggttct aagaacccag ttgctagaga aagagttcac tctgctgcta   10020
ccatcgctgg tatcgctttc gctaacgctt tcttgggtgt tgtcactct atggctcaca   10080 agttgggttc tcaattccac atcccacacg gtttggctaa cgctttgttg atctgtaacg   10140
ttatcagata caacgctaac gacaacccaa ccaagcaaac cgcttctct caatacgaca   10200 gaccacaagc tagaagaaga tacgctgaaa tcgctgacca cttgggtttg tctgctccag   10260
gtgacagaac cgctgcaaag atcgaaaagt tgttggcttg gttggaaacc ttgaaggctg   10320
aattgggtat cccaaagtct atcagagaag ctggtgttca agaagctgac ttcttggcta   10380
acgttgacaa gttgtctgaa gacgctttcg acgaccaatg taccggtgct aacccaagat   10440
acccattgat ctctgaattg aagcaaatct tgttggacac ctactacggt agagactacg   10500
ttgaaggtga aaccgctgct aagaaggaag ctgctccagc taaggctgaa aagaaggcta   10560
agaagtctgc ttagcttaag cgcgcgaatt tcttatgatt tatgattttt attattaaat   10620
aagttataaa aaaataagt gtatacaaat tttaagtga ctcttaggtt ttaaaacgaa   10680
aattcttatt cttgagtaac tctttcctgt aggtcaggtt gctttctcag gtatagcatg   10740
aggtcgctct tattgaccac acctctaccg gcatgccgag caaatgcctg caaatcgctc   10800
cccatttcac ccaattgtag atatgctaac tccagcaatg agttgatgaa tctcggtgtg   10860
tattttatgt cctcagagga caacacctgt tgtaatcgtt cttccacacg tacgaagctt   10920
aaaagggcga attctgcaga tatccatcac actggcggcc gcatgctagc tccggattat   10980
cgatgataag ctgtcaaaga tgagaattaa ttccacggac tatagactat actagatact   11040
ccgtctactg tacgatacac ttccgctcag gtccttgtcc tttaacgagg ccttaccact   11100
cttttgttac tctattgatc cagctcagca aaggcagtgt gatctaagat tctatcttcg   11160
cgatgtagta aaactagcta gaccgagaaa gagactagaa atgcaaaagg cacttctaca   11220
atggctgcca tcattattat ccgatgtgac gctgcagctt ctcaatgata ttcgaatacg   11280
ctttgaggag atacagccta atatccgaca aactgtttta cagatttacg atcgtacttg   11340
ttacccatca ttgaattttg aacatccgaa cctgggagtt ttccctgaaa cagatagtat   11400
atttgaacct gtataataat atatagtcta gcgctttacg gaagacaatg tatgtatttc   11460
ggttcctgga gaaactattg catctattgc ataggtaatc ttgcacgtcg catcccggt    11520 tcattttctg cgtttccatc ttgcacttca atagcatatc tttgttaacg aagcatctgt   11580
gcttcatttt gtagaacaaa aatgcaacgc gagagcgcta attttcaaa caagaatct    11640 gagctgcatt tttacagaac agaaatgcaa cgcgaaagcg ctattttacc aacgaagaat   11700
ctgtgcttca tttttgtaaa acaaaaatgc aacgcgacga gcgctaat ttttcaaaca   11760 aagaatctga gctgcatttt tacagaacag aaatgcaacg cgagagcgct attttaccaa   11820
caaagaatct atacttcttt tttgttctac aaaaatgcat cccgagagcg ctattttct    11880 aacaaagcat cttagattac tttttttctc ctttgtgcgc tctataatgc agtctcttga  11940
```

```
taacttttg  cactgtaggt  ccgttaaggt  tagaagaagg  ctactttggt  gtctattttc    12000
tcttccataa  aaaaagcctg  actccacttc  ccgcgtttac  tgattactag  cgaagctgcg    12060
ggtgcatttt  ttcaagataa  aggcatcccc  gattatattc  tataccgatg  tggattgcgc    12120
atactttgtg  aacagaaagt  gatagcgttg  atgattcttc  attggtcaga  aaattatgaa    12180
cggtttcttc  tattttgtct  ctatatacta  cgtataggaa  atgtttacat  tttcgtattg    12240
ttttcgattc  actctatgaa  tagttcttac  tacaattttt  ttgtctaaag  agtaatacta    12300
gagataaaca  taaaaaatgt  agaggtcgag  tttagatgca  agttcaagga  gcgaaaggtg    12360
gatgggtagg  ttatataggg  atatagcaca  gagatatata  gcaaagagat  actttttgagc   12420
aatgtttgtg  gaagcggtat  tcgcaatgcc  ggctttcccc  gtcaagctct  aaatcggggg    12480
ctccctttag  ggttccgatt  tagtgcttta  cggcacctcg  accccaaaaa  acttgattag    12540
ggtgatggtt  cacgtagtgg  gccatcgccc  tgatagacgg  tttttcgccc  tttgacgttg    12600
gagtccacgt  tctttaatag  tggactcttg  ttccaaactg  gaacaacact  caaccctatc    12660
tcggtctatt  cttttgattt  ataagggatt  ttgccgattt  cggcctattg  gttaaaaaat    12720
gagctgattt  aacaaaaatt  taacgcgaat  tttaacaaaa  tattaacgtt  tacaatttcc    12780
tgatgcggta  ttttctcctt  acgcatctgt  gcggtatttc  acaccgcata  tgatccgtcg    12840
agttcaagag  aaaaaaaaag  aaaaagcaaa  aagaaaaaag  gaaagcgcgc  ctcgttcaga    12900
atgacacgta  tagaatgatg  cattaccttg  tcatcttcag  tatcatactg  ttcgtataca    12960
tacttactga  cattcatagg  tatacatata  tacacatgta  tatatatcgt  atgctgcagc    13020
tttaaataat  cggtgtcact  acataagaac  acctttggtg  gagggaacat  cgttggtacc    13080
attgggcgag  gtggcttctc  ttatggcaac  cgcaagagcc  ttgaacgcac  tctcactacg    13140
gtgatgatca  ttcttgcctc  gcagacaatc  aacgtggagg  gtaattctgc  tagcctctgc    13200
aaagctttca  agaaaatgcg  ggatcatctc  gcaagagaga  tctcctactt  tctcccttg    13260
caaaccaagt  tcgacaactg  cgtacggcct  gttcgaaaga  tctaccaccg  ctctggaaag    13320
tgcctcatcc  aaaggcgcaa  atcctgatcc  aaaccttttt  actccacgcg  ccagtagggc    13380
ctctttaaaa  gcttgaccga  gagcaatccc  gcagtcttca  gtggtgtgat  ggtcgtctat    13440
gtgtaagtca  ccaatgcact  caacgattag  cgaccagccg  gaatgcttgg  ccagagcatg    13500
tatcatatgg  tccagaaacc  ctatacctgt  gtggacgtta  atcacttgcg  attgtgtggc    13560
ctgttctgct  actgcttctg  cctctttttc  tgggaagatc  gagtgctcta  tcgctagggg    13620
accacccttt  aaagagatcg  caatctgaat  cttggtttta  tttgtaatac  gctttactag    13680
ggctttctgc  tctgtcatct  ttgccttcgt  ttatcttgcc  tgctcatttt  ttagtatatt    13740
cttcgaagaa  atcacattac  tttatataat  gtataattca  ttatgtgata  atgccaatcg    13800
ctaagaaaaa  aaaagagtca  tccgctaggt  ggaaaaaaaa  aaatgaaaat  cattaccgag    13860
gcataaaaaa  atatagagtg  tactagagga  ggccaagagt  aatagaaaaa  gaaaattgcg    13920
ggaaaggact  gtgttatgac  ttccctgact  aatgccgtgt  tcaaacgata  cctggcagtg    13980
actcctagcg  ctcaccaagc  tcttaaaacg  gaattatggt  gcactctcag  tacaatctgc    14040
tctgatgccg  catagttaag  ccagcccga  cacccgccaa  cacccgctga  cgcgccctga    14100
cgggcttgtc  tgctcccggc  atccgcttac  agacaagctg  tgaccgtctc  cgggagctgc    14160
atgtgtcaga  ggttttcacc  gtcatcaccg  aaacgcgcga                            14200
```

<210> SEQ ID NO 38

<211> LENGTH: 3042
<212> TYPE: DNA
<213> ORGANISM: Artificial
<220> FEATURE:
<223> OTHER INFORMATION: pRNDAK

<400> SEQUENCE: 38

```
ggatccacta gtaacggccg ccagtgtgct ggaattcgcc cttctcgagc ttaagacgcg      60
tttcttcttc agattccctc atggagaaag tgcggcagat gtatatgaca gagtcgccag     120
tttccaagag actttattca ggcacttcca tgataggcaa gagagaagac ccagagatgt     180
tgttgtccta gttacacatg gtatttattc cagagtattc ctgatgaaat ggtttagatg     240
gacatacgaa gagtttgaat cgtttaccaa tgttcctaac gggagcgtaa tggtgatgga     300
actggacgaa tccatcaata gatacgtcct gaggaccgtg ctacccaaat ggactgattg     360
tgagggagac ctaactacat agtgtttaaa gattacggat atttaactta cttagaataa     420
tgccattttt ttgagttata ataatcctac gttagtgtga gcgggattta aactgtgagg     480
accttaatac attcagacac ttctgcggta tcaccctact tattcccttc gagattatat     540
ctaggaaccc atcaggttgg tggaagatta cccgttctaa gacttttcag cttcctctat     600
tgatgttaca cctggacacc cttttctgg catccagttt ttaatcttca gtggcatgtg      660
agattctccg aaattaatta aagcaatcac acaattctct cggataccac ctcggttgaa     720
actgacaggt ggtttgttac gcatgctaat gcaaggagc ctatatacct ttggctcggc      780
tgctgtaaca gggaatataa agggcagcat aatttaggag tttagtgaac ttgcaacatt     840
tactattttc ccttcttacg taaatatttt tctttttaat tctaaatcaa tcttttttcaa    900
ttttttgttt gtattctttt cttgcttaaa tctataacta caaaaaacac atacataaat     960
ctagaaaatg tccgctaaat cgtttgaagt cacagatcca gtcaattcaa gtctcaaagg    1020
gtttgccctt gctaacccct ccattacgct ggtccctgaa gaaaaattc tcttcagaaa     1080
gaccgattcc gacaagatcg cattaatttc tggtggtggt agtggacatg aacctacaca    1140
cgccggtttc attggtaagg gtatgttgag tggcgccgtg gttggcgaaa ttttgcatc     1200
ccctcaaca aaacagattt taaatgcaat ccgtttagtc aatgaaaatg cgtctggcgt     1260
tttattgatt gtgaagaact acacaggtga tgttttgcat tttggtctgt ccgctgagag    1320
agcaagagcc ttgggtatta actgccgcgt tgctgtcata ggtgatgatg ttgcagttgg    1380
cagagaaaag ggtggtatgg ttggtagaag agcattggca ggtaccgttt tggttcataa    1440
gattgtaggt gccttcgcag aagaatattc tagtaagtat ggcttagacg gtacagctaa    1500
agtggctaaa attatcaacg acaatttggt gaccattgga tcttctttag accattgtaa    1560
agttcctggc aggaaattcg aaagtgaatt aaacgaaaaa caaatggaat tgggtatggg    1620
tattcataac gaacctggtg tgaaagtttt agaccctatt ccttctaccg aagacttgat    1680
ctccaagtat atgctaccaa aactattgga tccaaacgat aaggatagag cttttgtaaa    1740
gtttgatgaa gatgatgaag ttgtcttgtt agttaacaat ctcggcggtg tttctaattt    1800
tgttattagt tctatcactt ccaaaactac ggatttctta aggaaaaatt acaacataac    1860
cccggttcaa acaattgctg gcacattgat gacctccttc aatggtaatg ggttcagtat    1920
cacattacta aacgccacta aggctacaaa ggctttgcaa tctgattttg aggagatcaa    1980
atcagtacta gacttgttga acgcatttac gaacgcaccg ggctggccaa ttgcagattt    2040
tgaaaagact tctgccccat ctgttaacga tgacttgtta cataatgaag taacagcaaa    2100
ggccgtcggt acctatgact ttgacaagtt tgctgagtgg atgaagagtg gtgctgaaca    2160
```

```
agttatcaag agcgaaccgc acattacgga actagacaat caagttggtg atggtgattg    2220
tggttacact ttagtggcag gagttaaagg catcaccgaa aaccttgaca agctgtcgaa    2280
ggactcatta tctcaggcgg ttgcccaaat ttcagatttc attgaaggct caatgggagg    2340
tacttctggt ggtttatatt ctattctttt gtcgggtttt tcacacggat taattcaggt    2400
ttgtaaatca aaggatgaac ccgtcactaa ggaaattgtg gctaagtcac tcggaattgc    2460
attggatact ttatacaaat atacaaaggc aaggaaggga tcatccacca tgattgatgc    2520
tttagaacca ttcgttaaag aatttactgc atctaaggat ttcaataagg cggtaaaagc    2580
tgcagaggaa ggtgctaaat ccactgctac attcgaggcc aaatttggca gagcttcgta    2640
tgtcggcgat tcatctcaag tagaagatcc tggtgcagta ggcctatgtg agttttgaa    2700 gggggttcaa agcgccttgt aagtcgagac aaatcgctct taaatatata cctaaagaac    2760
attaaagcta tattataagc aaagatacgt aaattttgct tatattatta tacacatatc    2820
atatttctat atttttaaga tttggttata taatgtacgt aatgcaaagg aaataaattt    2880
tatacattat tgaacagcgt ccaagtaact acattatgtg cactaatagt ttagcgtcgt    2940
gaagacttta ttgtgtcgcg aaaagtaaaa attttaaaaa ttagagcacc ttgaacttgc    3000
gaaaaaggtt ctcatcaact gtttaaaacg tacgaagctt aa                       3042

<210> SEQ ID NO 39
<211> LENGTH: 14291
<212> TYPE: DNA
<213> ORGANISM: Artificial
<220> FEATURE:
<223> OTHER INFORMATION: pRN977

<400> SEQUENCE: 39
gacgaaaggg cctcgtgata cgcctatttt tataggttaa tgtcatgata ataagacgtc      60
aggtggcact tttcggggaa atgtgcgcgg aaccccctat tgtttatttt tctaaataca     120
ttcaaatatg tatccgctca tgagacaata accctgataa atgcttcaat aatattgaaa     180
aaggaagagt atgagtattc aacatttccg tgtcgccctt attccctttt ttgcggcatt     240
ttgccttcct gtttttgctc acccagaaac gctggtgaaa gtaaaagatg ctgaagatca     300
gttgggtgca cgagtgggtt acatcgaact ggatctcaac agcggtaaga tccttgagag     360
ttttcgcccc gaagaacgtt ttccaatgat gagcactttt aaagttctgc tatgtggcgc     420
ggtattatcc cgtattgacg ccgggcaaga gcaactcggt cgccgcatac actattctca     480
gaatgacttg gttgagtact caccagtcac agaaaagcat cttacggatg gcatgacagt     540
aagagaatta tgcagtgctg ccataaccat gagtgataac actgcggcca acttacttct     600
gacaacgatc ggaggaccga aggagctaac cgcttttttt cacaacatgg gggatcatgt     660
aactcgcctt gatcgttggg aaccggagct gaatgaagcc ataccaaacg acgagcgtga     720
caccacgatg cctgtagcaa tggcaacaac gttgcgcaaa ctattaactg gcgaactact     780
tactctagct tcccggcaac aattaataga ctggatggag gcggataaag ttgcaggacc     840
acttctgcgc tcggcccttc cggctggctg gtttattgct gataaatctg gagccggtga     900
gcgtgggtct cgcggtatca ttgcagcact ggggccagat ggtaagccct cccgtatcgt     960
agttatctac acgacgggca gtcaggcaac tatggatgaa cgaaatagac agatcgctga    1020
gataggtgcc tcactgatta agcattggta actgtcagac caagtttact catatatact    1080
ttagattgat ttaaaacttc atttttaatt taaaaggatc taggtgaaga tccttttga     1140
```

```
taatctcatg accaaaatcc cttaacgtga gttttcgttc cactgagcgt cagaccccgt    1200
agaaaagatc aaaggatctt cttgagatcc ttttttcctg cgcgtaatct gctgcttgca    1260
aacaaaaaaa ccaccgctac cagcggtggt ttgtttgccg gatcaagagc taccaactct    1320
ttttccgaag gtaactggct tcagcagagc gcagatacca atactgtcc ttctagtgta    1380 gccgtagtta ggccaccact tcaagaactc tgtagcaccg cctacatacc tcgctctgct    1440
aatcctgtta ccagtggctg ctgccagtgg cgataagtcg tgtcttaccg ggttggactc    1500
aagacgatag ttaccggata aggcgcagcg gtcgggctga acggggggtt cgtgcacaca    1560
gcccagcttg gagcgaacga cctacaccga actgagatac ctacagcgtg agcattgaga    1620
aagcgccacg cttcccgaag ggagaaaggc ggacaggtat ccggtaagcg gcagggtcgg    1680
aacaggagag cgcacgaggg agcttccagg ggggaacgcc tggtatcttt atagtcctgt    1740
cgggtttcgc cacctctgac ttgagcgtcg attttttgtga tgctcgtcag ggggggccgag    1800 cctatggaaa aacgccagca acgcggcctt tttacggttc ctggccttttt gctggccttt    1860 tgctcacatg ttctttcctg cgttatcccc tgattctgtg gataaccgta ttaccgcctt    1920
tgagtgagct gataccgctc gccgcagccg aacgaccgag cgcagcgagt cagtgagcga    1980
ggaagcggaa gagcgcccaa tacgcaaacc gcctctcccc cgcgcgttggc cgattcatta    2040 atgcagctgg cacgacaggt ttcccgactg gaaagcgggc agtgagcgca acgcaattaa    2100
tgtgagttac ctcactcatt aggcaccccca ggctttacac tttatgcttc cggctcctat    2160
gttgtgtgga attgtgagcg gataacaatt tcacacagga aacagctatg accatgatta    2220
cgccaagctc ggaattaacc ctcactaaag ggaacaaaag ctgggtaccg gccccccct    2280 cgaggtcgag cttaagacgc gtttcttctt cagattccct catggagaaa gtgcggcaga    2340
tgtatatgac agagtcgcca gtttccaaga gactttattc aggcacttcc atgataggca    2400
agagagaaga cccagagatg ttgttgtcct agttacacat ggtatttatt ccagagtatt    2460
cctgatgaaa tggtttagat ggacatacga agagtttgaa tcgtttacca atgttcctaa    2520
cgggagcgta atggtgatgg aactggacga atccatcaat agatacgtcc tgaggaccgt    2580
gctacccaaa tggactgatt gtgagggaga cctaactaca tagtgtttaa agattacgga    2640
tatttaactt acttagaata atgccatttt tttgagttat aataatccta cgttagtgtg    2700
agcgggattt aaactgtgag gaccttaata cattcagaca cttctgcggt atcaccctac    2760 ttattcccctt cgagattata tctaggaacc catcaggttg gtggaagatt acccgttcta    2820
agacttttca gcttcctcta ttgatgttac acctggacac ccctttttctg gcatccagtt    2880 tttaatcttc agtggcatgt gagattctcc gaaattaatt aaagcaatca cacaattctc    2940
tcggatacca cctcggttga aactgacagg tggtttgtta cgcatgctaa tgcaaaggag    3000
cctatatacc tttggctcgg ctgctgtaac agggaatata aagggcagca aatttagga    3060 gtttagtgaa cttgcaacat ttactatttt cccttcttac gtaaatattt ttcttttaa    3120 ttctaaatca atctttttca attttttgtt tgtattcttt tcttgcttaa atctataact    3180
acaaaaaaca catacataaa tctagaaaat gtccgctaaa tcgtttgaag tcacagatcc    3240
agtcaattca agtctcaaag ggtttgccct tgctaacccc tccattacgc tggtccctga    3300
agaaaaaatt ctcttcagaa agaccgattc cgacaagatc gcattaattt ctggtggtgg    3360
tagtggacat gaacctacac acgccggttt cattggtaag ggtatgttga gtggcgccgt    3420
ggttggcgaa atttttgcat cccccttcaac aaaaacagatt ttaaatgcaa tccgtttagt    3480
caatgaaaat gcgtctggcg ttttattgat tgtgaagaac tacacaggtg atgttttgca    3540
```

```
ttttggtctg tccgctgaga gagcaagagc cttgggtatt aactgccgcg ttgctgtcat    3600
aggtgatgat gttgcagttg gcagagaaaa gggtggtatg gttggtagaa gagcattggc    3660
aggtaccgtt ttggttcata agattgtagg tgccttcgca gaagaatatt ctagtaagta    3720
tggcttagac ggtacagcta aagtggctaa aattatcaac gacaatttgg tgaccattgg    3780
atcttcttta gaccattgta aagttcctgg caggaaattc gaaagtgaat aaacgaaaa     3840 acaaatggaa ttgggtatgg gtattcataa cgaacctggt gtgaaagttt tagaccctat    3900
tccttctacc gaagacttga tctccaagta tatgctacca aaactattgg atccaaacga    3960
taaggataga gcttttgtaa agtttgatga agatgatgaa gttgtcttgt tagttaacaa    4020
tctcggcggt gtttctaatt ttgttattag ttctatcact tccaaaacta cggatttctt    4080
aaaggaaaat tacaacataa ccccggttca acaattgct ggcacattga tgacctcctt    4140
caatggtaat gggttcagta tcacattact aaacgccact aaggctacaa aggctttgca    4200
atctgatttt gaggagatca aatcagtact agacttgttg aacgcattta cgaacgcacc    4260
gggctggcca attgcagatt ttgaaaagac ttctgcccca tctgttaacg atgacttgtt    4320
acataatgaa gtaacagcaa aggccgtcgg tacctatgac tttgacaagt ttgctgagtg    4380
gatgaagagt ggtgctgaac aagttatcaa gagcgaaccg cacattacgg aactagacaa    4440
tcaagttggt gatggtgatt gtggttacac tttagtggca ggagttaaag gcatcaccga    4500
aaaccttgac aagctgtcga aggactcatt atctcaggcg gttgcccaaa tttcagattt    4560
cattgaaggc tcaatgggag gtacttctgg tggtttatat tctattcttt tgtcgggttt    4620
ttcacacgga ttaattcagg tttgtaaatc aaaggatgaa cccgtcacta aggaaattgt    4680
ggctaagtca ctcggaattg cattggatac tttatacaaa tatacaaagg caaggaaggg    4740
atcatccacc atgattgatg ctttagaacc attcgttaaa gaatttactg catctaagga    4800
tttcaataag gcggtaaaag ctgcagagga aggtgctaaa tccactgcta cattcgaggc    4860
caaatttggc agagcttcgt atgtcggcga ttcatctcaa gtagaagatc ctggtgcagt    4920
aggcctatgt gagttttga aggggttca aagcgccttg taagtcgaga caaatcgctc    4980
ttaaatatat acctaaagaa cattaaagct atattataag caaagatacg taaattttgc    5040
ttatattatt atacacatat catatttcta tattttaag atttggttat ataatgtacg    5100
taatgcaaag gaaataaatt ttatacatta ttgaacagcg tccaagtaac tacattatgt    5160
gcactaatag tttagcgtcg tgaagactt attgtgtcgc gaaaagtaaa aattttaaaa    5220
attagagcac cttgaacttg cgaaaaaggt tctcatcaac tgtttaaaac gtacgcctag    5280
gaagccttcg agcgtcccaa aaccttctca agcaaggttt tcagtataat gttacatgcg    5340
tacacgcgtt tgtacagaaa aaaagaaaa atttgaaata taataacgt tcttaatact    5400 aacataacta ttaaaaaaaa taaataggga cctagacttc aggttgtcta actccttcct    5460
tttcggttag agcggatgtg ggaggagggc gtgaatgtaa gcgtgacata actaattaca    5520
tgatatcgac aaaggaaaag gggcgcgcct tattcccatt cttgtaggaa tctttgaccg    5580
tattggtcag caaccaacaa agcagcgtaa acttggtctg gggtagcacc acctggcatg    5640
ttgtggatgg tttcaccttc agcacaagca gcttcagcaa cgattctcat cttagctgga    5700
acgtcttcct tgatgtccaa ttgagccaag gtgattggca aaccaacagc gtgagacaaa    5760
gcagcaacgg tttcgatttc ttcaactgga gcgttttcca aaaccaattg ggtcaaggta    5820
ccgaaagcaa ccttttcacc gtggtagtag tggtgagcgt ctgggatagc ggtcaaaccg    5880
```

```
ttgtgaacag cgtgagcagc agccaaacca ccagattcga aaccaacacc agacaagtag    5940
gtgttagctt cgataactct ttccaaagct ggggtaacaa cgtgttgttc agcagccaac    6000 atagccttt  caccttcttc caacaaggtg ttgtaacaca attcagccaa agccaaagca    6060
gcttgggtac acttaccacc agccatggtg gtagcaccag atctagaaca agctctagct    6120
tcgaaccagg tagccaaagc gtcaccgata ccagctgcca acaatctagc tggagcacca    6180
gcaacgatct tggtgtcaac gataaccatg tttgggttgt ttggcaacaa caagtatctg    6240
tcgaattcac cttcgtcggt gtagataaca gacaaagcag aacatggagc gtcggtagaa    6300
gcgatggttg gagcgatagc aactggaaca cccatgaagt gagccaaagc cttagcggtg    6360
tccaaggtct taccaccacc gataccaag  atagcaccac attgagcggt ttcagcgata    6420
cctctcaatc tgtcgatttc gttttgagaa cattcaccac cgaatggagc gatttcaaca    6480
accaaaccag cgtccttgaa agacttttca acggtagatt gagcgaaacc caaaacgaac    6540
ttgtcaccaa caaccaacca tctttcagcc aatggcttca agtattcacc caatctgttg    6600
ataacgtcag caccttggat gtacttacct ggagattgga tgattctgtc catttttctgc   6660 agttaattca gtaaattttc gatcttggga agaaaaaagc agtaagcgtg aaaaatctaa    6720
aagctgatgt agtagaagat cctattcttt aacaaagatt gaccttttct ttttcttctt    6780
ggtttgagta gaaaggggaa ggaagaatac aagagagagg aaaaaaagga agataaaaag    6840
agagcgtgat ataatgaat atatattaaa caagagagat tgggaaggaa aggatcaaac     6900
aaacccaaaa atatttcaaa aaggagagag agaggcgagt ttggtttcaa aacggtttat    6960
ttatttatgc aagaggacgt ggaagaaaaa gaagaaggaa gaaaaaaatt tgaaagaaaa    7020
aaacgcgtgg cgggtaaaga agaaaatgga aaatagaggc cgggtgacag agaaatattg    7080
agggttaatt ggaaaatatg ttagggtgag gcatatgttt ttaaggggttt tgaggatccg   7140 ataaggaaga atgtaggtta aatgttgtgc attaattgct gtggcagctt acccgcttcc    7200
ccacacattt actagtctcg agctcttcaa ctcaagacgc acagatatta taacatctgc    7260
ataataggca tttgcaagaa ttactcgtga gtaaggaaag agtgaggaac tatcgcatac    7320
ctgcatttaa agatgccgat ttgggcgcga atcctttatt ttggcttcac cctcatacta    7380
ttatcagggc cagaaaaagg aagtgttttcc ctccttcttg aattgatgtt accctcataa   7440
agcacgtggc ctcttatcga gaaagaaatt accgtcgctc gtgatttgtt tgcaaaaaga    7500
acaaaactga aaaaacccag acacgctcga cttcctgtct tcctattgat tgcagcttcc    7560
aatttcgtca cacaacaagg tcctagcgac ggctcacagg ttttgtaaca agcaatcgaa    7620
ggttctggaa tggcgggaaa gggtttagta ccacatgcta tgatgcccac tgtgatctcc    7680
agagcaaagt tcgttcgatc gtactgttac tctctctctt tcaaacagaa ttgtccgaat    7740
cgtgtgacaa caacagcctg ttctcacaca ctcttttctt ctaaccaagg gggtggttta    7800
gtttagtaga acctcgtgaa acttacattt acatatatat aaacttgcat aaattggtca    7860
atgcaagaaa tacatatttg gtcttttcta attcgtagtt tttcaagttc ttagatgctt    7920 tcttttctc  tttttacag  atcatcaagg aagtaattat ctacttttta caacaaatat    7980
atctagaaaa tggctgttac caacgttgct gaattgaacg ctttggttga aagggttaag    8040
aaggctcaaa gagaatacgc ttcttcacc  caagaacaag ttgacaagat cttcagagct    8100
gctgctttgg ctgctgctga cgctagaatc ccattggcta agatggctgt tgctgaatct    8160
ggtatgggta tcgttgaaga caaggttatc aagaaccact tcgcttctga atacatctac    8220
aacgcttaca aggacgaaaa gacctgtggt gttttgtcag aagacgacac cttcggtacc    8280
```

```
atcaccatcg ctgaaccaat cggtatcatc tgtggtatcg ttccaaccac caacccaacc    8340
tctaccgcta tcttcaagtc tttgatctct ttgaagacca gaaacgctat catcttctct    8400
ccacacccaa gagctaaaga cgctaccaac aaggctgctg acatcgtttt gcaagctgct    8460
atcgctgctg tgctccaaa ggacttgatc ggttggatcg accaaccatc tgttgaattg    8520
tctaacgctt tgatgcacca cccagacatc aacttgatct tggctaccgg tggtccaggt    8580
atggttaagg ctgcttactc ttctggtaag ccagctatcg tgttggtgc tggtaacacc    8640 ccagttgtta tcgacgaaac cgctgacatc aagagagctg ttgcttctgt tttgatgtct    8700
aagaccttcg acaacggtgt tatctgtgct tctgaacaat ctgttgttgt tgttgactct    8760
gtttacgacg ctgttagaga aagattcgct acccacggtg ttacttgtt gcaaggtaag    8820 gaattgaagg ctgttcaaga cgttatcttg aagaacggtg ctttgaacgc tgctatcgtt    8880
ggtcaaccag cttacaagat cgctgaatta gctggtttct ctgttccaga aaacaccaag    8940
atcttgatcg tgaagttac cgttgttgac gaatctgaac cattcgctca cgaaaagttg    9000
tctccaacct tggctatgta cagagctaag gacttcgaag acgctgttga aaaagctgaa    9060
aagttggttg ctatgggtgg tattggtcac acctcttgtt tgtacaccga ccaagacaac    9120
caaccagcta gagtttctta cttcggtcaa aagatgaaga ccgctagaat cttgatcaac    9180
accccagctt ctcaaggtgg tatcggtgac ttgtacaact tcaagttggc tccatctttg    9240
accttgggtt gtggttcttg gggtggtaac tctatctctg aaaacgttgg tccaaagcac    9300
ttgatcaaca agaagaccgt tgctaagaga gctgaaaaca tgttgtggca caagttgcca    9360
aaatctatct acttcagaag aggttctttg ccaatcgctt tggacgaagt tatcaccgac    9420
ggtcacaaga gagctttgat cgttaccgac agattcttgt tcaacaacgg ttacgctgac    9480
caaatcacct ctgttttgaa ggctgctggt gttgaaaccg aagttttctt cgaagttgaa    9540
gctgacccaa ccttgtctat cgttagaaag ggtgctgaat tggctaactc tttcaagcca    9600
gacgttatca tcgctttggg tggtggttct ccaatggacg ctgctaagat catgtgggtt    9660
atgtacgaac acccagaaac ccacttcgaa gaattggctt tgagattcat ggacatcaga    9720
aagagaatct acaagttccc aaagatgggt gttaaggcta gatgatcgc tgttaccacc    9780 acctctggta ccggttctga agttacccca ttcgctgttg ttaccgacga cgctaccggt    9840
caaaagtacc cattggctga ctacgctttg accccagaca tggctatcgt tgacgctaac    9900
ttggttatgg acatgccaaa gtctttgtgt gctttcggtg gtttggacgc tgttacccac    9960
gctatggaag cttacgtttc tgttttggct tctgaattct ctgacggtca agctttgcaa   10020
gctttgaagt tgttgaagga atacttgcca gcttcttacc acgaaggttc taagaaccca   10080
gttgctagag aaaagagttca ctctgctgct accatcgctg gtatcgcttt cgctaacgct   10140
ttcttgggtg tttgtcactc tatggctcac aagttgggtt ctcaattcca catcccacac   10200 ggttggcta acgctttgtt gatctgtaac gttatcagat acaacgctaa cgacaaccca   10260
accaagcaaa ccgctttctc tcaatacgac agaccacaag ctagaagaag atacgctgaa   10320
atcgctgacc acttgggttt gtctgctcca ggtgacagaa ccgctgcaaa gatcgaaaag   10380
ttgttggctt ggttggaaac cttgaaggct gaattgggta tcccaaagtc tatcagagaa   10440
gctggtgttc aagaagctga cttcttggct aacgttgaca agttgtctga agacgctttc   10500
gacgaccaat gtaccggtgc taacccaaga tacccattga tctctgaatt gaagcaaatc   10560
ttgttggaca cctactacgg tagagactac gttgaaggtg aaaccgctgc taagaaggaa   10620
```

```
gctgctccag ctaaggctga aaagaaggct aagaagtctg cttagcttaa gcgcgcgaat    10680
ttcttatgat ttatgatttt tattattaaa taagttataa aaaaaataag tgtatacaaa    10740
ttttaaagtg actcttaggt tttaaaacga aaattcttat tcttgagtaa ctctttcctg    10800
taggtcaggt tgctttctca ggtatagcat gaggtcgctc ttattgacca cacctctacc    10860
ggcatgccga gcaaatgcct gcaaatcgct ccccatttca cccaattgta gatatgctaa    10920
ctccagcaat gagttgatga atctcggtgt gtattttatg tcctcagagg acaacacctg    10980
ttgtaatcgt tcttccacac gtacgaagct taaaagggcg aattctgcag atatccatca    11040
cactggcggc cgcatgctag ctccggatta tcgatgataa gctgtcaaag atgagaatta    11100
attccacgga ctatagacta tactagatac tccgtctact gtacgataca cttccgctca    11160
ggtccttgtc ctttaacgag gccttaccac tcttttgtta ctctattgat ccagctcagc    11220
aaaggcagtg tgatctaaga ttctatcttc gcgatgtagt aaaactagct agaccgagaa    11280
agagactaga aatgcaaaag gcacttctac aatggctgcc atcattatta tccgatgtga    11340
cgctgcagct tctcaatgat attcgaatac gctttgagga gatacagcct aatatccgac    11400
aaactgtttt acagatttac gatcgtactt gttacccatc attgaatttt gaacatccga    11460
acctgggagt tttccctgaa acagatagta tatttgaacc tgtataataa tatatagtct    11520
agcgctttac ggaagacaat gtatgtattt cggttcctgg agaaactatt gcatctattg    11580
cataggtaat cttgcacgtc gcatccccgg ttcattttct gcgtttccat cttgcacttc    11640
aatagcatat ctttgttaac gaagcatctg tgcttcattt tgtagaacaa aaatgcaacg    11700
cgagagcgct aatttttcaa acaaagaatc tgagctgcat ttttacagaa cagaaatgca    11760
acgcgaaagc gctattttac caacgaagaa tctgtgcttc attttttgtaa aacaaaaatg    11820 caacgcgacg agagcgctaa ttttttcaaac aaagaatctg agctgcattt ttacagaaca    11880
gaaatgcaac gcgagagcgc tattttacca acaaagaatc tatacttctt ttttgttcta    11940
caaaaatgca tcccgagagc gctatttttc taacaaagca tcttagatta ctttttttct    12000
cctttgtgcg ctctataatg cagtctcttg ataactttt gcactgtagg tccgttaagg     12060
ttagaagaag gctactttgg tgtctatttt ctcttccata aaaaaagcct gactccactt    12120
cccgcgttta ctgattacta gcgaagctgc gggtgcattt tttcaagata aaggcatccc    12180
cgattatatt ctataccgat gtggattgcg catactttgt gaacagaaag tgatagcgtt    12240
gatgattctt cattggtcag aaaattatga acggtttctt ctattttgtc tctatatact    12300
acgtatagga aatgtttaca ttttcgtatt gttttcgatt cactctatga atagttctta    12360
ctacaatttt tttgtctaaa gagtaatact agagataaac ataaaaaatg tagaggtcga    12420
gtttagatgc aagttcaagg agcgaaaggt ggatgggtag gttatatagg gatatagcac    12480
agagatatat agcaaagaga tacttttgag caatgtttgt ggaagcggta ttcgcaatgc    12540 cggcttttccc cgtcaagctc taaatcgggg gctccctta gggttccgat ttagtgcttt    12600
acggcacctc gaccccaaaa aacttgatta gggtgatggt tcacgtagtg gccatcgcc     12660 ctgatagacg gttttcgcc ctttgacgtt ggagtccacg ttctttaata gtggactctt     12720
gttccaaact ggaacaacac tcaaccctat ctcggtctat tcttttgatt tataagggat    12780
tttgccgatt tcggcctatt ggttaaaaaa tgagctgatt taacaaaaat ttaacgcgaa    12840
ttttaacaaa atattaacgt ttacaatttc ctgatgcggt attttctcct tacgcatctg    12900
tgcggtattt cacaccgcat atgatccgtc gagttcaaga gaaaaaaaaa gaaaagcaa     12960 aagaaaaaaa ggaaagcgcg cctcgttcag aatgacacgt atagaatgat gcattacctt    13020
```

-continued

```
gtcatcttca gtatcatact gttcgtatac atacttactg acattcatag gtatacatat    13080
atacacatgt atatatatcg tatgctgcag ctttaaataa tcggtgtcac tacataagaa    13140 caccctttggt ggagggaaca tcgttggtac cattgggcga ggtggcttct cttatggcaa   13200
ccgcaagagc cttgaacgca ctctcactac ggtgatgatc attcttgcct cgcagacaat    13260
caacgtggag ggtaattctg ctagcctctg caaagctttc aagaaaatgc gggatcatct    13320
cgcaagagag atctcctact ttctcccttt gcaaaccaag ttcgacaact gcgtacggcc    13380
tgttcgaaag atctaccacc gctctggaaa gtgcctcatc caaggcgca aatcctgatc     13440 caaaccttt tactccacgc gccagtaggg cctcttaaaa agcttgaccg agagcaatcc     13500
cgcagtcttc agtggtgtga tggtcgtcta tgtgtaagtc accaatgcac tcaacgatta    13560
gcgaccagcc ggaatgcttg gccagagcat gtatcatatg gtccagaaac cctatacctg    13620
tgtggacgtt aatcacttgc gattgtgtgg cctgttctgc tactgcttct gcctctttt     13680 ctgggaagat cgagtgctct atcgctaggg gaccacccctt taaagagatc gcaatctgaa   13740
tcttggtttc atttgtaata cgctttacta gggctttctg ctctgtcatc tttgccttcg    13800
tttatcttgc ctgctcattt tttagtatat tcttcgaaga aatcacatta ctttatataa    13860
tgtataattc attatgtgat aatgccaatc gctaagaaaa aaaagagtc atccgctagg     13920 tggaaaaaaa aaaatgaaaa tcattaccga ggcataaaaa aatatagagt gtactagagg    13980
aggccaagag taatagaaaa agaaaattgc gggaaaggac tgtgttatga cttccctgac    14040
taatgccgtg ttcaaacgat acctggcagt gactcctagc gctcaccaag ctcttaaaac    14100
ggaattatgg tgcactctca gtacaatctg ctctgatgcc gcatagttaa gccagccccg    14160
acacccgcca acaccccgctg acgcgccctg acgggcttgt ctgctcccgg catccgctta   14220
cagacaagct gtgaccgtct ccgggagctg catgtgtcag aggttttcac cgtcatcacc    14280
gaaacgcgcg a                                                         14291
```

<210> SEQ ID NO 40
<211> LENGTH: 4891
<212> TYPE: DNA
<213> ORGANISM: Artificial
<220> FEATURE:
<223> OTHER INFORMATION: pRN593

<400> SEQUENCE: 40

```
gttttaaatc aatctaaagt atatatgagt aaacttggtc tgacagttac caatgcttaa      60
tcagtgaggc acctatctca gcgatctgtc tatttcgttc atccatagtt gcctgactcc     120
ccgtcgtgta gataactacg atacgggagg gcttaccatc tggccccagt gctgcaatga    180
taccgcgaga cccacgctca ccggctccag atttatcagc aataaaccag ccagccggaa    240
gggccgagcg cagaagtggt cctgcaactt tatccgcctc catccagtct attaattgtt    300
gccgggaagc tagagtaagt agttcgccag ttaatagttt cgcaacgtt gttgccattg     360 ctacaggcat cgtggtgtca cgctcgtcgt ttggtatggc ttcattcagc tccggttccc    420
aacgatcaag gcgagttaca tgatccccca tgttgtgcaa aaaagcggtt agctccttcg    480
gtcctccgat cgttgtcaga agtaagttgg ccgcagtgtt atcactcatg gttatggcag    540
cactgcataa ttctcttact gtcatgccat ccgtaagatg cttttctgtg actggtgagt    600
actcaaccaa gtcattctga gaatagtgta tgcggcgacc gagttgctct tgcccggcgt    660
caatacggga taataccgcg ccacatagca gaactttaaa agtgctcatc attggaaaac    720
```

```
gttcttcggg gcgaaaactc tcaaggatct taccgctgtt gagatccagt tcgatgtaac      780
ccactcgtgc acccaactga tcttcagcat cttttacttt caccagcgtt tctgggtgag      840
caaaaacagg aaggcaaaat gccgcaaaaa agggaataag ggcgacacgg aaatgttgaa      900
tactcatact cttccttttt caattcagaa gaactcgtca agaaggcgat agaaggcgat      960
gcgctgcgaa tcgggagcgg cgataccgta aagcacgagg aagcggtcag cccattcgcc     1020
gccaagctct tcagcaatat cacgggtagc caacgctatg tcctgatagc ggtccgccac     1080
acccagccgg ccacagtcga tgaatccaga aaagcggcca ttttccacca tgatattcgg     1140
caagcaggca tcgccatggt accgagtggt gttgtaacca ccctcaaaaa atgcggaaga     1200
ggtgtacagc taatattata atggaaaatc cttttgctct ataggatttt tttttaaaa      1260
tttaaatata catatttatt tatatttatt tggttactaa attttgtatt aatttaataa     1320
taataagtaa tttctaacgt gataaagtag ttatgagaaa tgacataatg ctaatttatg     1380
aatatgatat agaagagcct cgaaaaaagt gggggaaagt atgatatgtt atctttctcc     1440
aataaatcta atcttcatgt agatctaatt cttcaatcat gtccggcagg ttcttcattg     1500
ggtagttgtt gtaaacgatt tggtatacgg cttcaaataa tgggaagtct tcgacagagc     1560
cacatgtttc caaccattcg tgaacttctt tgcaggtaat taaaccttga gcggattggc     1620
cattcaacaa ctcgtacacc taggatccgt cgacactgga tggcggcgtt agtatcgaat     1680
cgacagcagt atagcgacca gcattcacat acgattgacg catgatatta ctttctgcgc     1740
acttaacttc gcatctgggc agatgatgtc gaggcgaaaa aaaatataaa tcacgctaac     1800
atttgattaa aatagaacaa ctacaatata aaaaaactat acaatgaca agttcttgaa      1860
aacaagaatc ttttttattgt cagtactgat tattcctttg ccctcggacg agtgctgggg     1920
cgtcggtttc cactatcggc gagtacttct acacagccat cggtccagac ggccgcgctt     1980
ctgcgggcga tttgtgtacg cccgacagtc ccggctccgg atcggacgat tgcgtcgcat     2040
cgaccctgcg cccaagctgc atcatcgaaa ttgccgtcaa ccaagctctg atagagttgg     2100
tcaagaccaa tgcggagcat atacgcccgg agccgcggcg atcctgcaag ctccggatgc     2160
ctccgctcga agtagcgcgt ctgctgctcc atacaagcca accacggcct ccagaagaag     2220
atgttggcga cctcgtattg ggaatccccg aacatcgcct cgctccagtc aatgaccgct     2280
gttatgcggc cattgtccgt caggacattg ttggagccga atccgcgtg cacgaggtgc      2340
cggacttcgg ggcagtcctc ggcccaaagc atcagctcat cgagagcctg cgcgacggac     2400
gcactgacgg tgtcgtccat cacagtttgc cagtgataca catggggatc agcaatcgcg     2460
catatgaaat cacgccatgt agtgtattga ccgattcctt gcggtccgaa tgggccgaac     2520
ccgctcgtct ggctaagatc ggccgcagcg atcgcatcca tggcctccgc gaccggctgc     2580
agaacagcgg gcagttcggt ttcaggcagg tcttgcaacg tgacaccctg tgcacggcgg     2640
gagatgcaat aggtcaggct ctcgctgaat tccccaatgt caagcacttc cggaatcggg     2700
agcgcggccg atgcaaagtg ccgataaaca taacgatctt tgtagaaacc atcggcgcag     2760
ctatttaccc gcaggacata tccacgccct cctacatcga agctgaaagc acgagattct     2820
tcgccctccg agagctgcat caggtcgag acgctgtcga acttttcgat cagaaacttc      2880
tcgacagacg tcgcggtgag ttcaggcttt ttacccatgg ttgtttatgt tcggatgtga     2940
tgtgagaact gtatcctagc aagatttttaa aaggaagtat atgaaagaag aacctcagtg     3000
gcaaatccta acctttttata tttctctaca ggggcgcggc gtggggacaa ttcacgcgtc     3060
tgtgagggga gcgtttccct gctcgcaggt ctgcagcgag gagccgtaat ttttgcttcg     3120
```

```
cgccgtgcgg ccatcaaaat gtatggatgc aaatgattat acatggggat gtatgggcta    3180
aatgtacggg cgacagtcac atcatgcccc tgagctgcgc acgtcaagac tgtcaaggag    3240
ggtattctgg gcctccatgt cgctggccgg gtgacccggc ggggacgagg ccttaagttc    3300
gaacgtacga gctccggatt aagggcgaat tccagcacac tggcggccgt tactagacca    3360
gcattcaagt ggccggaagt taagtttaat ctatcagcag cagcagacat ctttatatta    3420
tcaatatttg tgtttgtgga ggggggggggt gtacaatata caattgtttc ttgatgtctt    3480
atgtaggaga gtaagataaa agaaaattaa agggagaaag aatttaaggt aacgtaacag    3540
tttcactcat ggtagtatat atataactac gaaactgcca ataccaagcc agtctacgtg    3600
cgaattaggt tggatagatt tgatgaaccc attctgatac ttgttgtgcg gaaaaaggga    3660
caaaataggg aaaactggaa aaagaaaagg aaggggagag aagcaaggcg ggtaccaagc    3720
ttgatgcata gcttgagtat tctatagtgt cacctaaata gcttggcgta atcatggtca    3780
tagctgtttc ctgtgtgaaa ttgttatccg ctcacaattc cacacaacat acgagccgga    3840
agcataaagt gtaaagcctg gggtgcctaa tgagtgagct aactcacatt aattgcgttg    3900
cgctcactgc ccgctttcca gtcgggaaac ctgtcgtgcc agctgcatta atgaatcggc    3960
caacgcgcgg ggagaggcgg tttgcgtatt gggcgctctt ccgcttcctc gctcactgac    4020
tcgctgcgct cggtcgttcg gctgcggcga gcggtatcag ctcactcaaa ggcggtaata    4080
cggttatcca cagaatcagg ggataacgca ggaaagaaca tgtgagcaaa aggccagcaa    4140
aaggccagga accgtaaaaa ggccgcgttg ctggcgtttt tccataggct ccgcccccct    4200
gacgagcatc acaaaaatcg acgctcaagt cagaggtggc gaaacccgac aggactataa    4260
agataccagg cgtttccccc tggaagctcc ctcgtgcgct ctcctgttcc gaccctgccg    4320
cttaccggat acctgtccgc ctttctccct tcgggaagcg tggcgctttc tcatagctca    4380
cgctgtaggt atctcagttc ggtgtaggtc gttcgctcca agctgggctg tgtgcacgaa    4440
ccccccgttc agcccgaccg ctgcgcctta tccggtaact atcgtcttga gtccaacccg    4500
gtaagacacg acttatcgcc actggcagca gccactggta acaggattag cagagcgagg    4560
tatgtaggcg gtgctacaga gttcttgaag tggtggccta actacggcta cactagaaga    4620
acagtatttg gtatctgcgc tctgctgaag ccagttacct tcggaaaaag agttggtagc    4680
tcttgatccg gcaaacaaac caccgctggt agcggtggtt ttttgtttg caagcagcag    4740 attacgcgca gaaaaaaagg atctcaagaa gatcctttga tcttttctac ggggtctgac    4800
gctcagtgga acgaaaactc acgttaaggg attttggtca tgagattatc aaaaaggatc    4860
ttcacctaga tccttttaaa ttaaaaatga a                                   4891
```

<210> SEQ ID NO 41
<211> LENGTH: 30
<212> TYPE: DNA
<213> ORGANISM: Artificial
<220> FEATURE:
<223> OTHER INFORMATION: Primer gpd1uf

<400> SEQUENCE: 41
aagcttggta cccgccttgc ttctctcccc                                       30

<210> SEQ ID NO 42
<211> LENGTH: 26
<212> TYPE: DNA
<213> ORGANISM: Artificial
<220> FEATURE:

<223> OTHER INFORMATION: Primer gpd1ur

<400> SEQUENCE: 42
tctagaccag cattcaagtg gccgga                                          26

<210> SEQ ID NO 43
<211> LENGTH: 29
<212> TYPE: DNA
<213> ORGANISM: Artificial
<220> FEATURE:
<223> OTHER INFORMATION: Primer gpd1df

<400> SEQUENCE: 43
cgtacgagtt gttgaatggc caatccgct                                       29

<210> SEQ ID NO 44
<211> LENGTH: 31
<212> TYPE: DNA
<213> ORGANISM: Artificial
<220> FEATURE:
<223> OTHER INFORMATION: Primer gpd1dr

<400> SEQUENCE: 44
ccatggtacc gagtggtgtt gtaaccaccc t                                    31

<210> SEQ ID NO 45
<211> LENGTH: 20
<212> TYPE: DNA
<213> ORGANISM: Artificial
<220> FEATURE:
<223> OTHER INFORMATION: Primer gpd1cf

<400> SEQUENCE: 45
accaatacgt aaacggggcg                                                 20

<210> SEQ ID NO 46
<211> LENGTH: 23
<212> TYPE: DNA
<213> ORGANISM: Artificial
<220> FEATURE:
<223> OTHER INFORMATION: Primer gpd1cr

<400> SEQUENCE: 46
aatacaccca tacatacgga cgc                                             23

<210> SEQ ID NO 47
<211> LENGTH: 28
<212> TYPE: DNA
<213> ORGANISM: Artificial
<220> FEATURE:
<223> OTHER INFORMATION: Primer acs1f

<400> SEQUENCE: 47
ttaagcttaa aatgtcgccc tctgccgt                                        28

<210> SEQ ID NO 48
<211> LENGTH: 50
<212> TYPE: DNA
<213> ORGANISM: Artificial
<220> FEATURE:
<223> OTHER INFORMATION: Primer acs1r

<400> SEQUENCE: 48
aagcgcgcta caacttgacc gaatcaatta gatgtctaac aatgccaggg                50

-continued

```
<210> SEQ ID NO 49
<211> LENGTH: 49
<212> TYPE: DNA
<213> ORGANISM: Artificial
<220> FEATURE:
<223> OTHER INFORMATION: Primer acs2f

<400> SEQUENCE: 49
aactgcagaa aatgacaatc aaggaacata aagtagttta tgaagctca        49

<210> SEQ ID NO 50
<211> LENGTH: 49
<212> TYPE: DNA
<213> ORGANISM: Artificial
<220> FEATURE:
<223> OTHER INFORMATION: Primer acs2r

<400> SEQUENCE: 50
acgtcgacta tttcttttt tgagagaaaa attggttctc tacagcaga         49

<210> SEQ ID NO 51
<211> LENGTH: 13018
<212> TYPE: DNA
<213> ORGANISM: Artificial
<220> FEATURE:
<223> OTHER INFORMATION: pRN753

<400> SEQUENCE: 51
gacgaaaggg cctcgtgata cgcctatttt tataggttaa tgtcatgata ataatggttt    60
cttagacgtc aggtggcact tttcggggaa atgtgcgcgg aaccoctatt tgtttatttt   120 tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttt cacaacatgg   660
gggatcatgt aactcgcctt gatcgttggg aaccggagct gaatgaagcc ataccaaacg   720
acgagcgtga ccacacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggca gtcaggcaac tatggatgaa cgaaatagac  1020
agatcgctga gataggtgcc tcactgatta agcattggta actgtcagac caagtttact  1080
catatatact ttagattgat ttaaaacttc attttaatt taaaggatc taggtgaaga  1140 tcctttttga taatctcatg accaaaatcc cttaacgtga gttttcgttc cactgagcgt  1200
cagaccccgt agaaaagatc aaaggatctt cttgagatcc ttttttctg cgcgtaatct  1260 gctgcttgca acaaaaaaaa ccaccgctac cagcggtggt ttgtttgccg gatcaagagc  1320
taccaactct ttttccgaag gtaactggct tcagcagagc gcagatacca aatactgtcc  1380
```

-continued

```
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acgggggtt     1560 cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg ggggaacgcc tggtatcttt    1740
atagtcctgt cgggtttcgc cacctctgac ttgagcgtcg atttttgtga tgctcgtcag    1800
gggggccgag cctatggaaa aacgccagca acgcggcctt tttacggttc ctggccttt    1860 gctggccttt tgctcacatg ttcttcctg cgttatcccc tgattctgtg ataaccgta     1920 ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttac ctcactcatt aggcacccca ggctttacac tttatgcttc    2160
cggctcctat gttgtgtgga attgtgagcg gataacaatt tcacacagga aacagctatg    2220
accatgatta cgccaagctc ggaattaacc ctcactaaag ggaacaaaag ctgggtaccg    2280
ggccccccct cgaccggtcc cacacaccat agcttcaaaa tgtttctact ccttttttac    2340
tcttccagat tttctcggac tccgcgcatc gccgtaccac ttcaaaacac ccaagcacag    2400
catactaaat ttcccctctt tcttcctcta gggtgtcgtt aattacccgt actaaaggtt    2460
tggaaaagaa aaaagagacc gcctcgtttc ttttcttcg tcgaaaaagg caataaaaat    2520
ttttatcacg tttctttttc ttgaaaattt tttttttga ttttttttctc tttcgatgac    2580 ctcccattga tatttaagtt aataaacggt cttcaatttc tcaagtttca gtttcatttt    2640
tcttgttcta ttacaacttt tttacttct tgctcattag aaagaaagca tagcaatcta    2700
atctaagctg cagaagctta aaatgtcgcc ctctgccgta caatcatcaa aactagaaga    2760
acagtcaagt gaaattgaca gttgaaagc aaaaatgtcc cagtctgccg ccactgcgca    2820
gcagaagaag gaacatgagt atgaacattt gacttcggtc aagatcgtgc cacaacggcc    2880
catctcagat agactgcagc ccgcaattgc tacccactat tctccacact tggacgggtt    2940
gcaggactat cagcgcttgc acaaggagtc tattgaagac cctgctaagt tcttcggttc    3000
taaagctacc caattttta actggtctaa gccattcgat aaggtgttca tcccagaccc    3060
taaaacgggc aggccctcct tccagaacaa tgcatggttc ctcaacggcc aattaaacgc    3120
ctgttacaac tgtgttgaca gacatgcctt gaagactcct aacaagaaag ccattatttt    3180
cgaaggtgac gagcctggcc aaggctattc cattacctac aaggaactac ttgaagaagt    3240 tgtcaagtg gcacaagtgc tgacttactc tatgggcgtt cgcaagggcg atactgttgc    3300
cgtgtacatg cctatggtcc cagaagcaat cataaccttg ttggccattt cccgtatcgg    3360
tgccattcac tccgtagtct ttgccgggtt ttcttccaac tccttgagag atcgtatcaa    3420
cgatggggac tctaaagttg tcatcactac agatgaatcc aacagaggtg gtaaagtcat    3480
tgagactaaa agaattgttg atgacgcgct aagagagacc ccaggcgtga cacgtctt     3540 ggtttataga aagaccaaca atccatctgt tgctttccat gccccagag atttggattg     3600 ggcaacagaa aagaagaaat acaagaccta ctatccatgc acacccgttg attctgagga    3660
tccattattc ttgttgtata cgtctggttc tactggtgcc cccaagggtg ttcaacattc    3720
taccgcaggt tacttgctgg gagctttgtt gaccatgcgc tacacttttg acactcacca    3780
```

```
agaagacgtt ttcttcacag ctggagacat tggctggatt acaggccaca cttatgtggt    3840
ttatggtccc ttactatatg gttgtgccac tttggtcttt gaagggactc ctgcgtaccc    3900
aaattactcc cgttattggg atattattga tgaacacaaa gtcacccaat tttatgttgc    3960
gccaactgct ttgcgtttgt tgaaaagagc tggtgattcc tacatcgaaa atcattcctt    4020
aaaatctttg cgttgcttgg gttcggtcgg tgagccaatt gctgctgaag tttgggagtg    4080
gtactctgaa aaataggta aaatgaaat ccccattgta gacacctact ggcaaacaga    4140
atctggttcg catctggtca ccccgctggc tggtggtgtt acaccaatga aaccgggttc    4200
tgcctcattc cccttcttcg gtattgatgc agttgttctt gaccctaaca ctggtgaaga    4260
acttaacacc agccacgcag agggtgtcct tgccgtcaaa gctgcatggc catcatttgc    4320
aagaactatt tggaaaaatc atgataggta tctagacact tatttgaacc cttaccctgg    4380
ctactatttc actggtgatg gtgctgcaaa ggataaggat ggttatatct ggattttggg    4440
tcgtgtagac gatgtggtga acgtctctgg tcaccgtctg tctaccgctg aaattgaggc    4500
tgctattatc gaagatccaa ttgtggccga gtgtgctgtt gtcggattca acgatgactt    4560
gactggtcaa gcagttgctg catttgtggt gttgaaaaac aaatctagtt ggtccaccgc    4620
aacagatgat gaattacaag atatcaagaa gcatttggtc tttactgtta gaaaagacat    4680
cgggccattt gccgcaccaa aattgatcat tttagtggat gacttgccca agacaagatc    4740
cggcaaaatt atgagacgta ttttaagaaa aatcctagca ggagaaagtg accaactagg    4800
cgacgtttct acattgtcaa accctggcat tgttagacat ctaattgatt cggtcaagtt    4860
gtaacttaag cgcgcgaatt tcttatgatt tatgattttt attattaaat aagttataaa    4920
aaaaataagt gtatacaaat tttaaagtga ctcttaggtt ttaaaacgaa aattcttatt    4980
cttgagtaac tctttcctgt aggtcaggtt gctttctcag gtatagcatg aggtcgctct    5040
tattgaccac acctctaccg gcatgccgag caaatgcctg caaatcgctc cccatttcac    5100
ccaattgtag atatgctaac tccagcaatg agttgatgaa tctcggtgtg tattttatgt    5160
cctcagagga caacacctgt tgtaatcgtt cttccacacg tacgttttaa acagttgatg    5220
agaacctttt tcgcaagttc aaggtgctct aattttttaaa attttttactt ttcgcgacac    5280 aataaagtct tcacgacgct aaactattag tgcacataat gtagttactt ggacgctgtt    5340
caataatgta taaaatttat ttcctttgca ttacgtacat tatataaacca aatcttaaaa    5400 atatagaaat atgatatgtg tataataata taagcaaaat ttacgtatct ttgcttataa    5460
tatagcttta atgttcttta ggtatatatt taagagcgat ttgtctcgac tatttctttt    5520
tttgagagaa aaattggttc tctacagcag aaatgatggc aggtacaact tctgggttgg    5580
ccaaagtagt taggtcacct agctgttcgg cttcgttaga agcaaccttt cttagaactc    5640
ttctcataat ctttcctgac cttgttcttg gtagatctct aactagaata atggttttg    5700 gtgaggcgaa aggaccaatc tcaccctaa ccttgtaagt caattctcta cgtaaattat    5760
ctggtgtgat gtgttctgca tcaccttcag tagcgttgtt ttgtagataa ccatctttta    5820
gggaaacata tgcaacgacg gtttgaccgg tcaattcatc tggaataccg acaacagcag    5880
cttccgagac gttttcgtga tttgagatag atgcttcaat ttctgatgtg gataatctat    5940
gaccggaaac atttacaacg tcgtcaactc taccctgat ccagtagtaa ccatcatgat    6000
ctctaccagc accatcacct gtgaaatagt gaccaggata aggtttcaag taagtatcca    6060
tgtaacggtc gtggtggttc caaacagatc tagccattga tggccatggt gatttaacgg    6120
```

```
caaggacacc ttcgacatca ttaccttcta attccacacc tgtaacaggg tcaatgatac    6180
aagcgttaat accaaagaat ggcacggtag cagaaccagg ttttgttggg acagcacctg    6240
ccaaaggagc aattaaatga gaaccagact ctgtttgcca catagtgtca caaatgacac    6300 agttttttgtt acccactttt tcatgatacc attcccataa gtctggagag attggttcac    6360
cgacggaacc caagacacgt aatgaggaag tgtcatattt ggcaatttcg gcttcaccta    6420 cacgttttgat taatcttaaa gcagttggag ccacatagaa atgggtagcc ttgtgacgtt    6480
ggataattct ccaatatcta ccataatctg ggtaggcagg agtggattcg aaaattattg    6540
aggcggtacc caaggttaat ggaccatata gagcataggt gtgacccgtg atccagccga    6600
cgtcaccggc agtgaagaga acatcttctg ggtgaatatc aaaaacgtat ctagttgtta    6660
aagcggcacc taataaataa ccacctgtag tgtgaacgac acccttttgga gaaccagtgg    6720 aaccggaagt gtataataaa aatagaggat cttcagcgtc acatgaaaca ggaggtaggt    6780
aagttctctg cttagcggcc tcctcatgcc accagtaatc tctaccggcc ttcattggaa    6840
taccttcagt accagttctt tggaaaacca agatacggga aaccaaatcg actccgttca    6900
aaccttcgtc aacaattttt ttagtgttga tggtcttacc acctctttta ccttcatcac    6960
aagtgatgac cactttagaa ttagcgtcaa cgacacgatc tttcaacgaa ccagcggaga    7020
acccagcaaa gacaacagag tgaatagcac caatacgagc cacagccaac atagcaatga    7080
ccgcttctgg aatcattggc aaatagatag ccactgtgtc acctttctta acgcccagc    7140 ttttttaagac accagcgatt tgggaaactt ttctgagtaa ttcaccaaat gtgatgattt    7200
tgttgtcgga ttcgtcatca gcttcataga tcaaagctgg cttgtcggga ttagcaaagg    7260
catgtctgtc aacacaattg tatgatgcat tcaatttacc gttcaaaaac catgcaacat    7320
caccattgtt caatgaacca gattgaactt tggtgtatgg agcatcccaa tgcaagtatt    7380
ccttagccat cttatcaaag aattttttctg gctcattgat agattgttga tacatttctt    7440
gataatgttg catatcagta acgtaaccct tgccggggttg gctgttgtaa aaatgttgag    7500
gagccttaag agcctttacg ttgtgagctt cataaactac tttatgttcc ttgattgtca    7560
ttttctgcag tctagatata tttgttgtaa aaagtagata attacttcct tgatgatctg    7620 taaaaagag aaaagaaag catctaagaa cttgaaaaac tacgaattag aaaagaccaa    7680
atatgtattt cttgcattga ccaatttatg caagtttata tatatgtaaa tgtaagtttc    7740
acgaggttct actaaactaa accaccccct tggttagaag aaaagagtgt gtgagaacag    7800
gctgttgttg tcacacgatt cggacaattc tgtttgaaag agagagagta acagtacgat    7860
cgaacgaact ttgctctgga gatcacagtg ggcatcatag catgtggtac taaacccttt    7920
cccgccattc cagaaccttc gattgcttgt tacaaaacct gtgagccgtc gctaggacct    7980
tgttgtgtga cgaaattgga agctgcaatc aataggaaga caggaagtcg agcgtgtctg    8040
ggttttttca gttttgttct ttttgcaaac aaatcacgag cgacggtaat ttctttctcg    8100
ataagaggcc acgtgcttta tgagggtaac atcaattcaa gaaggaggga aacacttcct    8160
ttttctggcc ctgataatag tatgagggtg aagccaaaat aaaggattcg cgcccaaatc    8220
ggcatcttta aatgcaggta tgcgatagtt cctcactctt ccttactca cgagtaattc    8280 ttgcaaatgc ctattatgca gatgttataa tatctgtgcg tcttgagttg aagagctcga    8340
gactagatgc atgctcgagc ggccgccagt gtgatggata tctgcagaat tcgcccttt    8400 gggccctgta cacctaggat ccgtcgacac tggatggcgg cgttagtatc gaatcgacag    8460
cagtatagcg accagcattc acatacgatt gacgcatgat attactttct gcgcacttaa    8520
```

```
cttcgcatct gggcagatga tgtcgaggcg aaaaaaaata taaatcacgc taacatttga   8580
ttaaaataga acaactacaa tataaaaaaa ctatacaaat gacaagttct tgaaaacaag   8640 aatctttta ttgtcagtac tgattagaaa aactcatcga gcatcaaatg aaactgcaat    8700
ttattcatat caggattatc aataccatat ttttgaaaaa gccgtttctg taatgaagga   8760
gaaaactcac cgaggcagtt ccataggatg gcaagatcct ggtatcggtc tgcgattccg   8820
actcgtccaa catcaataca acctattaat ttcccctcgt caaaaataag gttatcaagt   8880
gagaaatcac catgagtgac gactgaatcc ggtgagaatg gcaaaagctt atgcatttct   8940
ttccagactt gttcaacagg ccagccatta cgctcgtcat caaaatcact cgcatcaacc   9000
aaaccgttat tcattcgtga ttgcgcctga gcgagacgaa atacgcgatc gctgttaaaa   9060
ggacaattac aaacaggaat cgaatgcaac cggcgcagga acactgccag cgcatcaaca   9120
atattttcac ctgaatcagg atattcttct aatacctgga atgctgtttt gccggggatc   9180
gcagtggtga gtaaccatgc atcatcagga gtacggataa aatgcttgat ggtcggaaga   9240
ggcataaatt ccgtcagcca gtttagtctg accatctcat ctgtaacatc attggcaacg   9300
ctacctttgc catgtttcag aaacaactct ggcgcatcgg gcttcccata caatcgatag   9360
attgtcgcac ctgattgccc gacattatcg cgagcccatt tatacccata taaatcagca   9420
tccatgttgg aatttaatcg cggcctcgaa acgtgagtct tttccttacc catgttgtt    9480 tatgttcgga tgtgatgtga aactgtatc ctagcaagat tttaaaagga agtatatgaa    9540
agaagaacct cagtggcaaa tcctaacctt ttatatttct ctacaggggc gcggcgtggg   9600
gacaattcaa cgcgtctgtg aggggagcgt ttccctgctc gcaggtctgc agcgaggagc   9660 cgtaatttt gcttcgcgcc gtgcggccat caaaatgtat ggatgcaaat gattatacat    9720
ggggatgtat gggctaaatg tacgggcgac agtcacatca tgcccctgag ctgcgcacgt   9780
caagactgtc aaggagggta ttctgggcct ccatgtcgct ggccgggtga cccggcgggg   9840
acgaggcctt aagttcgaac gtacgagctc cggattatcg atgataagct gtcaaagatg   9900
agaattaatt ccacggacta tagactatac tagatactcc gtctactgta cgatacactt   9960
ccgctcaggt ccttgtcctt taacgaggcc ttaccactct tttgttactc tattgatcca  10020
gctcagcaaa ggcagtgtga tctaagattc tatcttcgcg atgtagtaaa actagctaga  10080
ccgagaaaga gactagaaat gcaaaaggca cttctacaat ggctgccatc attattatcc  10140
gatgtgacgc tgcagcttct caatgatatt cgaatacgct tgaggagat acagcctaat   10200 atccgacaaa ctgttttaca gatttacgat cgtacttgtt acccatcatt gaattttgaa  10260
catccgaacc tgggagtttt ccctgaaaca gatagtatat ttgaacctgt ataataatat  10320
atagtctagc gctttacgga agacaatgta tgtatttcgg ttcctggaga aactattgca  10380
tctattgcat aggtaatctt gcacgtcgca tccccggttc attttctgcg tttccatctt  10440
gcacttcaat agcatatctt tgttaacgaa gcatctgtgc ttcattttgt agaacaaaaa  10500
tgcaacgcga gagcgctaat ttttcaaaca aagaatctga gctgcatttt tacagaacag  10560
aaatgcaacg cgaaagcgct attttaccaa cgaagaatct gtgcttcatt tttgtaaaac  10620
aaaaatgcaa cgcgacgaga gcgctaattt ttcaaacaaa gaatctgagc tgcattttta  10680
cagaacagaa atgcaacgcg agagcgctat tttaccaaca aagaatctat acttcttttt  10740
tgttctacaa aaatgcatcc cgagagcgct atttttctaa caaagcatct tagattactt  10800 ttttctcct tgtgcgctc tataatgcag tctcttgata acttttgca ctgtaggtcc      10860
```

```
gttaaggtta gaagaaggct actttggtgt ctattttctc ttccataaaa aaagcctgac  10920
tccacttccc gcgtttactg attactagcg aagctgcggg tgcattttt  caagataaag  10980 gcatccccga ttatattcta taccgatgtg gattgcgcat actttgtgaa cagaaagtga  11040
tagcgttgat gattcttcat tggtcagaaa attatgaacg gtttcttcta ttttgtctct  11100
atatactacg tataggaaat gtttacattt tcgtattgtt ttcgattcac tctatgaata  11160
gttcttacta caatttttt  gtctaaagag taatactaga gataaacata aaaaatgtag  11220
aggtcgagtt tagatgcaag ttcaaggagc gaaggtgga  tgggtaggtt atatagggat  11280
atagcacaga gatatatagc aaagagatac ttttgagcaa tgtttgtgga agcggtattc  11340
gcaatgccgg cttccccgt  caagctctaa atcgggggct cccttaggg  ttccgattta  11400 gtgcttacg  gcacctcgac cccaaaaaac ttgattaggg tgatggttca cgtagtgggc  11460
catcgccctg atagacggtt tttcgcccct tgacgttgga gtccacgttc tttaatagtg  11520
gactcttgtt ccaaactgga acaacactca accctatctc ggtctattct tttgatttat  11580
aagggatttt gccgatttcg gcctattggt taaaaatga  gctgatttaa caaaaattta  11640
acgcgaattt taacaaaata ttaacgttta caatttcctg atgcggtatt ttctccttac  11700
gcatctgtgc ggtatttcac accgcagggt aataactgat ataattaaat tgaagctcta  11760
atttgtgagt ttagtataca tgcatttact tataatacag ttttttagtt ttgctggccg  11820
catcttctca aatatgcttc ccagcctgct tttctgtaac gttcaccctc taccttagca  11880
tcccttccct ttgcaaatag tcctcttcca acaataataa tgtcagatcc tgtagagacc  11940
acatcatcca cggttctata ctgttgaccc aatgcgtctc ccttgtcatc taaacccaca  12000
ccgggtgtca taatcaacca atcgtaacct tcatctcttc cacccatgtc tctttgagca  12060
ataaagccga taacaaaatc tttgtcgctc ttcgcaatgt caacagtacc cttagtatat  12120
tctccagtag atagggagcc cttgcatgac aattctgcta acatcaaaag gcctctaggt  12180
tcctttgtta cttcttctgc cgcctgcttc aaaccgctaa caatacctgg gcccaccaca  12240
ccgtgtgcat tcgtaatgtc tgcccattct gctattctgt atacacccgc agagtactgc  12300
aatttgactg tattaccaat gtcagcaaat tttctgtctt cgaagagtaa aaaattgtac  12360
ttggcggata atgcctttag cggcttaact gtgccctcca tggaaaaatc agtcaagata  12420
tccacatgtg tttttagtaa acaaattttg ggacctaatg cttcaactaa ctccagtaat  12480
tccttggtgg tacgaacatc caatgaagca cacaagtttg tttgcttttc gtgcatgata  12540
ttaaatagct tggcagcaac aggactagga tgagtagcag cacgttcctt atatgtagct  12600
ttcgacatga tttatcttcg tttcctgcag gttttttgttc tgtgcagttg ggttaagaat  12660
actgggcaat ttcatgtttc ttcaacacta catatgcgta tatataccaa tctaagtctg  12720
tgctccttcc ttcgttcttc cttctgttcg gagattaccg aatcaaaaaa atttcaaaga  12780
aaccgaaatc aaaaaaaaga ataaaaaaaa aatgatgaat tgaattgaaa agcgtggtgc  12840
actctcagta caatctgctc tgatgccgca tagttaagcc agccccgaca cccgccaaca  12900
cccgctgacg cgccctgacg ggcttgtctg ctcccggcat ccgcttacag acaagctgtg  12960
accgtctccg ggagctgcat gtgtcagagg ttttcaccgt catcaccgaa acgcgcga    13018
```